(12) United States Patent
Saiki et al.

(10) Patent No.: US 9,182,384 B2
(45) Date of Patent: Nov. 10, 2015

(54) ANALYZING DEVICE AND ANALYZING METHOD USING SAME

(75) Inventors: Hiroshi Saiki, Ehime (JP); Kouzou Tagashira, Ehime (JP); Hirofumi Sugimoto, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 137 days.

(21) Appl. No.: 12/741,929

(22) PCT Filed: Nov. 7, 2008

(86) PCT No.: PCT/JP2008/003222
§ 371 (c)(1),
(2), (4) Date: May 7, 2010

(87) PCT Pub. No.: WO2009/060617
PCT Pub. Date: May 14, 2009

(65) Prior Publication Data
US 2010/0240142 A1    Sep. 23, 2010

(30) Foreign Application Priority Data

| Nov. 8, 2007 | (JP) | ................................ 2007-290240 |
| Dec. 20, 2007 | (JP) | ................................ 2007-328093 |
| Feb. 5, 2008 | (JP) | ................................ 2008-024623 |
| Mar. 25, 2008 | (JP) | ................................ 2008-076911 |

(51) Int. Cl.
*G01N 21/07* (2006.01)
*G01N 33/49* (2006.01)
*B01L 3/00* (2006.01)

(52) U.S. Cl.
CPC .......... *G01N 33/491* (2013.01); *B01L 3/50273* (2013.01); *B01L 3/502753* (2013.01); *G01N 21/07* (2013.01); *B01L 2200/027* (2013.01); *B01L 2200/04* (2013.01); *B01L 2200/0642* (2013.01); *B01L 2200/10* (2013.01);
(Continued)

(58) Field of Classification Search
None
See application file for complete search history.

(56) References Cited

U.S. PATENT DOCUMENTS

| 4,894,204 A | 1/1990 | Cornut |
| 5,061,381 A | 10/1991 | Burd |

(Continued)

FOREIGN PATENT DOCUMENTS

| CN | 1613542 | 5/2005 |
| CN | 1682112 | 10/2005 |

(Continued)

OTHER PUBLICATIONS

Software translation of Shinjo T., JP-2005-345160, Dec. 15, 2005.*
(Continued)

*Primary Examiner* — Yelena G Gakh
*Assistant Examiner* — Michelle Adams
(74) *Attorney, Agent, or Firm* — Hamre, Schumann, Mueller & Larson, P.C.

(57) ABSTRACT

An analyzing device configured to separate a solution component 18a in a separating cavity 23, which is connected to a measuring cavity through a connecting channel 37 and a measurement channel 38. A first capillary cavity 33 is provided on one side of the separating cavity 23 so as to communicate with the connecting channel 37. The first capillary cavity 33 is formed to extend to the outside of a separation interface 18c of a sample liquid separated in the separating cavity 23.

7 Claims, 60 Drawing Sheets

(52) U.S. Cl.
CPC .. *B01L2300/0654* (2013.01); *B01L 2300/0806* (2013.01); *B01L 2400/0409* (2013.01); *Y10T 436/111666* (2015.01)

(56) References Cited

U.S. PATENT DOCUMENTS

| | | | |
|---|---|---|---|
| 5,160,702 | A | 11/1992 | Kopf-Sill et al. |
| 5,173,193 | A | 12/1992 | Schembri |
| 5,286,454 | A * | 2/1994 | Nilsson et al. ............... 422/548 |
| 5,304,348 | A | 4/1994 | Burd et al. |
| 2002/0076354 | A1 | 6/2002 | Cohen |
| 2004/0232074 | A1 | 11/2004 | Peters et al. |
| 2005/0084422 | A1 | 4/2005 | Kido et al. |
| 2005/0126312 | A1 | 6/2005 | Bedingham et al. |
| 2006/0073075 | A1 | 4/2006 | Nagaoka et al. |
| 2006/0144802 | A1 | 7/2006 | Kitawaki et al. |
| 2009/0087345 | A1 | 4/2009 | Yamamoto |
| 2009/0123337 | A1 | 5/2009 | Noda et al. |
| 2009/0169430 | A1 | 7/2009 | Yamamoto et al. |

FOREIGN PATENT DOCUMENTS

| | | |
|---|---|---|
| CN | 1755370 | 4/2006 |
| EP | 1550871 | 7/2005 |
| JP | 61-167469 | 7/1986 |
| JP | 01-502850 | 9/1989 |
| JP | 4-504758 | 8/1992 |
| JP | 5-508709 | 12/1993 |
| JP | 7-503794 | 4/1995 |
| JP | 2001-083081 | 3/2001 |
| JP | 2004-205292 | 7/2004 |
| JP | 2004-283828 | 10/2004 |
| JP | 2005-502031 | 1/2005 |
| JP | 2005-345160 | 12/2005 |
| JP | 2007-10435 | 1/2007 |
| JP | 2007-021450 | 2/2007 |
| JP | 2007-078676 | 3/2007 |
| JP | 2007-232673 | 9/2007 |
| JP | 2010-503859 | 2/2010 |
| WO | WO 88/07668 | 10/1988 |
| WO | 90/13016 | 11/1990 |
| WO | 91/18658 | 12/1991 |
| WO | WO 91/18656 | 12/1991 |
| WO | 93/16391 | 8/1993 |
| WO | WO 98/53311 | 11/1998 |
| WO | WO 02/43866 | 6/2002 |
| WO | 03/018198 | 3/2003 |
| WO | 2005/116662 | 12/2005 |
| WO | WO 2006/009750 | 1/2006 |
| WO | WO 2006/070772 | 7/2006 |
| WO | WO 2006/137431 | 12/2006 |
| WO | WO 2007/105764 | 9/2007 |
| WO | WO 2007/116909 | 10/2007 |
| WO | WO 2008/033521 | 3/2008 |

OTHER PUBLICATIONS

Software translation of Saeki H. et al., JP-2007-078676-A; Mar. 29, 2007.*

International Search Report of PCT/JP2008/003222, dated Jan. 27, 2009.

* cited by examiner

FIG. 12
(a)
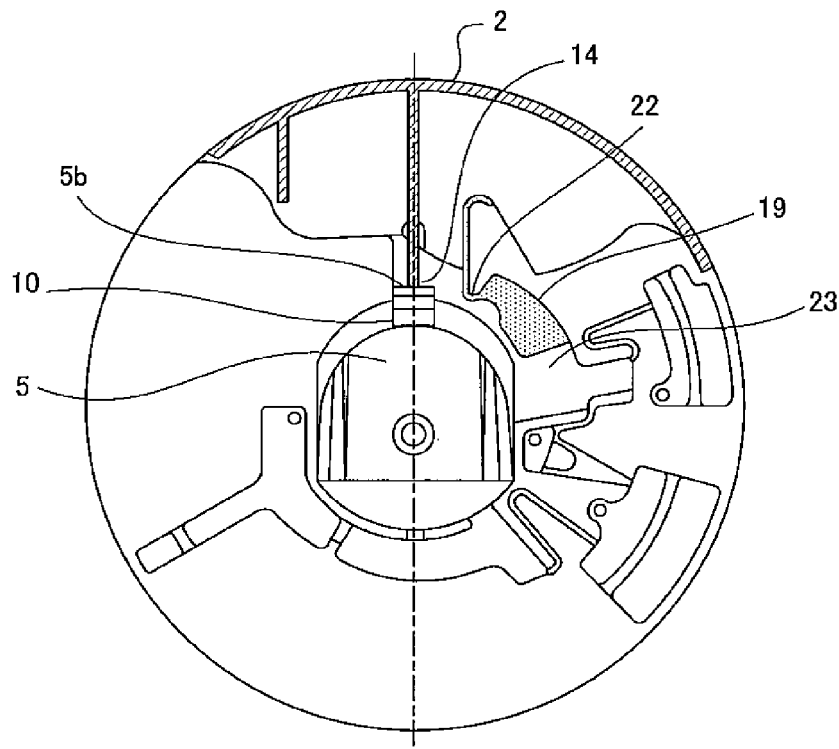
(b)
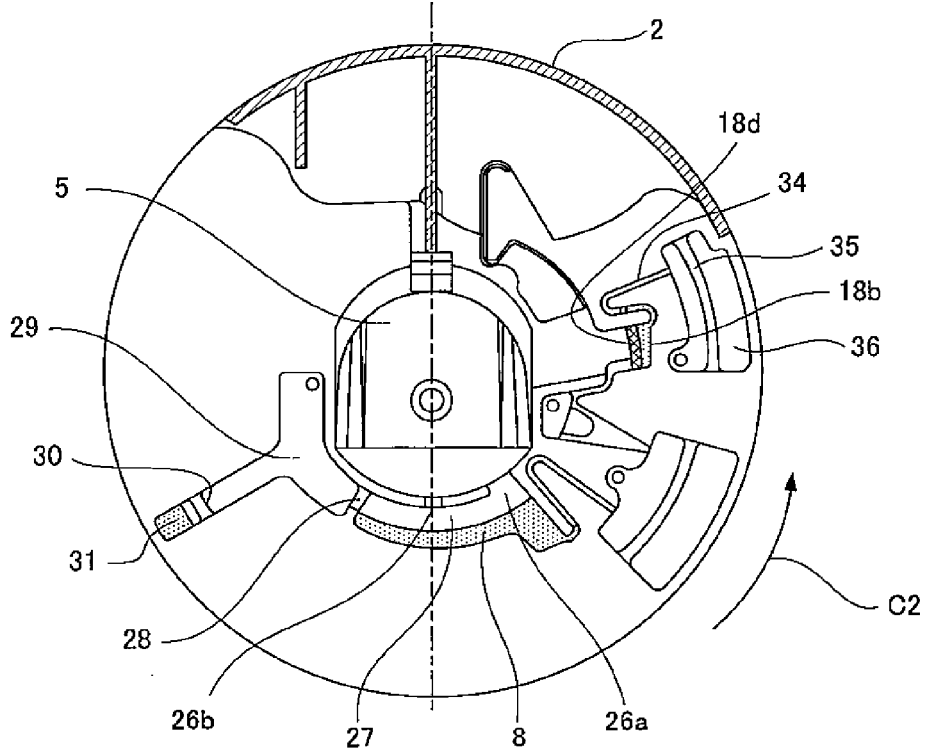

ANALYZING DEVICE AND ANALYZING METHOD USING SAME

TECHNICAL FIELD

The present invention relates to an analyzing device used for analyzing a liquid collected from an organism and the like and an analyzing method using the same, and the present invention more specifically relates to a method of collecting a solution component of a sample liquid separated in the analyzing device and, to be specific, a technique for collecting a plasma component in blood.

BACKGROUND ART

In the prior art, liquids collected from organisms and the like have been analyzed by known methods using analyzing devices in which liquid channels are formed. Such analyzing devices can control fluids by using rotators. Further, such analyzing devices can dilute sample liquids, measure solutions, separate solid components, transfer/distribute separated fluids, and mix solutions and reagents by using centrifugal forces, thereby enabling various biochemical analyses.

In an analyzing device for transferring a solution by using a centrifugal force according to Patent Document 1, as shown in FIG. 59A, a sample liquid is collected from an inlet 55 to fill a first cavity 56 by capillarity and then the sample liquid in the first cavity 56 is transferred to a separating cavity 58 by rotating an analyzing device 54 about an axis 57. After that, as shown in FIG. 59B, the sample liquid is centrifugally separated into a plasma component 59a and a blood cell component 59b. The plasma component 59a in the separating cavity 58 is drawn into a cavity 62 through a capillary cavity 61 connected to one end of a capillary channel 60, and a mixture obtained by mixing the plasma component 59a with a reagent retained in the cavity 62 is analyzed by a photometer.

Patent Document 2, Patent Document 3, and Patent Document 4 describe analyzing methods for measuring samples by using centrifugal forces.

FIG. 60 shows the technique of Patent Document 2.

Provided from the center to the outer edge of an analyzing device are a central storage portion 143 for storing a liquid to be diluted before analysis, a measuring chamber 144, an overflow chamber 145, a mixing chamber 146, and measurement cells 147. The measuring chamber 144 is disposed substantially in parallel with the overflow chamber 145, and an opening 150 is provided on the wall surface of the measuring chamber in addition to a feed port 148 and an overflow port 149 so as to be opposed to the feed port 148. The opening 150 is always opened and has a cross section much smaller than those of the feed port 148 and the overflow port 149.

This configuration makes it possible to fill the measuring chamber 144 at high speeds and quickly remove an overflow. When the measuring chamber 144 is filled with a liquid, the liquid immediately starts flowing out of the chamber. Thus it is possible to reduce a ratio of a "feed time" to an outflow time of an "outlet", the ratio being a function of a ratio of an "inlet sectional area" to an "outlet sectional area". Hence, accurate measurement can be achieved.

FIG. 61 shows the technique of Patent Document 3.

This analyzing device has a fluid chamber 151, a measuring chamber 152 that is connected to the fluid chamber 151 and is disposed outside the fluid chamber 151 in the radial direction, an overflow chamber 153 connected to the measuring chamber 152, a receiving chamber 154 disposed outside the measuring chamber 152 in the radial direction, and a capillary connecting device 155 for supplying a liquid from the measuring chamber 152 to the receiving chamber 154. The capillary connecting device 155 has a siphon 156 having a capillary structure. The elbowed portion of the siphon 156 is positioned at substantially the same distance from the center of the analyzing device as the innermost point of the measuring chamber 152 in the radial direction, so that a capillary force is smaller than a centrifugal force during a rotation of the analyzing device. For this reason, the interface of liquid/air has the same axis as the analyzing device, the measuring chamber 152 is filled according to the shape of a rotating cylinder having a radius as long as the distance from the center of the analyzing device to the innermost point of the measuring chamber 152 in the radius direction, and an excessive fluid flows into the overflow chamber 153. When the analyzing device is stopped, the liquid supplied into the measuring chamber 152 flows into the capillary connecting device 155 by a capillary force. When the analyzing device is rotated again, the siphon starts to discharge the liquid in the measuring chamber 152 to the receiving chamber 154.

FIG. 62 shows the technique of Patent Document 4.

This analyzing device includes a retaining part 157 having the outer side shaped like a fan extending from the inner periphery to the outer periphery, and a blood cell storing part 158. A portion 159 for connecting the blood cell storing part 158 and the retaining part 157 is convexly formed to prevent a blood cell component fed by centrifugal separation from flowing backward to the retaining part 157. Further, a siphon-shaped output channel 160 is connected to a side of the retaining part 157 and is followed by a configuration in which a sample liquid after an operation can be supplied to the subsequent operation region. Initial blood is supplied to the retaining part 157 through an output channel 161, and a blood cell component having a large specific gravity in the supplied blood is stored in the blood cell storing part 158 by a centrifugal force. The number of revolutions of the analyzing device is reduced when the separation is nearly completed, so that a balance between a capillary force that is applied to a solution in the output channel 160 connected to the retaining part 157 and a centrifugal force is reversed and plasma and serum components remaining in the retaining part 157 are discharged to the subsequent operation region through the output channel 160 by centrifugal separation.

In recent years, there have been growing demands in the market for a reduction in the volume of a sample liquid, size reduction of a device, short-time measurement, simultaneous measurement on multiple items, and so on. Thus more accurate analyzers have been demanded to react a sample liquid such as blood with various analytical reagents, detect a mixture of the sample liquid, and inspect the stages of various diseases in a short time.

Generally, in such an analyzing device, a sample liquid is rarely reacted as it is with a reagent and frequently requires pretreatment such as the dilution of the sample liquid with a buffer solution and the like and the removal of fine particles in the sample liquid according to the purpose of analysis. For example, when the sample liquid is diluted, it is necessary to accurately derive a dilution factor in an actual calculation process of a measurement value.

The analyzing device of Patent Document 5 is an example in which pretreatment is performed and a dilution factor is derived optically on the analyzing device.

FIG. 63 shows the analyzing device of Patent Document 5.

A rotor body 202 is substantially formed of a solid disk. FIG. 44 shows a bottom layer 204 of the rotor body 202. An enclosed reagent container 206 is placed in a chamber 208 of the bottom layer 204 and extends from an outlet channel 210 to the inside in the radial direction. A reagent is transferred into a mixing chamber 212 through the outlet channel 210.

The reagent container 206 contains a diluent to be mixed with a biological sample. For example, when the sample is blood, the diluent may be an ordinary saline solution (0.5% saline solution), a phosphoric acid buffer solution, a Ringer lactate solution, and a standard diluent similar to these solutions. The enclosed reagent container 206 is opened in response to the installation of the rotor body 202 in an analyzer. After the opening of the reagent container 206, the reagent in the reagent container 206 flows into the mixing chamber 212 through the outlet channel 210.

The mixing chamber 212 contains a marker mixture that is photometrically detectable and specifies the dilution of the biological sample to be tested.

After the mixing, the diluent flows out of the mixing chamber 212 into a measuring chamber 216 through a siphon 214. The measuring chamber 216 is connected to an overflow chamber 218. The volume of the measuring chamber 216 is smaller than that of the reagent container 206. An excessive volume of the diluent flows into the overflow chamber 218 with a predetermined volume of the diluent remaining in the measuring chamber 216. The excessive volume of the diluent in the overflow chamber 218 flows into a collecting chamber 222 through a passage 220.

Next, for use as a reference value in an optical analysis of the biological sample, the diluent flows outward in the radius direction and flows into system cuvettes 224. The predetermined volume of the diluent in the measuring chamber 216 flows into a separating chamber 228 through a siphon 226 and is mixed with the biological sample to be analyzed, so that the sample is diluted. The sample is supplied into the rotor body 202 through an inlet on a top layer (not shown).

A sample measuring chamber 230 is connected to a sample overflow chamber 232 via a connecting channel 234. The depths of the sample measuring chamber 230 and the overflow chamber 232 are selected to be capillary dimensions. The measured sample then flows into the separating chamber 228. The separating chamber 228 is used for removing cellular materials from a biological sample such as whole blood. The separating chamber 228 is made up of a cell trap 236 formed on the outer periphery relative to the radial direction and a receiving hole region 238 formed along the inner periphery relative to the radial direction. A capillary region (not shown) is formed between the receiving hole region 238 and the cell trap 236 to prevent backflow of a cellular component trapped in the cell trap 236 as a result of centrifugal separation. The volume of the receiving hole region 238 is so large as to receive plasma containing no diluted cellular components. The diluted plasma flows from the separating chamber 228 into a second separating chamber 244 though a siphon 242, and cellular components are further separated in the second separating chamber 244.

Next, the diluted sample flows into a collection chamber 248 through a passage 246 and is transferred to cuvettes 250 to conduct an optical analysis. The cuvettes 250 contain a reagent necessary for the optical analysis of the sample. The dilution factor of the sample can be derived from the optical measurement value only of the diluent obtained by the foregoing technique and the optical measurement value of the diluted sample.

In some methods of the prior art, a biological fluid is electrochemically or optically analyzed using a microchip on which a micro-channel is formed. In an electrochemical analysis method, a biosensor for analyzing specific components in a sample liquid determines a blood sugar level and so on by, for example, measuring a current value obtained by a reaction of glucose in blood and a reagent such as glucose oxidase retained in the sensor.

In an analyzing method using a microchip, a fluid can be controlled using a rotator having a horizontal axis and it is possible to measure a sample liquid, separate cellular materials, transfer/distribute a separated fluid, and mix/stir a liquid by using a centrifugal force, thereby conducting various biochemical analyses.

FIG. 64 shows a centrifugal transfer biosensor 400 illustrated in Patent Document 6 and so on. The centrifugal transfer biosensor 400 can conduct a quantitative analysis simultaneously on multiple sample solutions introduced into a microchip. In this configuration, a sample solution is transferred from an inlet port 409 to an outlet port 410 by a capillary force and fills capillary channels 404a to 404f. After that, a centrifugal force generated by a rotation of the biosensor 400 distributes the sample liquid in the capillary channels through liquid branch points 406a to 406g arranged on the same circumference. Further, the sample liquid passes through small connecting conduits 407a to 407f and is transferred to the subsequent processing chamber (not shown).

Patent Document 1: National Publication of International Patent Application No. 4-504758
Patent Document 2: Japanese Patent Laid-Open No. 61-167469
Patent Document 3: National Publication of International Patent Application No. 5-508709
Patent Document 4: Japanese Patent Laid-Open No. 2005-345160
Patent Document 5: National Publication of International Patent Application No. 7-503794
Patent Document 6: National Publication of International Patent Application No. 2005-502031

DISCLOSURE OF THE INVENTION

Problems to be Solved by the Invention

In Patent Document 1, in order to prevent mixing of blood cell components, the plasma component 59a is drawn with the capillary cavity 61 separated from the bottom of the separating cavity 58 at a safe distance. However, variations in molding of the analyzing device 54 may vary the amount of a sample liquid collected in the first cavity 56, the surface height of a liquid retained in the separating cavity 58, the suction position of the capillary cavity 61, and the ratio of a plasma component in blood among individuals, thereby varying the amount of plasma in the sample liquid. Thus the position of a separation interface 63 of the plasma component 59a and the blood cell component 59b may be considerably changed. When the suction position of the capillary cavity 61 is set in consideration of these variations, the plasma component 59a remaining in the separating cavity 58 causes a liquid transfer loss 64. Hence, it is necessary to collect the sample liquid more than necessary, disadvantageously increasing a load on a patient.

The present invention has been devised to solve the problem of the prior art. An object of the present invention is to provide an analyzing device which can collect a required amount of a plasma component for an analysis from the minimum sample liquid, an analyzer using the same, and an analyzing method.

Further, in the configuration of the prior art shown in FIGS. 60 and 61, a centrifugal force is larger than a surface tension applied between a liquid and the wall surface of the measuring chamber during a rotation of the analyzing device. Thus a predetermined amount can be measured with a liquid level balanced at the opening position of the overflow port. However, when the rotation is slowed or stopped during a transition to the subsequent process, the liquid is released from the centrifugal force and a surface tension is simultaneously applied to the interface of the liquid and the wall surface of the overflow port. The surface tension causes the liquid to flow into the overflow chamber along the wall surface of the overflow port, so that precise measurements cannot be conducted. Further, since an outflow varies with liquid physical properties, it is necessary to change the size of the measuring chamber for each liquid to be analyzed.

In the configuration of the prior art shown in FIG. 62, centrifugal separation can be performed according to a difference in specific gravity but a capillary tube is directly connected to the retaining part to which blood is introduced. Hence, blood cells retained in the capillary tube before separation may be left in the capillary tube and mixed in blood serum/plasma to be collected.

The present invention has been devised to solve the problem of the prior art. An object of the present invention is to provide an analyzing device which can accurately collect only a required amount of a plasma component from a small amount of blood without mixing blood cells, and a blood separating method using the same.

In an optical analysis described in Patent Document 5, to be specific, in a measurement of the absorbance of visible light or ultraviolet light used in the analyzer of the prior art or the present invention, the measurement result is directly affected by an optical path length as evident from Lambert-Beer's law below:

$$A = \alpha \cdot L \cdot C$$

where $\alpha$ is an absorption coefficient, L is the thickness of a material (optical path length), and C is the concentration of a sample.

In other words, an error of an optical path length (manufacturing variation) directly appears as an error of a measurement value. As devices have been reduced in size with higher integration in response to a small amount of analyte, the optical path length has naturally decreased. The shorter the optical path length, the greater the influence of the error. However, it is substantially impossible to fabricate the system cuvettes 224 and 250 so as to completely eliminate the error of the optical path length. Thus the measurement value is inevitably affected by an error of the optical path length and the dilution factor cannot be accurately calculated.

The present invention has been devised to solve the problem of the prior art. An object of the present invention is to provide an analyzing method which can accurately calculate a dilution factor without being affected by an error of an optical path length, and an analyzing device having a channel configuration for implementing the analyzing method.

In Patent Document 6, when the plurality of liquid branch points are not arranged on the same circumference, the transfer of the sample solution by a centrifugal force is started from the channel with the shortest distance from the rotation axis to the liquid branch point of the capillary channel, so that quantification cannot be performed in the subsequent chamber.

The present invention has been devised to solve the problem of the prior art. An object of the present invention is to provide an analyzing device that can transfer a fixed amount to a measuring chamber even when the liquid branch points of a capillary channel are not arranged on the same circumference.

Means for Solving the Problems

An analyzing device of the present invention has a microchannel structure for transferring a sample liquid to a measurement spot by a centrifugal force, the analyzing device being used for reading in which a reaction liquid is accessed at the measurement spot, the analyzing device including: a separating cavity for separating the sample liquid into a solution component and a solid component by using the centrifugal force; a measurement channel for receiving and retaining a part of the solution component separated in the separating cavity; a connecting channel provided between the measurement channel and the separating cavity to transfer the sample liquid of the separating cavity; and a first capillary cavity provided on a side of the separating cavity so as to communicate with the connecting channel, the first capillary cavity being formed to extend to the outside of the separation interface of the sample liquid separated in the separating cavity.

The analyzing device further includes a connecting channel having a siphon structure communicating with the outermost periphery position of the separating cavity and bending inside the liquid level of the sample liquid retained in the separating cavity; and an overflow cavity located outside the outermost periphery position of the separating cavity and communicating with the separating cavity through the connecting channel.

The analyzing device further includes a second capillary cavity formed to communicate with the outer periphery position of the separating cavity, the second capillary cavity retaining a part of the separated solid component.

Further, the separating cavity has an interior divided into a plasma retaining part and a blood cell retaining part by a blood separating wall, and the component centrifugally separated from the sample liquid by applying the centrifugal force passes through a clearance of the blood separating wall and flows into the blood cell retaining part.

Moreover, the blood separating wall has a wall surface in contact with the blood cell retaining part, the wall surface being formed of a circular surface at a constant distance from a rotation center.

An analyzing method of the present invention using an analyzing device including: a separating cavity for separating a sample liquid into a solution component and a solid component by using the centrifugal force; a measurement channel for receiving and retaining a part of the solution component separated in the separating cavity; a connecting channel provided between the measurement channel and the separating cavity to transfer the sample liquid of the separating cavity; and a first capillary cavity provided on a side of the separating cavity so as to communicate with the connecting channel, the first capillary cavity being formed to extend to the outside of the separation interface of the sample liquid separated in the separating cavity, the analyzing method including: rotating the analyzing device to transfer the sample liquid spot-applied to the analyzing device to the separating cavity and centrifugally separate the sample liquid, stopping the rotation to suck the solution component of the centrifugally separated sample liquid firstly through the first capillary cavity, and transferring the solution component to the measurement channel through the connecting channel; rotating the analyzing device to transfer the solution component in the measurement channel and mix the solution component with a reagent; and accessing a reactant at the measurement spot when the measurement spot is located at a reading position.

An analyzing method of the present invention, when a diluent and a liquid sample are received and mixed in a mixing chamber of an analyzing device, a diluent sample stirred and mixed in the mixing chamber is transferred to a measuring chamber of the analyzing device, and a component is analyzed by accessing the reactant of the diluent sample in the measuring chamber, the analyzing method including: a first step of measuring the absorbance only of the diluent by passing detection light through the mixing chamber in a state in which only the diluent is retained in the mixing chamber; a second step of measuring the absorbance of the diluent sample by passing the detection light through the mixing chamber in a state in which the diluent sample is retained in the mixing chamber; and a third step of calculating a component analysis result by correcting a result read by accessing the reactant of the diluent sample in the measuring chamber, the result being corrected by a dilution factor determined based on the absorbances obtained in the first and second steps.

In the first step, the absorbance only of the diluent received by the mixing chamber is measured during the transfer of the diluent to the mixing chamber.

Further, the first step includes a measuring operation for measuring the diluent during the rotation of the analyzing device, and the diluent is transferred to the mixing chamber by slowing down the analyzing device after the completion of the measuring operation.

An analyzing device of the present invention includes: a diluent container storage part for storing a diluent; a capillary cavity configured to retain a fixed amount of a liquid sample; a liquid sample retaining chamber connected to the capillary cavity to temporarily retain the liquid sample; a diluent quantifying chamber connected to the diluent container storage part to quantify a required amount of the diluent; an overflow channel connected to the diluent quantifying chamber to cause an overflow of an excessive amount of the diluent transferred to the diluent quantifying chamber; a mixing chamber connected to the liquid sample retaining chamber via a first connecting channel and connected to the diluent quantifying chamber via a second connecting channel; and a measuring chamber connected to the mixing chamber via a capillary channel to receive a diluent sample obtained by stirring/mixing the diluent and the liquid sample in the mixing chamber.

Moreover, the overflow channel is connected to the mixing chamber.

The analyzing device further includes an overflow channel enabling a measurement by causing the liquid sample exceeding a predetermined amount to overflow into a separating cavity.

The diluent container storage part and the mixing chamber are connected via a distributing channel instead of the diluent quantifying chamber to distribute the diluent to the diluent quantifying chamber and the mixing chamber.

Further, the first connecting channel and the second connecting channel each have a siphon structure.

The analyzing device further includes an overflow chamber communicating with the mixing chamber through a third connecting channel having a siphon structure.

An analyzing device of the present invention is an analyzing device rotated about a rotation axis to distribute a sample liquid of a filling chamber to a plurality of measuring chambers, wherein the plurality of measuring chambers are arranged along the outer periphery side relative to the rotation axis, the analyzing device includes a quantifying capillary channel that has the proximal end connected to the filling chamber, is extended in a meandering manner between the rotation axis and the plurality of measuring chambers in the circumferential direction, and has joints for distributing the sample liquid to the plurality of measuring chambers with inflection points serving as liquid branch points on the inner periphery side, and in portions having the liquid branch points located at different distances from the rotation axis, a larger sectional area is provided on the channel of the joint with the measuring chamber for receiving the sample liquid from the liquid branch point at a shorter distance from the rotation axis as compared with the joint of a channel connected to the liquid branch point at a longer distance from the rotation axis and a channel connected to the liquid branch point at a shorter distance from the rotation axis.

The joint of the quantifying part and the chamber has an area expressed by a length obtained by adding a length to one of the channel width and the thickness of the joint of the quantifying parts, the added length being expressed as follows:

$$X=\gamma/(m \cdot r \cdot \omega^2/S)$$

where X is a length for expansion, m is a molecular mass, r is a radius of gyration, ω is the number of revolutions, S is a sectional area, and γ is a surface tension.

Further, hydrophilic treatment is performed on the wall surfaces of the channels and the measuring chambers.

Advantage of the Invention

According to an analyzing device and an analyzing method using the same of the present invention, it is possible to collect a required amount of a plasma component for analysis from the minimum sample liquid, thereby reducing a load of a patient and forming a cavity necessary for analysis with the minimum fluid volume. Hence, the size of the analyzing device can be reduced.

According to the analyzing device and a centrifugal separation method using the same of the present invention, it is possible to collect the maximum amount of the plasma component contained in a small amount of blood, without mixing a blood cell component with the plasma component.

According to the analyzing method of the present invention, it is possible to accurately calculate a dilution factor without being affected by variations in an optical path length among measuring chambers, achieving an analysis with high accuracy.

According to the analyzing device of the present invention, even when the liquid branch points of a capillary channel are located at different distances from a rotation axis, a sample liquid quantified in a quantifying capillary channel can be transferred into the chamber.

BRIEF DESCRIPTION OF THE DRAWINGS

FIG. 12 is a sectional view showing a state after the analyzing device is set on the analyzer and is rotated and a state after centrifugal separation;

FIG. 38A is an enlarged perspective view showing a capillary cavity 33a and a portion around the capillary cavity 33a;

BEST MODE FOR CARRYING OUT THE INVENTION

Referring to FIGS. 1A and 1B to 19, embodiments of an analyzing device of the present invention will be described below.

First Embodiment

FIGS. 1A and 1B to 6 show an analyzing device.

Figure 1A:
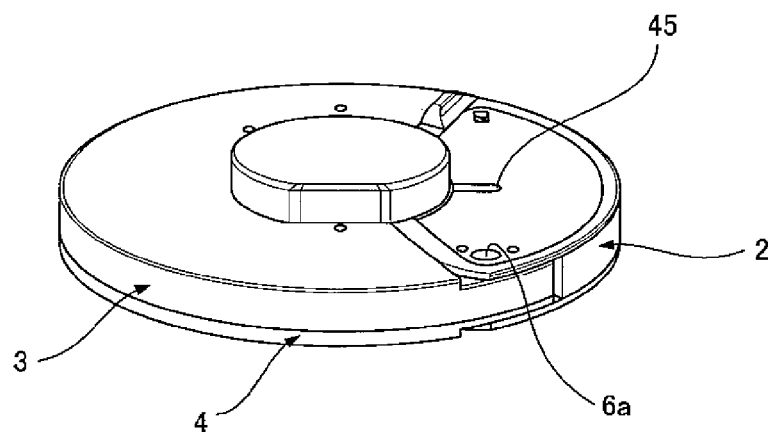
FIG. 1A is an external perspective view showing an analyzing device with an opened/closed protective cap according to an embodiment of the present invention.
Figure 1B:
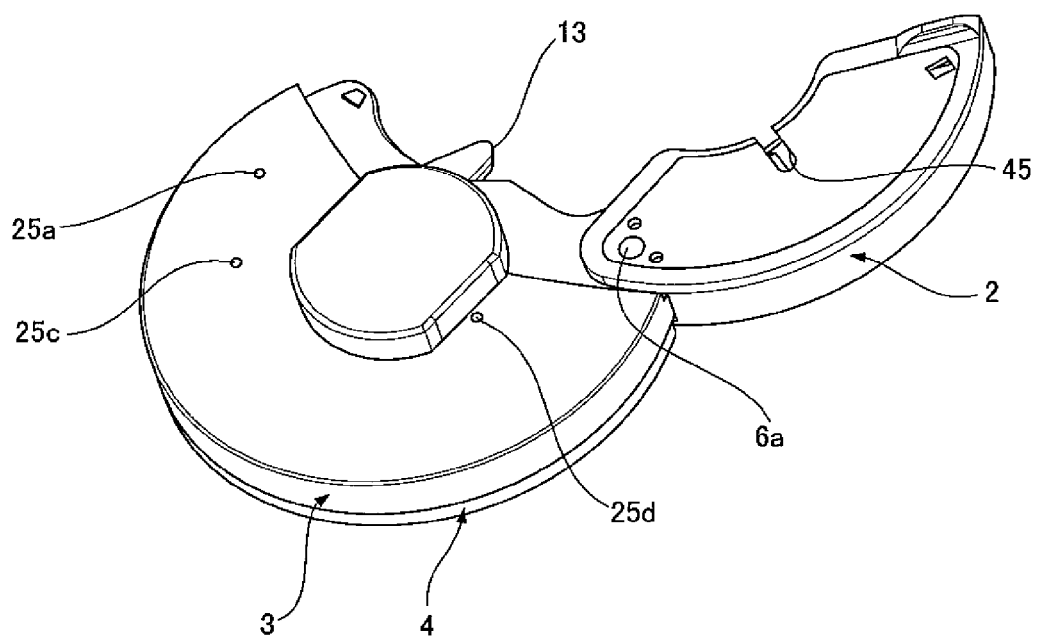
FIG. 1B is an external perspective view showing the analyzing device with the opened/closed protective cap according to the embodiment of the present invention.
Figure 2:
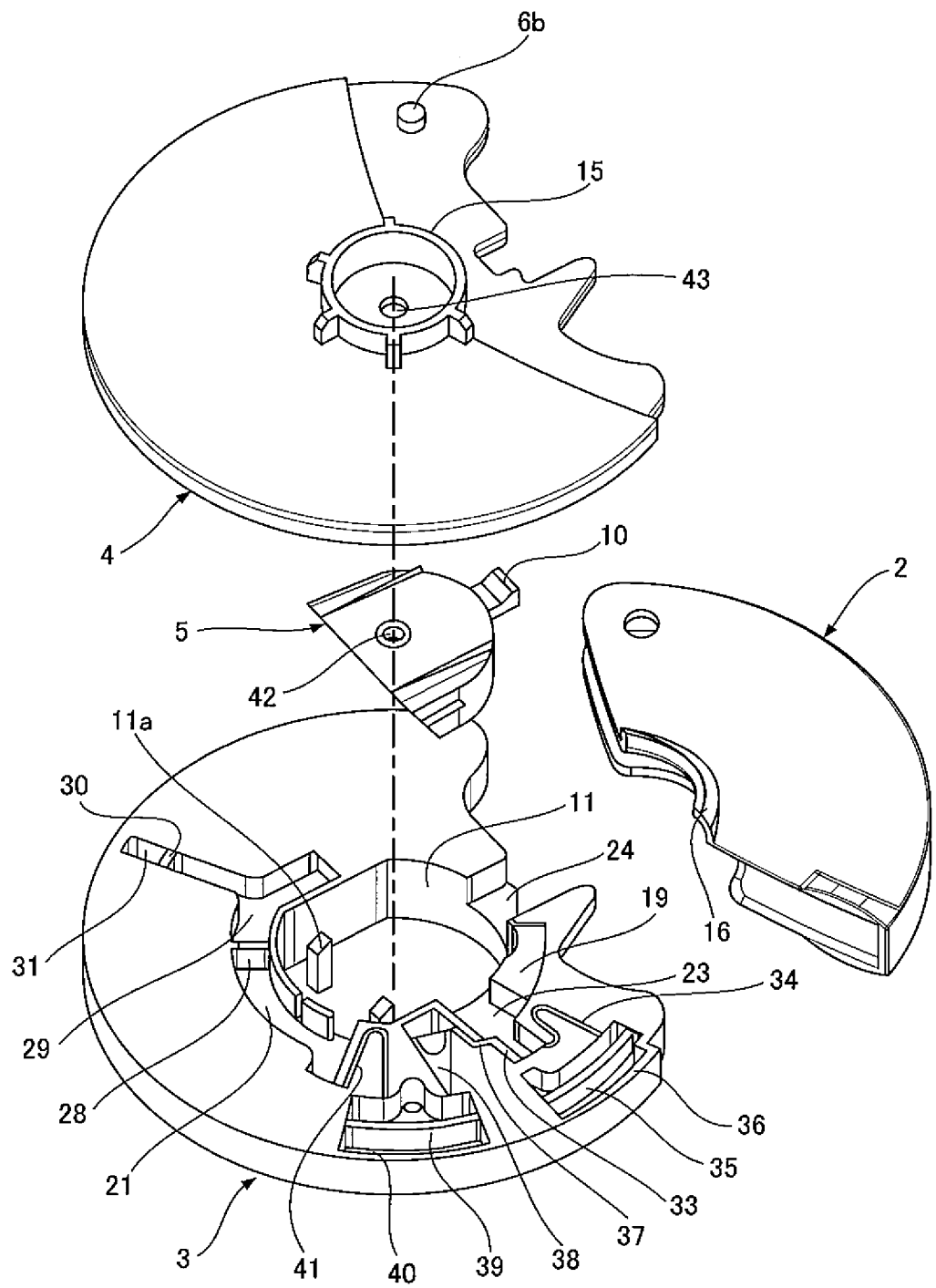
FIG. 2 is an exploded perspective view showing the analyzing device according to the embodiment.
Figure 3:
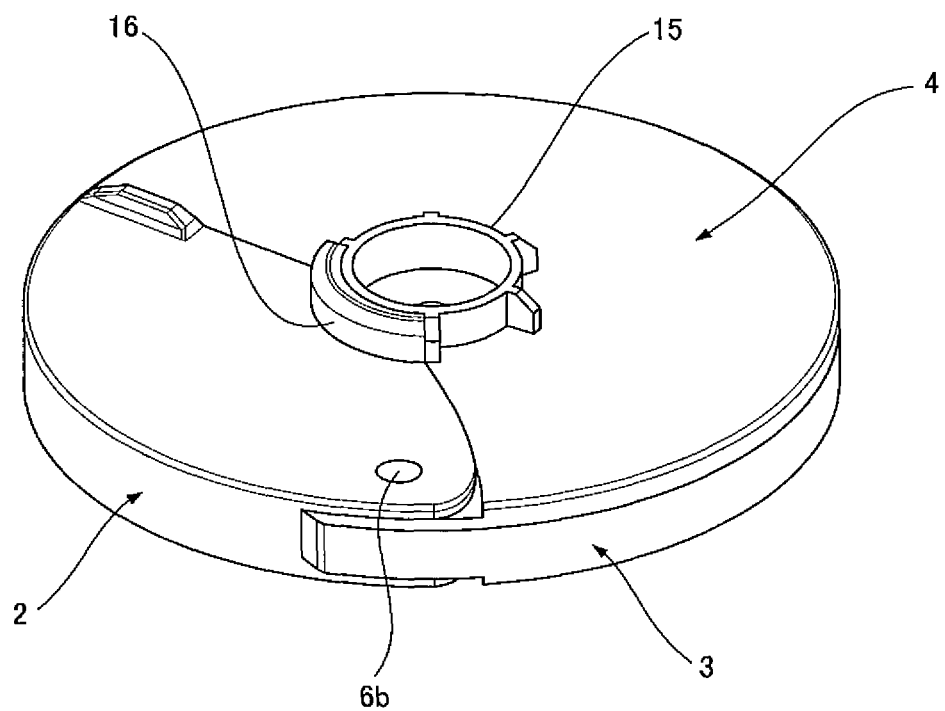
FIG. 3 is a rear perspective view showing the analyzing device with the closed protective cap.

FIGS. 1A and 1B show an analyzing device 1 with a protective cap 2 closed and opened. FIG. 2 shows the disassembled analyzing device 1 with the underside of FIG. 1A placed face up. FIG. 3 is an assembly drawing of FIG. 2.

As shown in FIGS. 1A, 1B, and 2, the analyzing device 1 is made up of four components of a base substrate 3 having a microchannel structure formed on one surface, the microchannel structure having a minutely uneven surface, a cover substrate 4 for covering the surface of the base substrate 3, a diluent container 5 for retaining a diluent, and the protective cap 2 for preventing splashes of a sample liquid.

The base substrate 3 and the cover substrate 4 are joined to each other with the diluent container 5 and so on set in the base substrate 3 and the cover substrate 4, and the protective cap 2 is attached to the joined base substrate 3 and cover substrate 4.

The cover substrate 4 covers the openings of several recessed portions formed on the top surface of the base substrate 3, thereby forming a plurality of storage areas described later (the same as measurement spots described later), the channels of the microchannel structure for connecting the storage areas, and so on. Necessary ones of the storage areas are filled beforehand with reagents necessary for various analyses. One side of the protective cap 2 is pivotally supported such that the protective cap 2 can be opened and closed in engagement with shafts 6a and 6b formed on the base substrate 3 and the cover substrate 4. When a sample liquid to be inspected is blood, the channels of the microchannel structure in which a capillary force is applied have clearances of 50 μm to 300 μm.

The outline of an analyzing process using the analyzing device 1 is that a sample liquid is dropped into the analyzing device 1 in which the diluent has been set, at least a part of the sample liquid is diluted with the diluent, and then a measurement is conducted.

Figure 4:
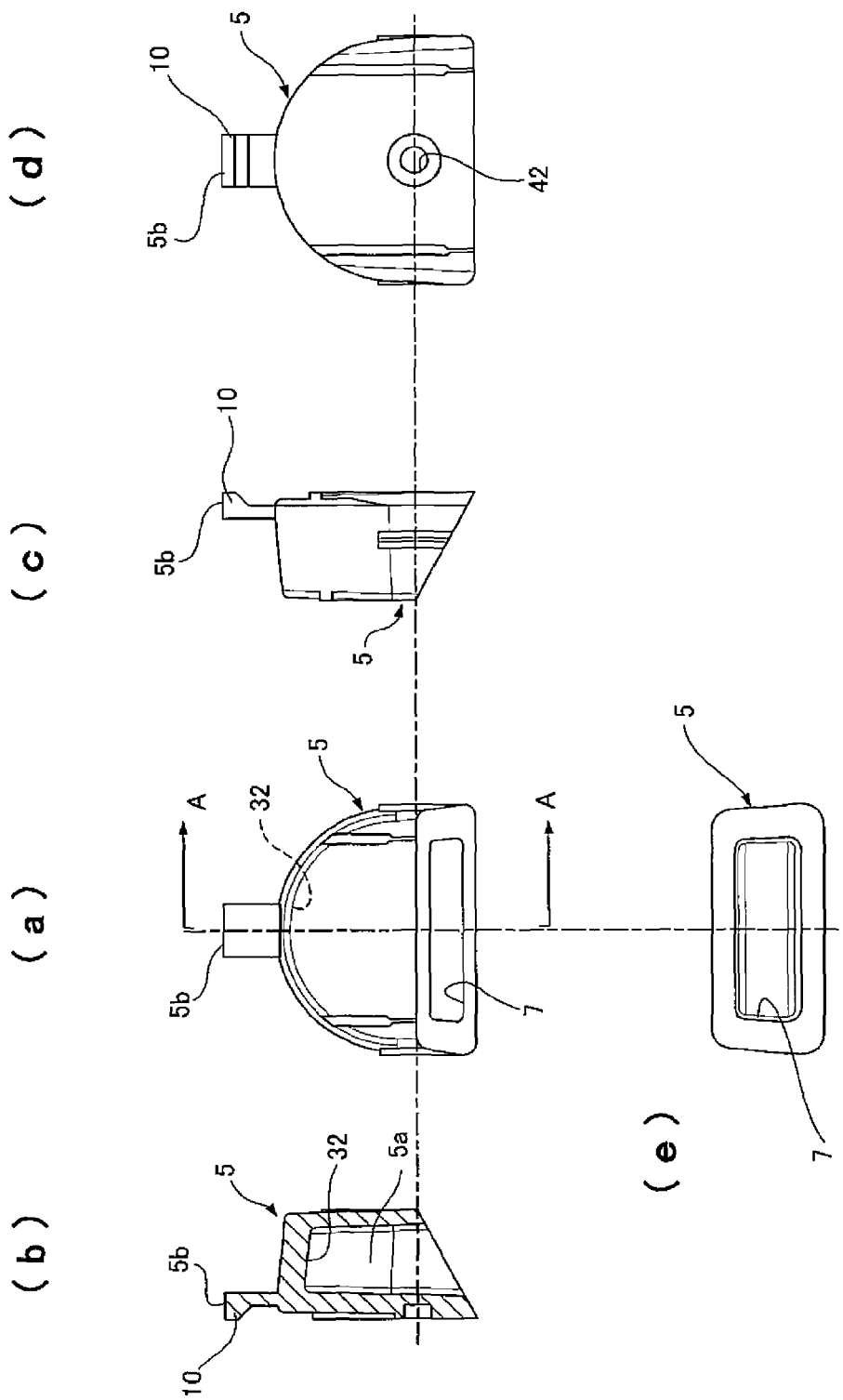
FIG. 4 is an explanatory drawing showing a diluent container according to the embodiment.

FIG. 4 shows the shape of the diluent container 5.

FIG. 4(a) is a plan view, FIG. 4(b) is an A-A sectional view of FIG. 4(a), FIG. 4(c) is a side view, FIG. 4(d) is a rear view, and FIG. 4(e) is a front view taken from an opening 7. After an interior 5a of the diluent container 5 is filled with a diluent 8 as shown in FIG. 6(a), the opening 7 is enclosed with an aluminum seal 9 serving as a sealing member. On the opposite side of the diluent container 5 from the opening 7, a latch portion 10 is formed. The diluent container 5 is set in a diluent container storage part 11 formed between the base substrate 3 and the cover substrate 4, and is stored movably between a liquid retaining position shown in FIG. 6(a) and a liquid discharging position shown in FIG. 6(c).

Figure 5:
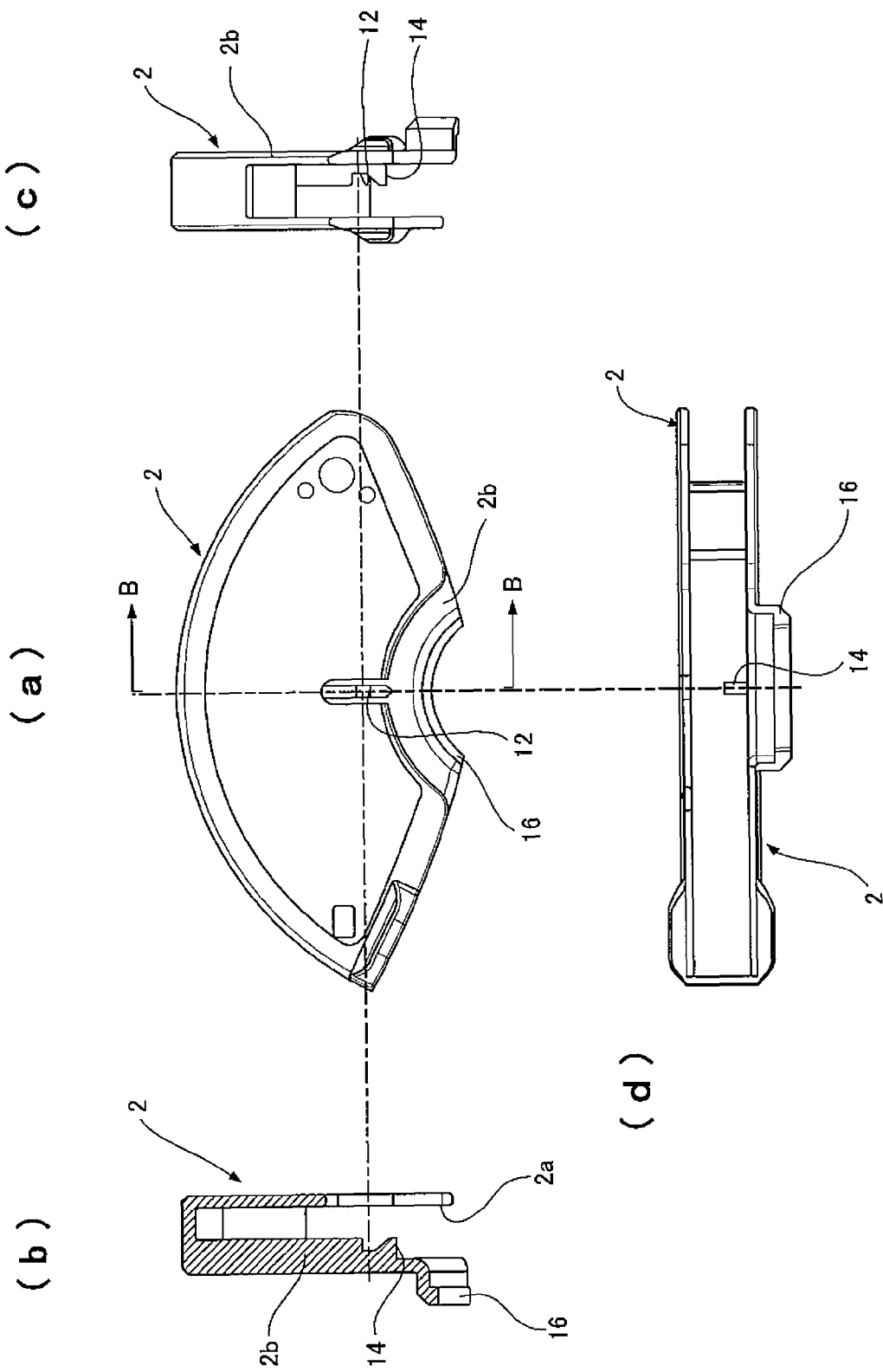
FIG. 5 is an explanatory drawing showing the protective cap according to the embodiment.
Figure 6:
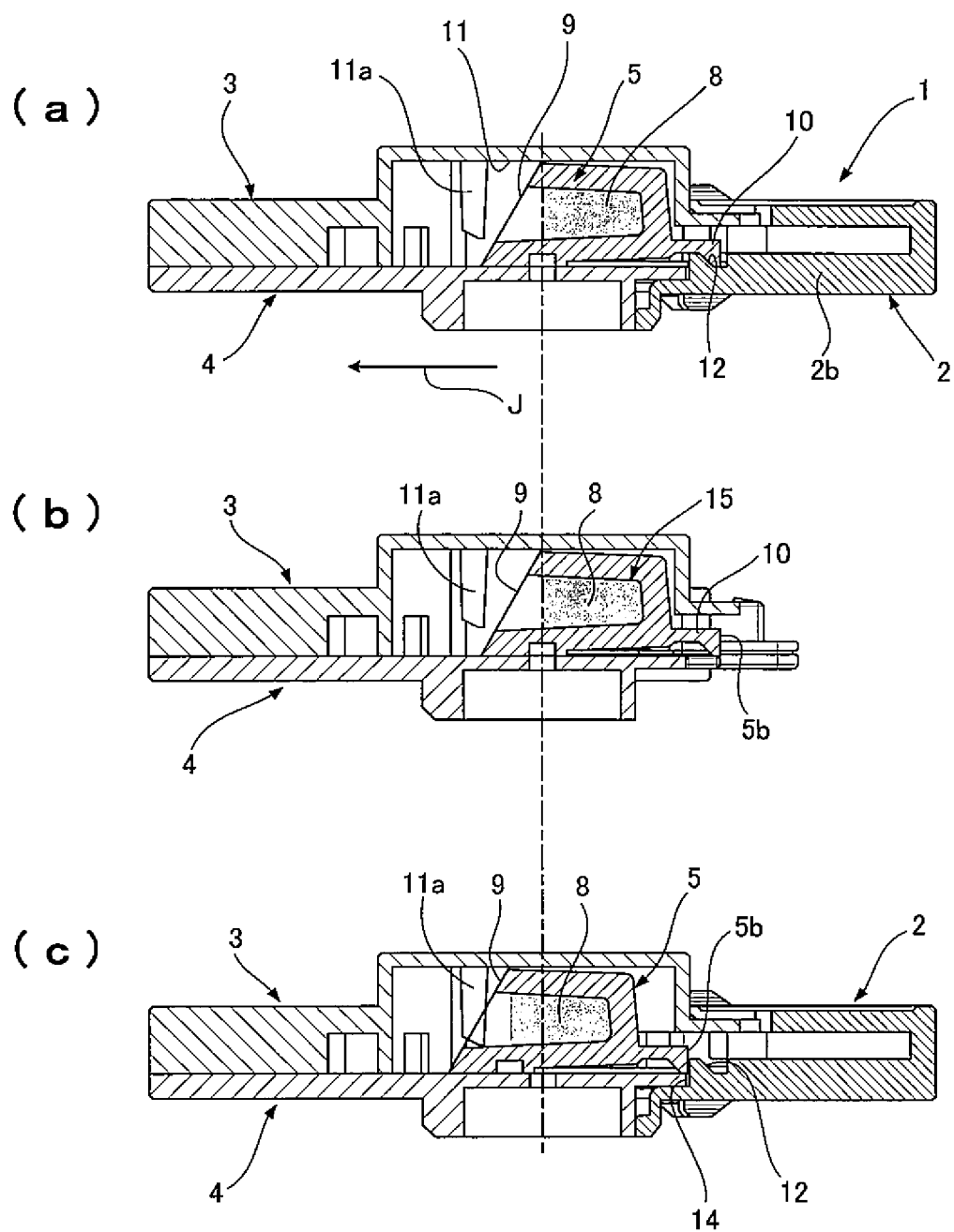
FIG. 6 is a sectional view showing a state before the analyzing device is used, a state when a sample liquid is dropped, and a state after the sample liquid is dropped and the protective cap is closed.

FIG. 5 shows the shape of the protective cap 2.

FIG. 5(a) is a plan view, FIG. 5(b) is a B-B sectional view of FIG. 5(a), FIG. 5(c) is a side view, FIG. 5(d) is a rear view, and FIG. 5(e) is a front view taken from an opening 2a. In the protective cap 2, a locking groove 12 is formed. In the closed state of FIG. 1A, the latch portion 10 of the diluent container 5 can be engaged with the locking groove 12 as shown in FIG. 6(a).

FIG. 6(a) shows the analyzing device 1 before use. In this state, the protective cap 2 is closed and the latch portion 10 of the diluent container 5 is engaged with the locking groove 12 of the protective cap 2 to lock the diluent container 5 at the liquid retaining position, so that the diluent container 5 does not move in the direction of arrow J. In this state, the analyzing device 1 is supplied to a user.

When the sample liquid is dropped, the protective cap 2 is opened as shown in FIG. 1B against the engagement with the latch portion 10 in FIG. 6(a). At this point, a bottom 2b of the protective cap 2 is elastically deformed with the locking groove 12 formed on the bottom 2b, thereby disengaging the latch portion 10 of the diluent container 5 from the locking groove 12 of the protective cap 2 as shown in FIG. 6(b).

In this state, the sample liquid is dropped to an exposed inlet 13 of the analyzing device 1 and then the protective cap 2 is closed. At this point, by closing the protective cap 2, a wall surface 14 forming the locking groove 12 comes into contact with a surface 5b of the latch portion 10 of the diluent container 5 on the side of the protective cap 2, and the wall surface 14 presses the diluent container 5 in the direction of arrow J (a direction that comes close to the liquid discharging position). The diluent container storage part 11 has an opening rib 11a formed therein as a portion protruding from the side of the base substrate 3. When the diluent container 5 is pressed by the protective cap 2, the aluminum seal 9 provided on the inclined seal face of the opening 7 of the diluent container 5 is collided with and broken by the opening rib 11a as shown in FIG. 6(c).

Figure 7:
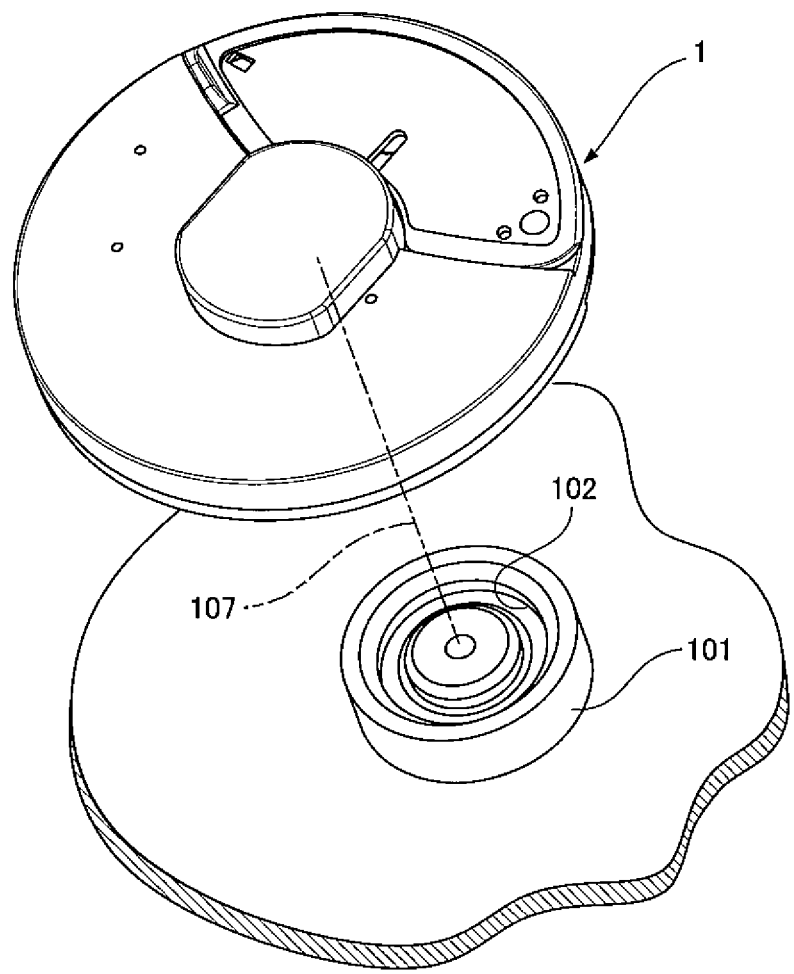
FIG. 7 is a perspective view showing a state immediately before the analyzing device is set on an analyzer.
Figure 8:
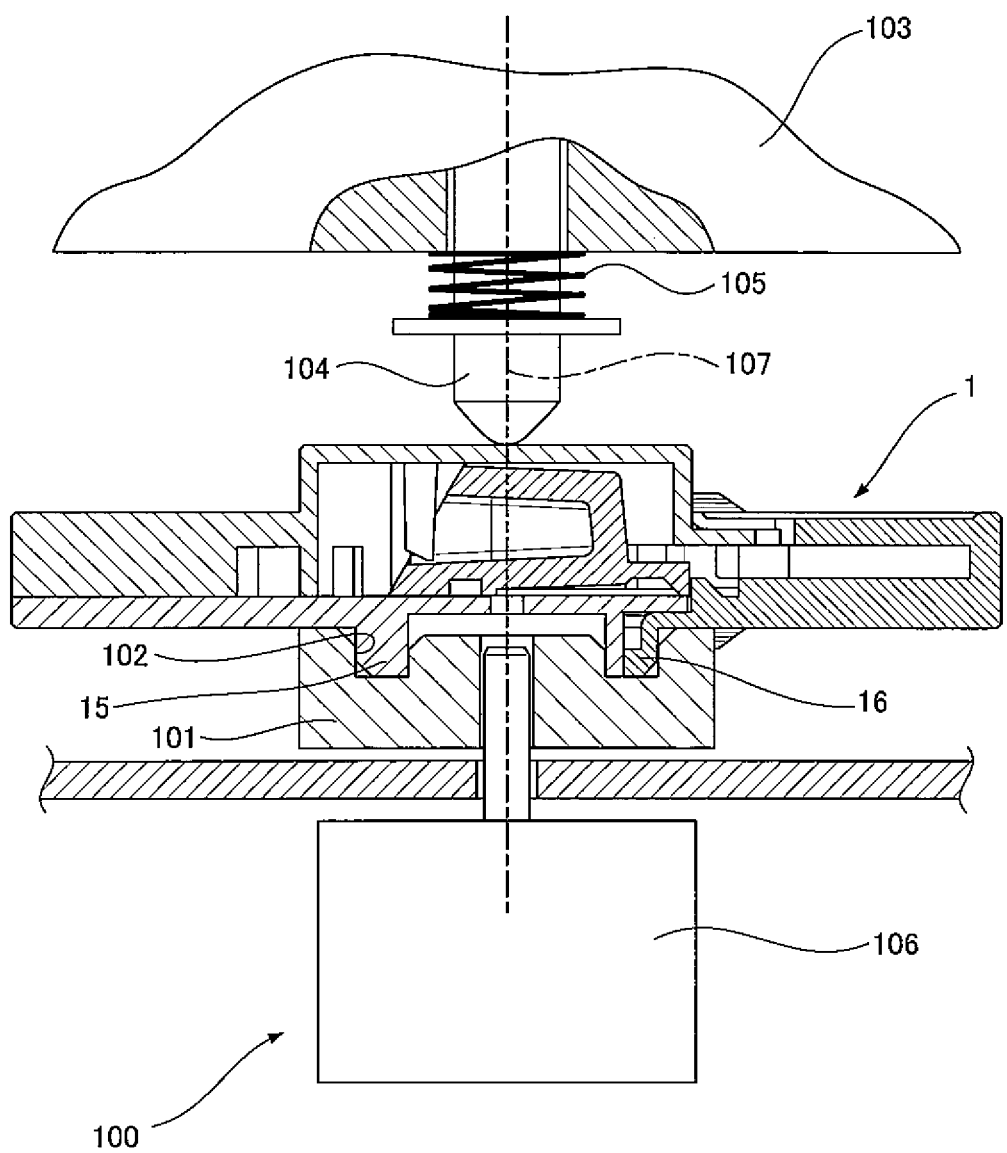
FIG. 8 is a sectional view showing a state in which the analyzing device is set on the analyzer.

As shown in FIGS. 7 and 8, the analyzing device 1 is set on a rotor 101 of an analyzer 100 with the cover substrate 4 placed on the underside of the analyzing device 1, so that a component of the sample liquid can be analyzed.

On the top surface of the rotor 101, a groove 102 is formed. In a state in which the analyzing device 1 is set on the rotor 101, a rotary support part 15 formed on the cover substrate 4 of the analyzing device 1 and a rotary support part 16 formed on the protective cap 2 are engaged with the groove 102, so that the analyzing device 1 is stored.

After the analyzing device 1 is set on the rotor 101, a door 103 of the analyzer is closed before a rotation of the rotor 101, so that the set analyzing device 1 is pressed to the side of the rotor 101 by a movable piece 104 provided on the side of the door 103, by a biasing force of a spring 105 at a position on the rotation axis of the rotor 101. Thus the analyzing device 1 rotates together with the rotor 101 that is rotationally driven by a rotational drive 106. Reference numeral 107 denotes the axis of rotation of the rotor 101. The protective cap 2 is attached to prevent the sample liquid deposited around the inlet 13 from being splashed to the outside by a centrifugal force during an analysis.

The components constituting the analyzing device 1 are desirably made of resin materials enabling low material cost with high mass productivity. The analyzer 100 analyzes the sample liquid according to an optical measurement method for measuring light passing through the analyzing device 1. Thus the base substrate 3 and the cover substrate 4 are desirably made of transparent synthetic resins including PC, PMMA, AS, and MS.

The diluent container 5 is desirably made of crystalline synthetic resins such as PP and PE that have low moisture permeability. This is because the diluent container 5 has to contain the diluent 8 for a long period. The protective cap 2 may be made of any materials as long as high moldability is obtained. Inexpensive resins such as PP and PE are desirable.

The base substrate 3 and the cover substrate 4 are desirably joined to each other according to a method hardly affecting the reaction activity of a reagent retained in the storage area. Thus ultrasonic welding, laser welding, and so on are desirable because reactive gas and solvent are hardly generated during joining.

On a portion where a solution is transferred by a capillary force in a small clearance between the base substrate 3 and the cover substrate 4 that are joined to each other, hydrophilic treatment is performed to increase the capillary force. To be specific, hydrophilic treatment is performed using a hydrophilic polymer, a surface-active agent, and so on. In this case, hydrophilicity means a contact angle of less than 90° relative to water. More preferably, the contact angle is less than 40°.

Figure 9:
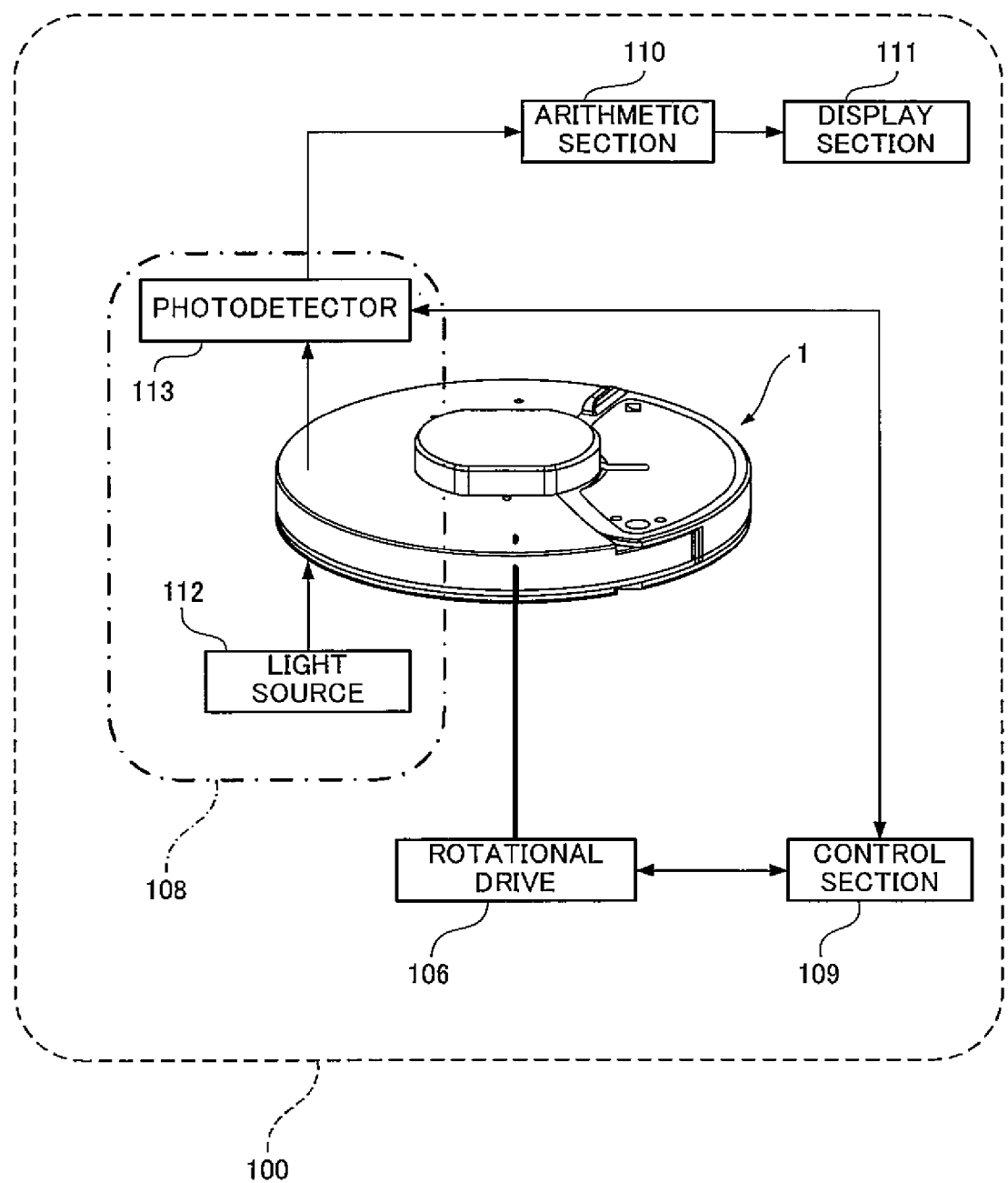
FIG. 9 is a structural diagram showing the analyzer of the embodiment.

FIG. 9 shows the configuration of the analyzer 100.

The analyzer 100 is made up of the rotational drive 106 for rotating the rotor 101, an optical measurement section 108 for optically measuring a solution in the analyzing device 1, a control section 109 for controlling the rotation speed and direction of the rotor 101, the measurement timing of the optical measurement section, and so on, an arithmetic section 110 for calculating a measurement result by processing a signal obtained by the optical measurement section 108, and a display section 111 for displaying the result obtained by the arithmetic section 110.

The rotational drive 106 can rotate the analyzing device 1 through the rotor 101 about the rotation axis 107 in any direction at a predetermined rotation speed and can further vibrate the analyzing device 1 so as to laterally reciprocate the analyzing device 1 at a predetermined stop position with respect to the rotation axis 107 with a predetermined amplitude range and a predetermined period.

The optical measurement section 108 includes a light source 112 for emitting light to the measuring part of the analyzing device 1, and a photodetector 113 for detecting an amount of light having passed through the analyzing device 1 out of light emitted from the light source 112.

The analyzing device 1 is rotationally driven by the rotor 101, and the sample liquid drawn into the analyzing device 1 from the inlet 13 is transferred in the analyzing device 1 by using a centrifugal force generated by rotating the analyzing device 1 about the rotation axis 107 located inside the inlet 13 and the capillary force of a capillary channel provided in the analyzing device 1. The microchannel structure of the analyzing device 1 will be specifically described below along with the analyzing process.

Figure 10A:
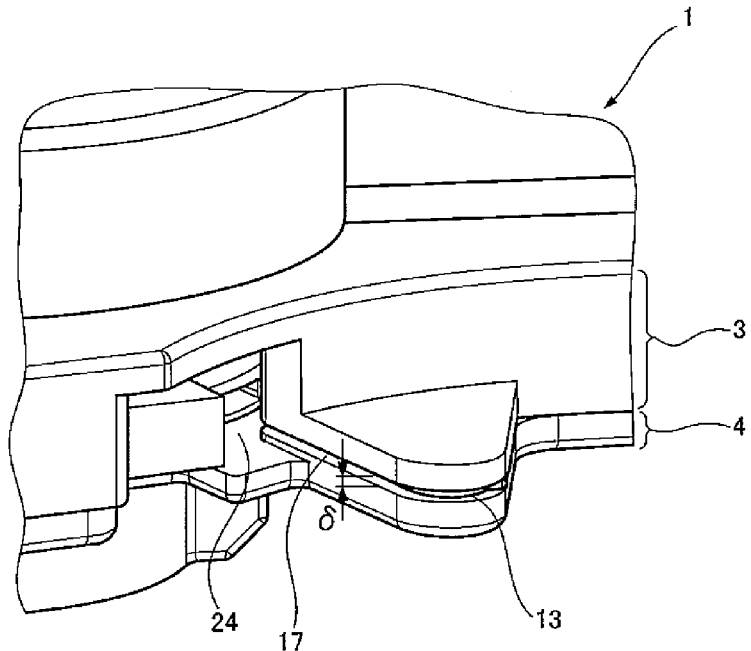
FIG. 10A is an enlarged external view showing an inlet 13 of the analyzing device from the outside of the analyzing device 1 according to the embodiment.
Figure 10B:
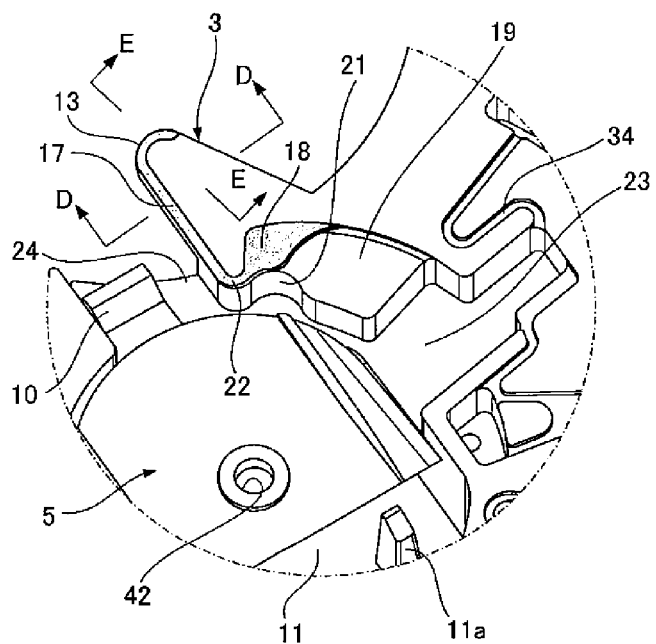
FIG. 10B is a perspective view showing the main part of the analyzing device from the side of a rotor 101 through a cover substrate 4 according to the embodiment.
Figure 10C:
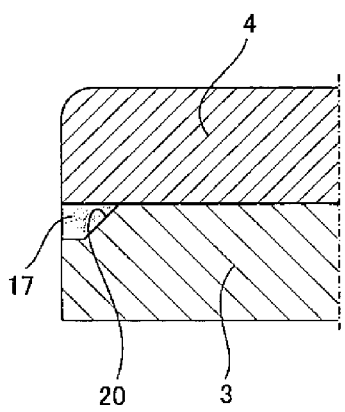
FIG. 10C is a D-D sectional view showing the main part of the analyzing device according to the embodiment.

FIGS. 10A, 10B and 10C show a portion around the inlet 13 of the analyzing device 1.

FIG. 10A is an enlarged view showing the inlet 13 from the outside of the analyzing device 1. FIG. 10B shows the microchannel structure from the side of the rotor 101 through the cover substrate 4.

The inlet 13 is connected to a capillary cavity 19 through a guide portion 17 with a small clearance 8 formed between the base substrate 3 and the cover substrate 4 to receive a capillary force. The capillary cavity 19 has a capacity large enough to retain a required amount of a sample liquid 18 with a clearance that receives a capillary force as in the guide portion 17. The cross section of the guide portion 17 (cross section D-D in FIG. 10B) in an orthogonal direction to a flow direction shows that the rear of the guide portion 17 is not an upright rectangle. As shown in FIG. 10C, the guide portion 17 is formed of an inclined plane 20 having the rear end gradually narrowing toward the cover substrate 4. On the joint of the guide portion 17 and the capillary cavity 19, a bending portion 22 is formed for changing the direction of a passage with a recessed portion 21 formed on the base substrate 3.

When viewed from the guide portion 17, a separating cavity 23 having a clearance not large enough to receive a capillary force is formed behind the capillary cavity 19. On a part of the sides of the capillary cavity 19, the bending portion 22, and the guide portion 17, a cavity 24 is formed which has one end connected to the separating cavity 23 and the other end opened to the atmosphere.

Figure 11:
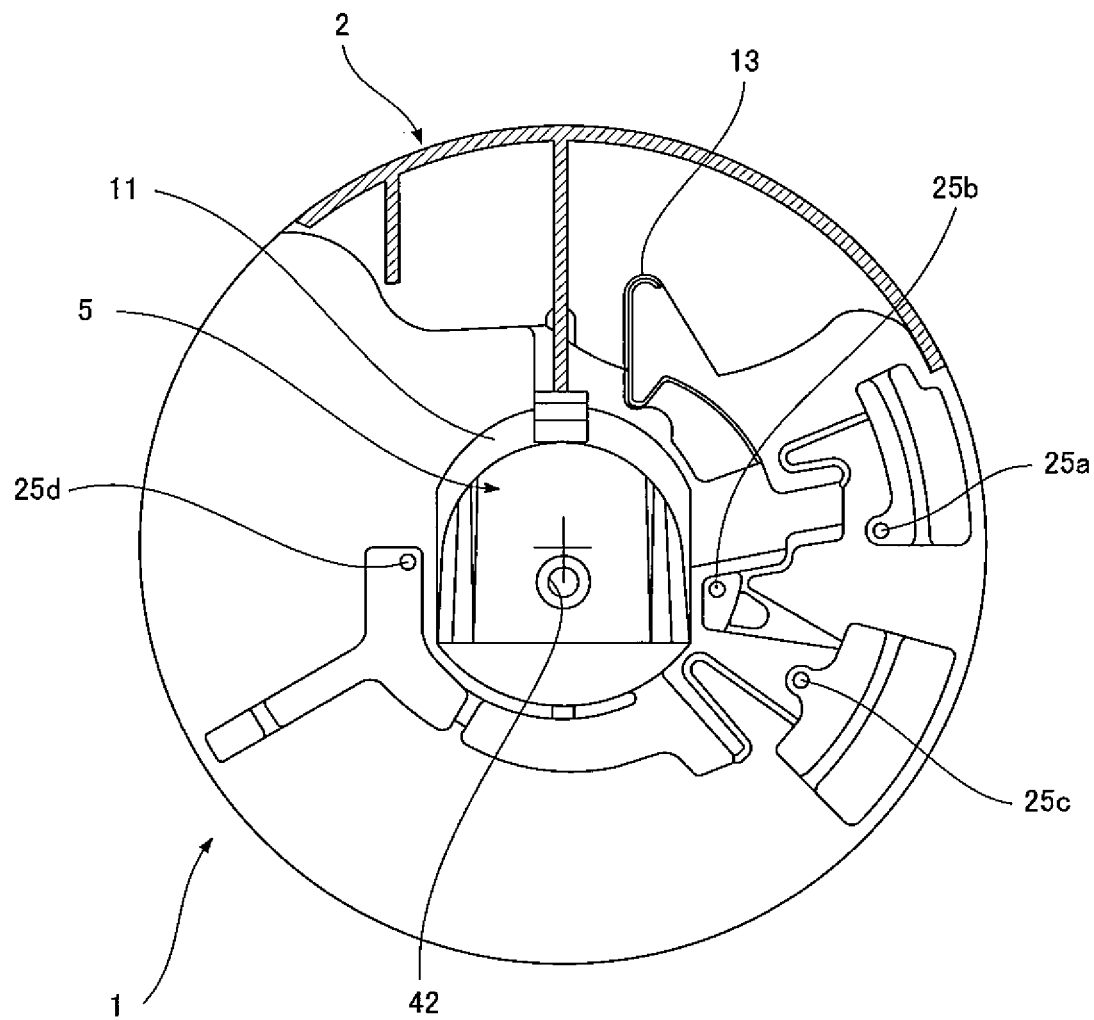
FIG. 11 is a sectional view showing that the analyzing device is set on the analyzer before a rotation is started.

With this configuration, the sample liquid 18 dropped to the inlet 13 is drawn to the capillary cavity 19 through the guide portion 17. FIG. 11 shows a state before the analyzing device 1 containing the dropped sample liquid 18 is set on the rotor 101 and is rotated thereon. At this point, as shown in FIG. 6(c), the aluminum seal 9 of the diluent container 5 has been collided with and broken by the opening rib 11a. Reference characters 25a, 25b, 25c, and 25d denote air holes formed on the base substrate 3.

Step 1

As shown in FIG. 12(a), the analyzing device 1 is set on the rotor 101 in a state in which the sample liquid is retained in the capillary cavity 19 and the aluminum seal 9 of the diluent container 5 has been broken.

Step 2

Figure 15A:
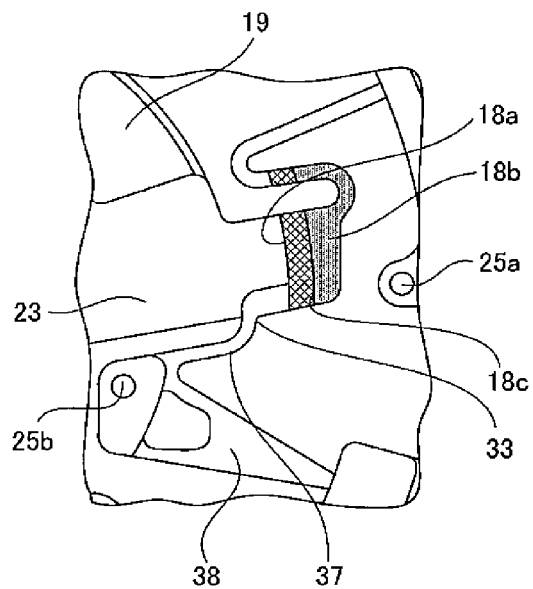
FIG. 15A is an enlarged view of a main part.

The door 103 is closed and then the rotor 101 is rotationally driven in a clockwise direction (direction C2), so that the retained sample liquid overflows at the position of the bending portion 22. The sample liquid in the guide portion 17 is discharged into the protective cap 2, and the sample liquid 18 in the capillary cavity 19 flows into the separating cavity 23 as shown in FIGS. 12(b) and 15A and is centrifugally separated into a plasma component 18a and a blood cell component 18b in the separating cavity 23. The diluent 8 from the diluent container 5 flows into a retaining cavity 27 through discharging channels 26a and 26b. When the diluent 8 having flowed into the retaining cavity 27 exceeds a predetermined amount, the excessive diluent 8 flows into an overflow cavity 29 through an overflow channel 28 and then flows into a reference measuring chamber 31 through a rib 30 for preventing backflow.

Figure 13:
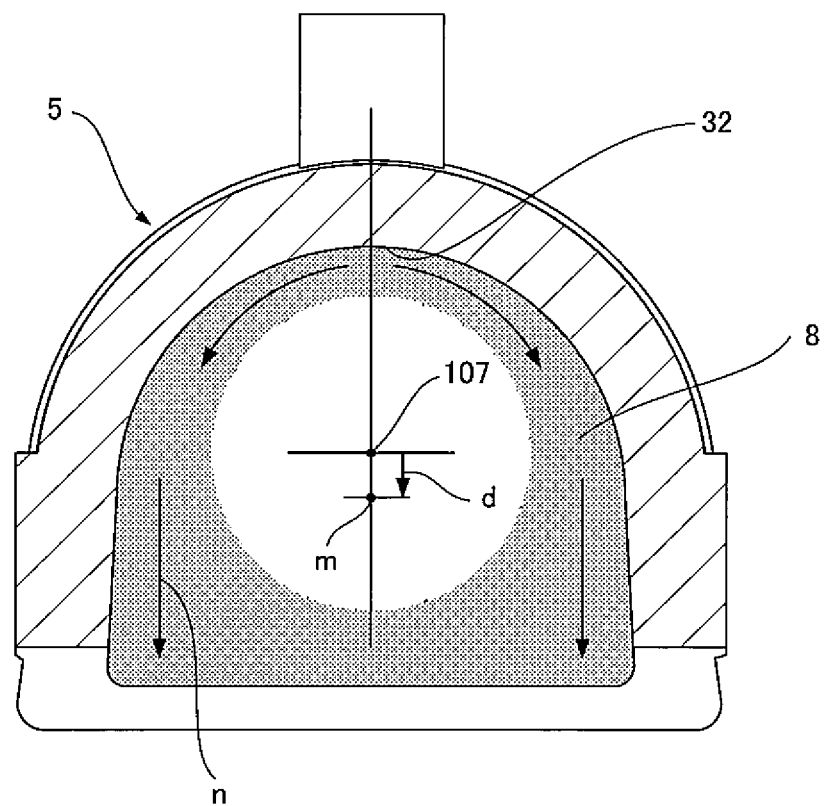
FIG. 13 is a sectional view showing the rotation axis of the analyzing device and the position of the diluent container when a diluent is discharged from the diluent container.
Figure 14:
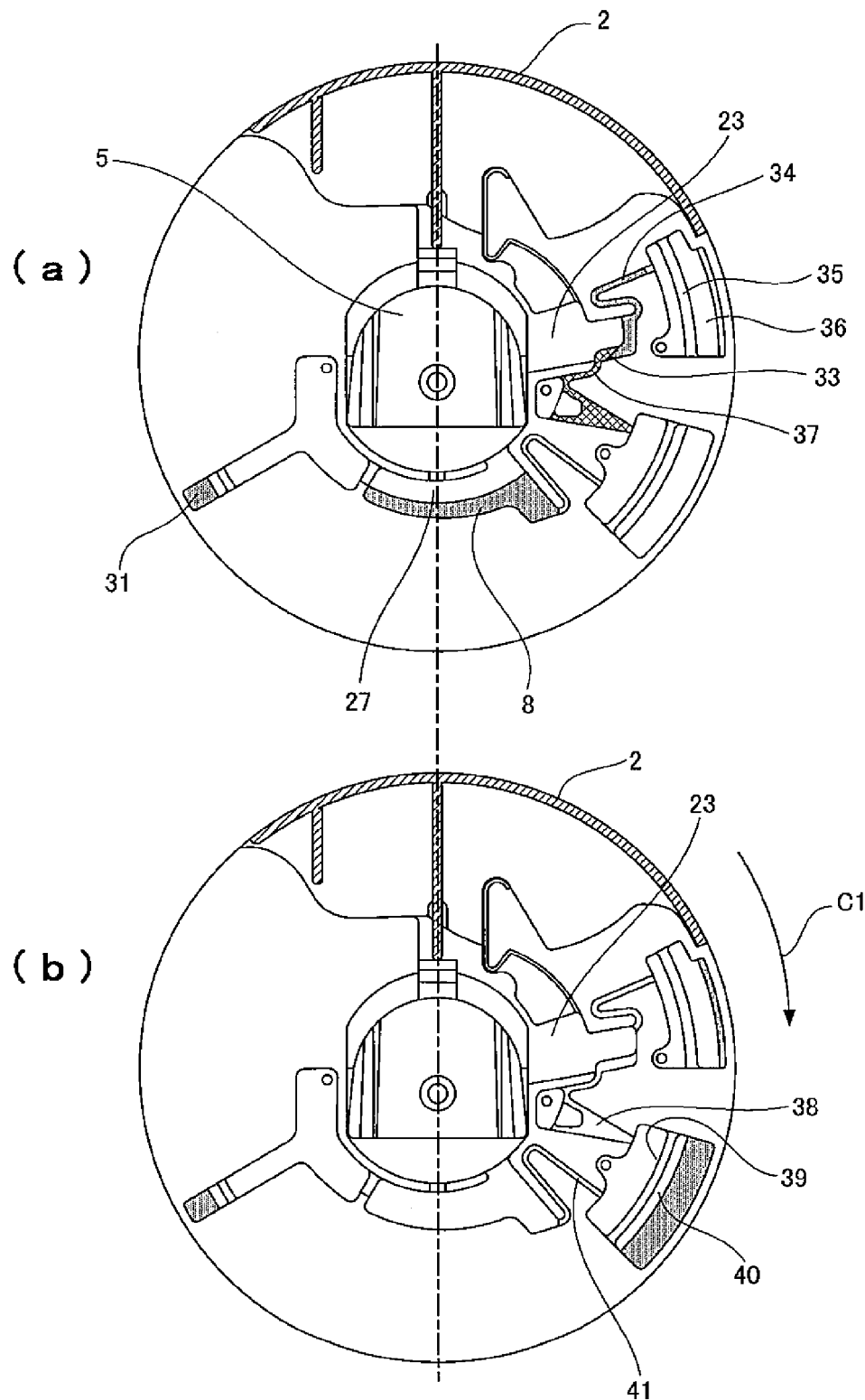
FIG. 14 is a sectional view showing a state when a solid component of the sample liquid is quantitatively collected and diluted after centrifugal separation.

As shown in FIGS. 4(a) and 4(b), a bottom of the diluent container 5 on the opposite side from the opening 7 sealed with the aluminum seal 9 is formed of a circular surface 32. At the liquid discharging position of the diluent container 5 in the state of FIG. 12(b), a center m of the circular surface 32 is offset, as shown in FIG. 13, by a distance d from the rotation axis 107 to the side of the discharging channel 26b. The diluent 8 having flowed to the circular surface 32 is changed to a flow (arrow n) directed from the outside to the opening 7 along the circular surface 32, and the diluent 8 is efficiently discharged to the diluent container storage part 11 from the opening 7 of the diluent container 5.

Step 3

Figure 15B:
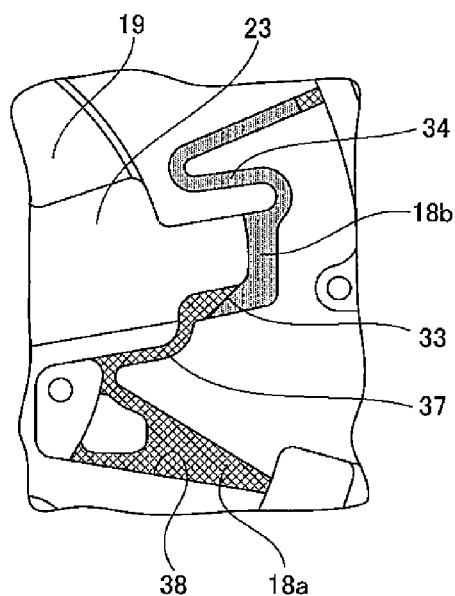
FIG. 15B is an enlarged view of the main part.
Figure 15C:
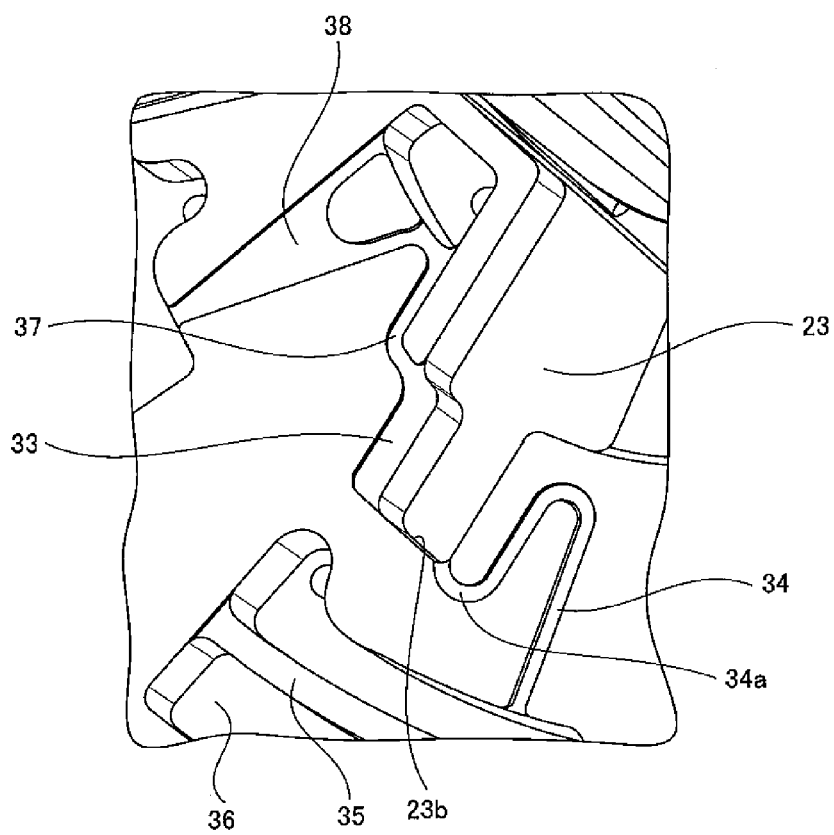
FIG. 15C is a perspective view showing the main part.
Figure 19:
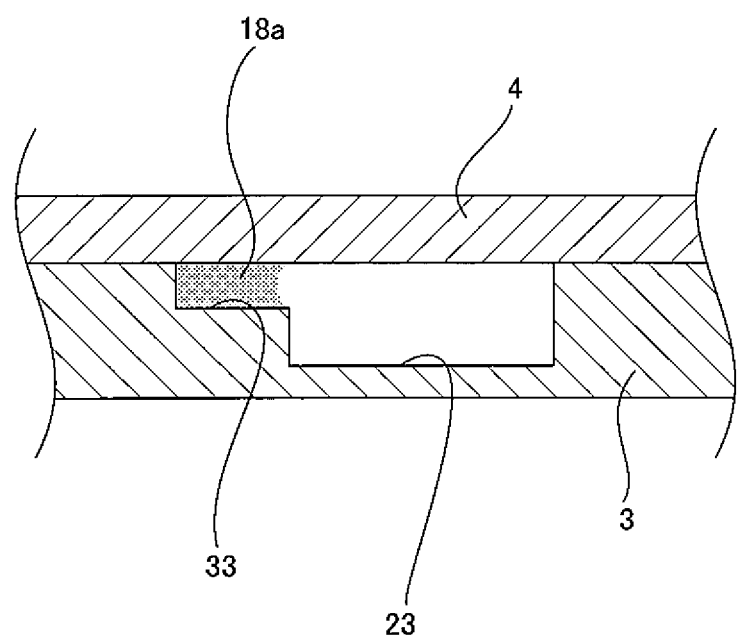
FIG. 19 is an E-E sectional view of FIG. 15C.

Next, when the rotation of the rotor 101 is stopped, the plasma component 18a is sucked into a capillary cavity 33 formed on the wall surface of the separating cavity 23 and flows into a measurement channel 38, as shown in FIGS. 14(a) and 15B, through a capillary channel 37 communicating with the capillary cavity 33, so that a fixed amount of the plasma component 18a is retained. FIG. 15C is a perspective view showing the capillary cavity 33 and a portion around the capillary cavity 33. FIG. 19 is an E-E sectional view of FIG. 15C.

Step 4

When the rotor 101 is rotationally driven in a counterclockwise direction (direction C1), as shown in FIG. 14(b), the plasma component 18a retained in the measurement channel 38 flows into a measuring chamber 40 through a rib 39 for preventing backflow. Further, the diluent 8 of the retaining cavity 27 flows into the measuring chamber 40 through a siphon-shaped connecting channel 41 and the rib 39 for preventing backflow. Moreover, the sample liquid in the separating cavity 23 flows into an overflow cavity 36 through a siphon-shaped connecting channel 34 and a rib 35 for preventing backflow. The rotor 101 is reciprocated and vibrated in the counterclockwise direction (direction C1) and the clockwise direction (direction C2) as necessary, thereby stirring the reagent retained in the measuring chamber and a solution to be measured, the solution being made up of the diluent 8 and the plasma component 18a.

Step 5

The rotor 101 is rotated in the counterclockwise direction (direction C1) or the clockwise direction (direction C2). When the measurement spot of the reference measuring chamber 31 passes between the light source 112 and the photodetector 113, the arithmetic section 110 reads a detected value of the photodetector 113 and determines a reference value. Moreover, when the measurement spot of the measuring chamber 40 passes between the light source 112 and the photodetector 113, the arithmetic section 110 reads a detected value of the photodetector 113 and calculates a specific component based on the reference value.

As previously mentioned, the diluent container 5 can be opened by the opening/closing operation of the protective cap 2 when the user collects the sample liquid, and then the diluent can be transferred into the analyzing device 1. Thus it is possible to simplify the analyzer, reduce the cost of the analyzer, and improve operability for the user.

Moreover, the diluent container 5 is sealed with the aluminum seal 9 serving as a sealing member and the diluent container 5 is opened by breaking the aluminum seal 9 with the opening rib 11a serving as a protruding portion. Thus it is possible to prevent the diluent from being reduced by evaporation in long-term storage, improving the accuracy of analysis.

In a state of shipment of the analyzing device 1 shown in FIG. 6(a), the latch portion 10 of the diluent container 5 is engaged with the locking groove 12 of the closed protective cap 2, and the diluent container 5 is locked at the liquid retaining position so as not to move in the direction of arrow J. Although the diluent container 5 can be moved in the diluent container storage part 11 by the opening and closing operations of the protective cap 2, the diluent container 5 is not erroneously opened or the diluent does not leak during transportation by the user before use. This is because the position of the diluent container 5 in the diluent container storage part 11 is locked at the liquid retaining position in a period before the user opens the protective cap 2 to use the analyzing device 1.

Figure 16:
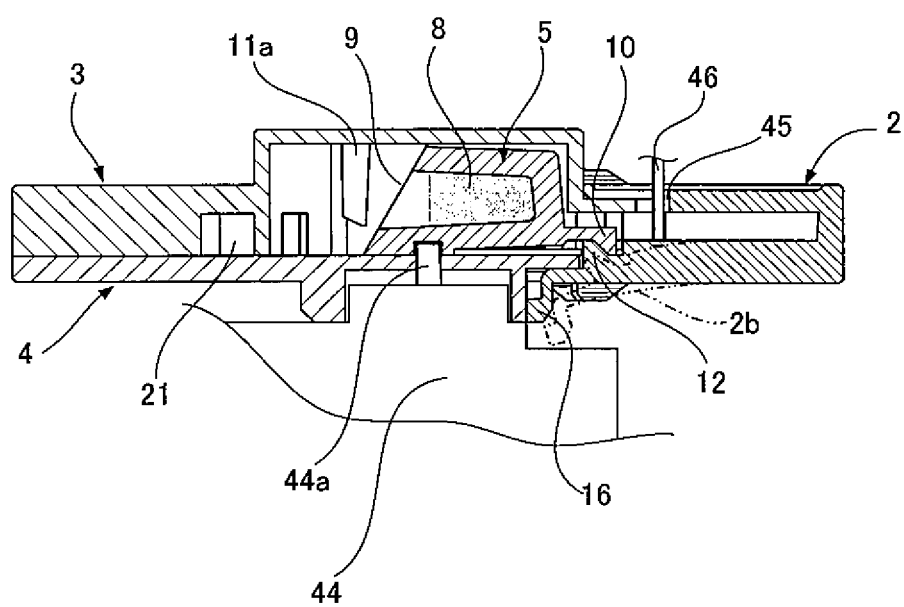
FIG. 16 is a sectional view showing a process for setting the analyzing device at a shipment state.

FIG. 16 shows a manufacturing process for setting the analyzing device 1 at the shipment state of FIG. 6(a). First, before the protective cap 2 is closed, a groove 42 (see FIGS. 2(b) and 4(d)) provided on the undersurface of the diluent container 5 and a hole 43 provided on the cover substrate 4 are aligned with each other, a protrusion 44a of a locking member 44 is engaged with the groove 42 of the diluent container 5 through the hole 43 at the liquid retaining position. The protrusion 44a is, provided separately from the base substrate 3 or the cover substrate 4. The diluent container 5 is set thus so as to be locked at the liquid retaining position. Further, from a notch 45 (see FIG. 1) formed on the top surface of the protective cap 2, a pressing member 46 is inserted and presses the bottom of the protective cap 2 to elastically deform the protective cap 2. In this state, the protective cap 2 is closed and then the pressing member 46 is removed, so that the analyzing device 1 can be set in the state of FIG. 6(a).

The foregoing embodiment described an example in which the groove 42 is provided on the undersurface of the diluent container 5. The groove 42 may be provided on the top surface of the diluent container 5 and the hole 43 may be provided on the base substrate 3 in alignment with the groove 42 to engage the protrusion 44a of the locking member 44 with the groove 42.

In the foregoing embodiment, the locking groove 12 of the protective cap 2 is directly engaged with the latch portion 10 of the diluent container 5 to lock the diluent container 5 at the liquid retaining position. The locking groove 12 of the protective cap 2 and the latch portion 10 of the diluent container 5 may be indirectly engaged with each other to lock the diluent container 5 at the liquid retaining position.

The capillary cavity 33 of FIG. 15C and a part around the capillary cavity 33 will be specifically described below.

The capillary cavity 33 serving as the first capillary cavity is formed from a bottom 23b of the separating cavity 23 to the inside. In other words, the outermost position of the capillary cavity 33 is extended outside a separation interface 18c of the plasma component 18a and the blood cell component 18b as shown in FIG. 15A.

By setting the position of the outer periphery of the capillary cavity 33 thus, the outer end of the capillary cavity 33 is immersed in the plasma component 18a and the blood cell component 18b that have been separated in the separating cavity 23. Since the plasma component 18a has a lower viscosity than the blood cell component 18b, the plasma component 18a is first sucked by the capillary cavity 33. The plasma component 18a can be transferred to the measuring chamber 40 through the capillary channel 37 and the measurement channel 38. After the plasma component 18a is sucked, the blood cell component 18b is also sucked following the plasma component 18a. Thus the plasma component 18a can be replaced with the blood cell component 18b in the capillary cavity 33 and a path halfway to the capillary channel 37. When the measurement channel 38 is filled with the plasma component 18a, the transfer of the liquid is stopped in the capillary channel 37 and the capillary cavity 33, so that the blood cell component 18b does not enter the measurement channel 38. Hence, it is possible to minimize a loss of the transferred liquid as compared with the configuration of the prior art, thereby reducing an amount of the sample liquid required for measurement.

Second Embodiment

Figure 17:
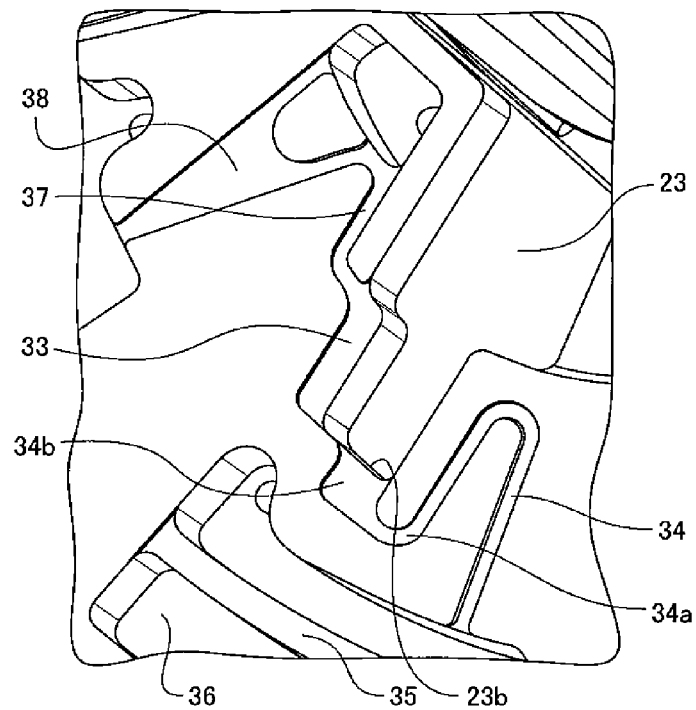
FIG. 17 is an enlarged perspective view showing a capillary cavity 33 and a portion around the capillary cavity 33 according to a second embodiment.

FIG. 17 shows a capillary cavity 33 of an analyzing device and a portion around the capillary cavity 33 according to a second embodiment. In the first embodiment of FIGS. 15A, 15B, and 15C, the connecting channel 34 for transferring the blood cell component 18b to the overflow cavity 36 has the proximal end 34a that is opened only on a corner of a wall surface on the bottom 23b of the separating cavity 23 on the opposite side from a wall surface on which the capillary cavity 33 is formed. In contrast to this configuration, in FIG. 17, a proximal end 34a of a connecting channel 34 is connected to a bottom 23b of a separating cavity 23 via a capillary cavity 34b serving as a second capillary cavity. The capillary cavity 34b has the same clearance as the proximal end 34a and is larger than the proximal end 34a in opening width and depth on the bottom 23b of the separating cavity 23. In this configuration, the connecting channel 34 is connected to the outermost position of the capillary cavity 34b.

In the configuration of FIGS. 15A, 15B, and 15C, at the end of the rotational driving of the analyzing device 1 after the centrifugal separation, the blood cell component 18b on the bottom 23b of the separating cavity 23 may be partially separated from the bottom 23b because of the viscosity, whereas in the configuration of FIG. 17, a part of a blood cell component 18b on the bottom 23b of the separating cavity 23 flows into the capillary cavity 34b and is retained by a capillary force. Thus even at the end of the rotational driving of an analyzing device 1, the capillary force of the capillary cavity 34b prevents the blood cell component 18b around the bottom 23b from separating from the bottom 23b and an amount of the blood cell component 18b retained in the separating cavity 23 is reduced, thereby preventing the blood cell component 18b from entering a measurement channel 38.

Further, the connecting channel 34 is formed of a siphon structure communicating with the outermost position of the capillary cavity 34b and bending inside the liquid level of a sample liquid retained in the separating cavity 23. Thus it is possible to discharge a liquid in the separating cavity 23, a capillary channel 37, the capillary cavity 33, and the capillary cavity 34b to an overflow cavity 36.

Third Embodiment

Figure 18:
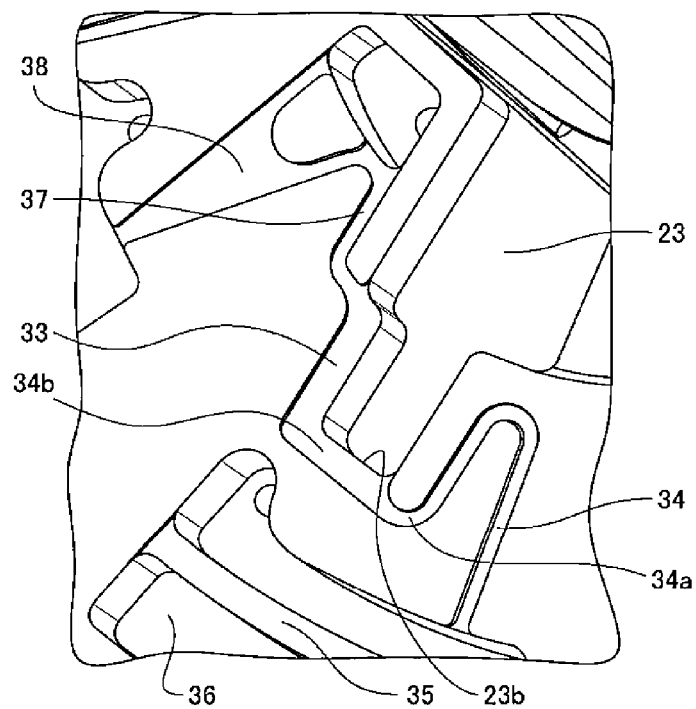
FIG. 18 is an enlarged perspective view showing a capillary cavity 33 and a portion around the capillary cavity 33 according to a third embodiment.

FIG. 18 shows a capillary cavity 33 of an analyzing device and a portion around the capillary cavity 33 according to a third embodiment. In FIG. 17, the capillary cavity 33 and the capillary cavity 34b are separately provided, whereas in FIG. 18, the capillary cavity 33 and a capillary cavity 34b are connected to each other via an opening provided on a bottom 23b. A connecting channel 34 communicates with the outermost position of the capillary cavity 34b and has a siphon structure bending inside the liquid level of a sample liquid retained in a separating cavity 23.

With this configuration, a boundary position where the capillary cavity 34b and the separating cavity 23 are connected to each other can be formed close to a separation interface 18c of the sample liquid. Thus a blood cell component 18b is more unlikely to be sucked by the capillary cavity 33, thereby more reliably preventing the blood cell component 18b from entering a measurement channel 38.

In the examples of the foregoing embodiments, the analyzing device 1 is rotated about the rotation axis 107 to transfer, to the measuring chamber 40, a component centrifugally separated from the sample liquid and the diluent 8 released from the diluent container 5, and then the solution component is diluted. Further, an analysis is performed by accessing the solution component separated from the sample liquid or a reactant of the solution component separated from the sample liquid and the reagent. When it is not necessary to separate the solution component from the sample liquid, the process of centrifugal separation is not necessary. In this case, the analyzing device 1 is rotated about the rotation axis 107 to transfer, to the measuring chamber 40, an overall fixed amount of the dropped sample liquid and the diluent 8 released from the diluent container 5, and then the sample liquid is diluted. Further, an analysis is performed by accessing the solution component diluted with the diluent or a reactant of the solution component diluted with the diluent and the reagent.

Moreover, the analyzing device 1 may be rotated about the rotation axis 107 to transfer, to the measuring chamber, a solid component separated from the sample liquid and the diluent released from the diluent container 5, and then the solid component may be diluted. An analysis may be performed by accessing the solid component separated from the sample liquid or a reactant of the solid component separated from the sample liquid and the reagent.

In the foregoing embodiment, an analyzing device body in which a microchannel structure is formed with a minutely uneven surface is made up of two layers of the base substrate 3 and the cover substrate 4. The analyzing device body may be configured by bonding at least three substrates. To be specific, examples include a three-layer structure in which a substrate having a notch formed according to a microchannel structure is set at the center and the notch is closed to form the microchannel structure with other substrates bonded to the top surface and the undersurface of the substrate.

Fourth Embodiment

In the foregoing embodiments, one end of the capillary cavity 33 for sucking the plasma component from the separating cavity 23 is extended under (to the outer periphery) the separation interface 18c in the separating cavity 23, so that a required amount of crystal can be collected from a small amount of blood. In the fourth embodiment, a blood separating wall 129 is formed in a separating cavity 23, thereby more reliably preventing a small amount of a blood cell component from being mixed with a plasma component sucked by a capillary cavity 33.

A plasma retaining part 130 of the fourth embodiment corresponds to the separating cavity 23 and a plasma collecting capillary 125 of the fourth embodiment corresponds to the capillary cavity 33. A plasma measuring part 127 of the fourth embodiment corresponds to the measurement channel 38 and a first U-shaped siphon channel 127a of the fourth embodiment corresponds to the capillary channel 37.

Figure 20:
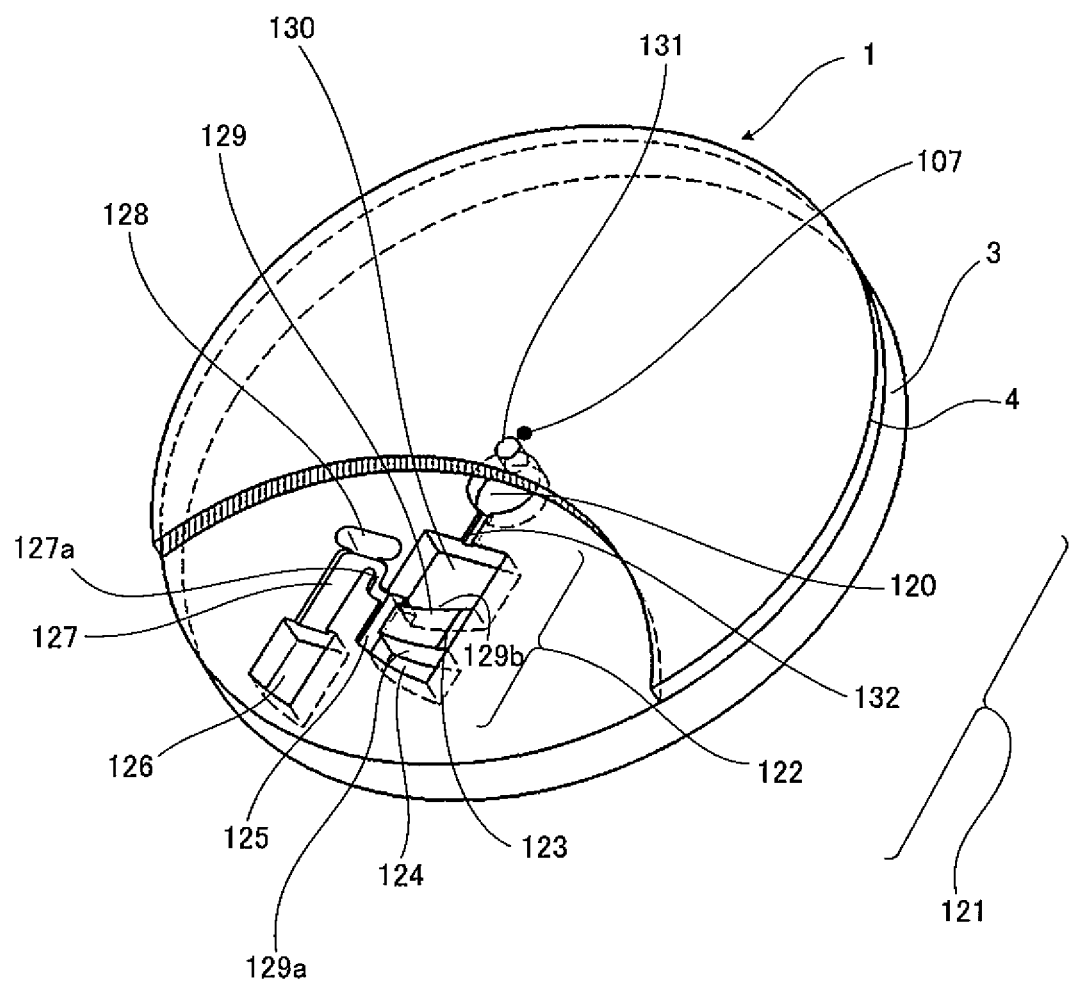
FIG. 20 is an enlarged perspective view showing a notch of an analyzing device according to a fourth embodiment of the present invention.

FIG. 20 shows an analyzing device according to the fourth embodiment of the present invention.

An analyzing device 1 is made up of a base substrate 3 formed of a microchannel 121 including capillary channels, retaining parts, and separating parts that are formed of a plurality of recessed portions with different depths on a surface of a circular substrate, and a cover substrate 4 joined over the microchannel 121 formed on the base substrate 3.

The microchannel 121 formed on the base substrate 3 is made of a synthetic resin material prepared by injection molding or cutting.

Blood as a sample liquid for analysis is introduced from a supply channel 131 formed on the cover substrate 4, the blood is transferred to a blood separating part 122 formed on the base substrate 3, and then the blood is centrifugally separated. After that, a centrifugal force is stopped to apply a capillary force to a plasma measuring part 127, so that only a plasma component is collected. Further, a centrifugal force is generated again to transfer the plasma component to a reagent reacting part 126, so that the plasma and a reagent are reacted and a reaction liquid can be inspected.

In the present invention, the plasma to be inspected and the reagent are reacted and then light is emitted to the reagent reacting part 126 from the outside to optically analyze the state of reaction. During measurement, the reaction liquid supplied into the reagent reacting part 126 changes an absorbance according to a rate of reaction. By emitting light to the reagent reacting part 126 from a light source part and measuring an amount of light on a light receiving part, it is possible to measure a change in the amount of light having passed through the reaction liquid, thereby analyzing the characteristics of the sample liquid.

The configuration of the base substrate 3 will be specifically described below.

The base substrate 3 of the present invention is made up of a substrate formed by injection molding or cutting. The thickness of the base substrate 3 is 1 mm to 5 mm, which is not particularly limited as long as the thickness allows the formation of the microchannel 121. In the case where the analyzing device 1 is rotated alone, the base substrate 3 is desirably shaped like a circle. In the case where the analyzing device 1 is rotated on an external attachment, the shape of the analyzing device 1 is not particularly limited and thus the shape can be determined according to the purpose. For example, the analyzing device 1 may be shaped like a square, a triangle, a sector, and other complicated forms.

The base substrate 3 and the cover substrate 4 are made of synthetic resins in view of high moldability, high productivity, and low cost. The materials of the substrates are not particularly limited and thus may be glasses, silicon wafers, metals, ceramics, and the like as long as the substrates can be joined to each other.

On the base substrate 3, hydrophilic treatment is performed on a part of the wall surface or over the wall surface in order to reduce viscous drag and accelerate fluid migration in the microchannel 121. Hydrophilicity may be provided on a material surface by using a hydrophilic material such as glass or adding a surface-active agent, a hydrophilic polymer, and a hydrophilizing agent of hydrophilic powder such as silica gel during molding. Methods of hydrophilic treatment include a surface treatment method using active gas of plasma, corona, ozone, fluorine, and so on and surface treatment using a surface-active agent. In this case, hydrophilicity has a contact angle of less than 90° relative to water. More preferably, the contact angle is less than 40°.

In the present embodiment, the base substrate 3 and the cover substrate 4 are joined by ultrasonic welding. The base substrate 3 and the cover substrate 4 may be joined using an adhesive bonding sheet and a joining method such as anodic bonding and laser bonding according to a used material.

The following will describe the configuration of the microchannel 121 of the analyzing device 1 and a process for injecting and transferring blood.

As shown in FIG. 20, the microchannel 121 is formed from the vicinity of a rotation axis 107 of the base substrate 3 to the outer periphery of the base substrate 3. To be specific, the microchannel 121 is made up of a blood retaining part 120 that is disposed closest to the rotation axis 107 to inject blood, the blood separating part 122 disposed outside the blood retaining part 120, a blood channel 132 that connects the blood retaining part 120 and the blood separating part 122 and is formed of a capillary, the plasma measuring part 127 that is adjacent to the blood separating part 122 and is connected to the side wall of the blood separating part 122 via a U-shaped siphon channel 127*a*, an air hole 128 that is connected to the plasma measuring part 127 and is provided from the plasma measuring part 127 toward the rotation axis 107, and the reagent reacting part 126 that is connected to the plasma measuring part 127 and is disposed outside the plasma measuring part 127.

Further, the inside of the blood separating part 122 is divided into the side of the rotation axis 107 and the outer side by the blood separating wall 129 formed in the circumferential direction. The side of the rotation axis 107 serves as the plasma retaining part 130 and the outer side serves as a blood cell retaining part 124.

On the blood separating wall 129, the plasma collecting capillary 125 and an air channel 123 are formed so as to connect the plasma retaining part 130 and the blood cell retaining part 124. The plasma collecting capillary 125 has the ends protruding to the plasma retaining part 130 and the blood cell retaining part 124 and communicates with the plasma measuring part 127 through the siphon channel 127*a*. The end protruding from the plasma collecting capillary 125 to the blood cell retaining part 124 reaches the bottom of the blood cell retaining part 124.

The blood separating wall 129 is formed such that the capacity of the blood cell retaining part 124 is 65% to 70% of an amount of blood injected into the blood retaining part 120. Further, a wall surface 129*a* of the blood separating wall 129 is in contact with the blood cell retaining part 124 and is formed of a circular surface at a constant distance from the rotation axis 107. A wall surface 129*b* of the blood separating wall 129 is in contact with the plasma retaining part 130 and is formed at a distance increasing toward the plasma collecting capillary 125 from the rotation axis 107.

The cover substrate 4 covering the base substrate 3 has the same outside shape as the base substrate 3. Blood can be injected to the blood retaining part 120 of the base substrate 3 from the supply channel 131 formed around the rotation axis 107.

The following will describe a transfer process from the injection of blood to the reagent reacting part 126, along with the configuration.

Figure 21:
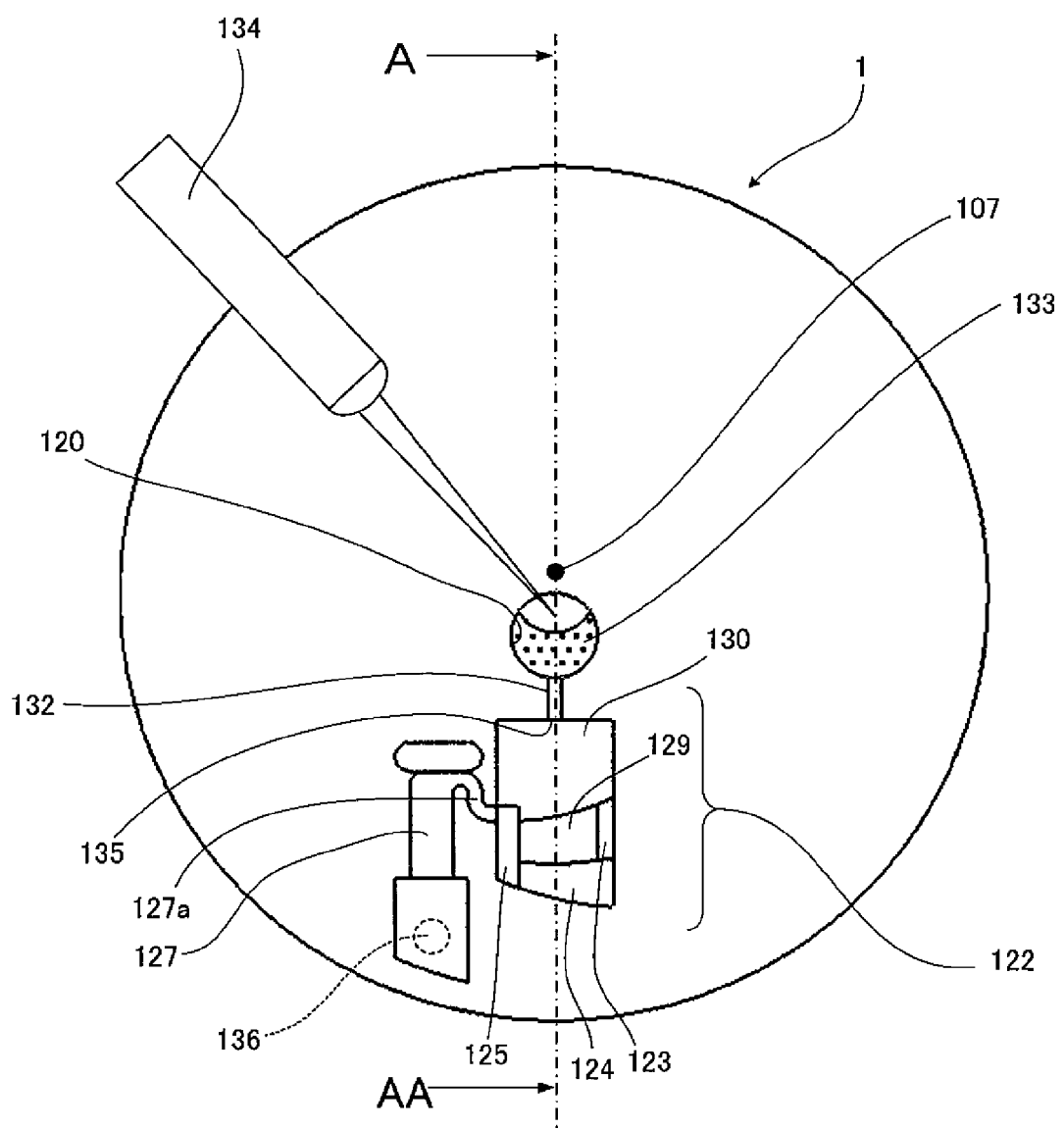
FIG. 21 is a schematic diagram showing a blood injection process according to the embodiment.

First, as shown in FIG. 21, blood 133 is measured and injected into the supply channel 131 by a pipet 134 and the like. In the present embodiment, 10 µl of blood was measured and injected by the pipet 134.

The blood 133 injected from the pipet 134 fills the blood retaining part 120. At this point, the blood 133 injected into the blood retaining part 120 also enters the blood channel 132 connecting the blood retaining part 120 and the blood separating part 122. However, the blood 133 stops at a joint 135 of the blood channel 132 and the blood separating part 122.

Figure 22:
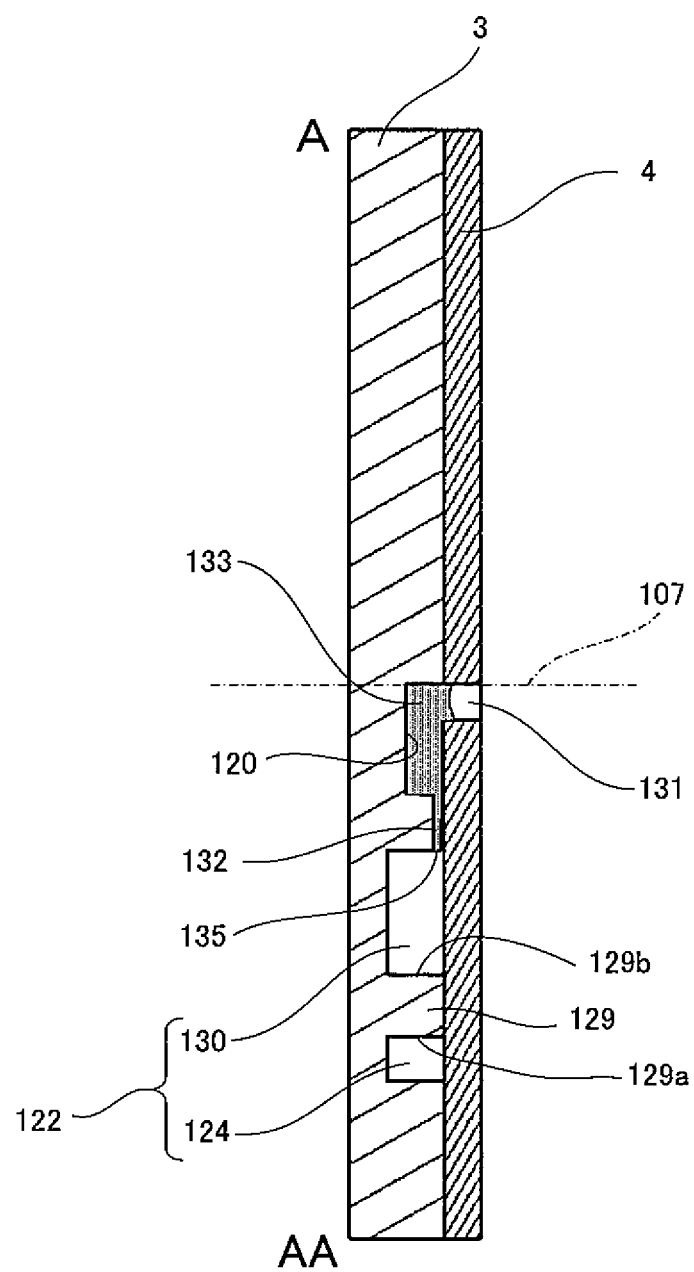
FIG. 22 is an A-AA sectional view of FIG. 21 according to the embodiment.

FIG. 22 is an A-AA sectional view of FIG. 21.

The depth of the blood channel 132 is formed of a small clearance enabling a capillary force. The blood separating part 122 is formed deeper than the blood channel 132 so that a capillary force is not applied.

When the blood 133 is injected into the blood separating part 122, the injected blood 133 is injected into the blood retaining part 120 and enters the blood channel 132 by a capillary force. Since the blood separating part 122 is deeper than the blood channel 132, the capillary force is interrupted at the joint 135 of the blood channel 132 and the blood separating part 122 and the interface of the blood 133 is kept by a surface tension, thereby preventing the blood from entering the blood separating part 122.

The blood retaining part 120 may have any depth as long as a desired amount of the blood 133 can be retained.

Generally, it is said that the influence of a capillary force becomes significant when a capillary has an interior diameter of 2.5 mm or less. The capillary force is a force of liquid transfer in a capillary when a liquid is moved by a force keeping the balance of a contact angle formed by a wall surface and the liquid and a surface tension applied between gas-liquid interfaces.

The following will describe the centrifugal separation of the blood 133.

Figure 23:
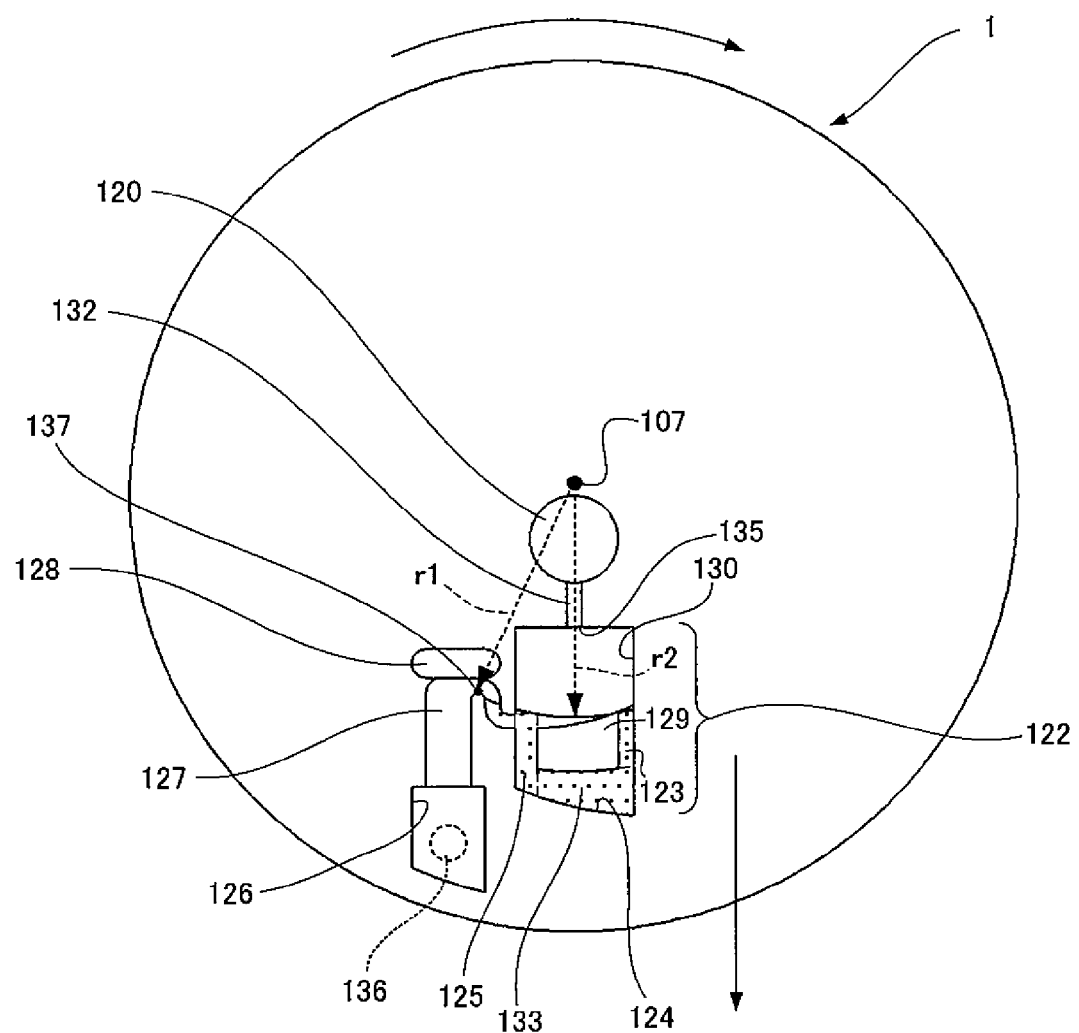
FIG. 23 is a first schematic diagram showing a centrifugal transfer process according to the embodiment.

As shown in FIG. 23, a centrifugal force is generated by rotating the analyzing device 1 about the rotation axis 107 at a first rotation speed in the direction of an arrow. At this point, the generated centrifugal force is larger than a surface tension applied to the interface of the blood retained at the position of the joint 135 of the blood channel 132 and the blood separating part 122, so that the injected blood 133 is transferred into the blood separating part 122.

The blood 133 transferred into the blood separating part 122 passes through the plasma retaining part 130 and then is transferred to the blood cell retaining part 124 through one of the air channel 123 and the plasma collecting capillary 125 that are formed on both ends of the blood separating wall 129.

To be specific, the first rotation speed, which is the rotation speed of the analyzing device 1 at this point, is set such that at least a gravity of 1000 Gs is applied to the blood transferred to the blood separating part 122. In the plasma collecting capillary 125, a capillary force is smaller than a centrifugal force applied to a plasma component 139. In the present embodiment, the first rotation speed is set at 5000 rpm.

The blood 133 transferred to the blood cell retaining part 124 first fills the blood cell retaining part 124 and moves the interface of the blood 133 to the plasma retaining part 130 while filling the plasma collecting capillary 125 and the air channel 123. The transferred blood 133 also enters the plasma measuring part 127 connected to the blood separating part 122. A distance r1 from the rotation axis 107 to a siphon top 137 formed on the plasma measuring part 127 is larger than a distance r2 from the rotation axis 107 to the interface of the blood 133 during rotation, so that the blood 133 during rotation does not enter the plasma measuring part 127 and the reagent reacting part 126.

Figure 24:
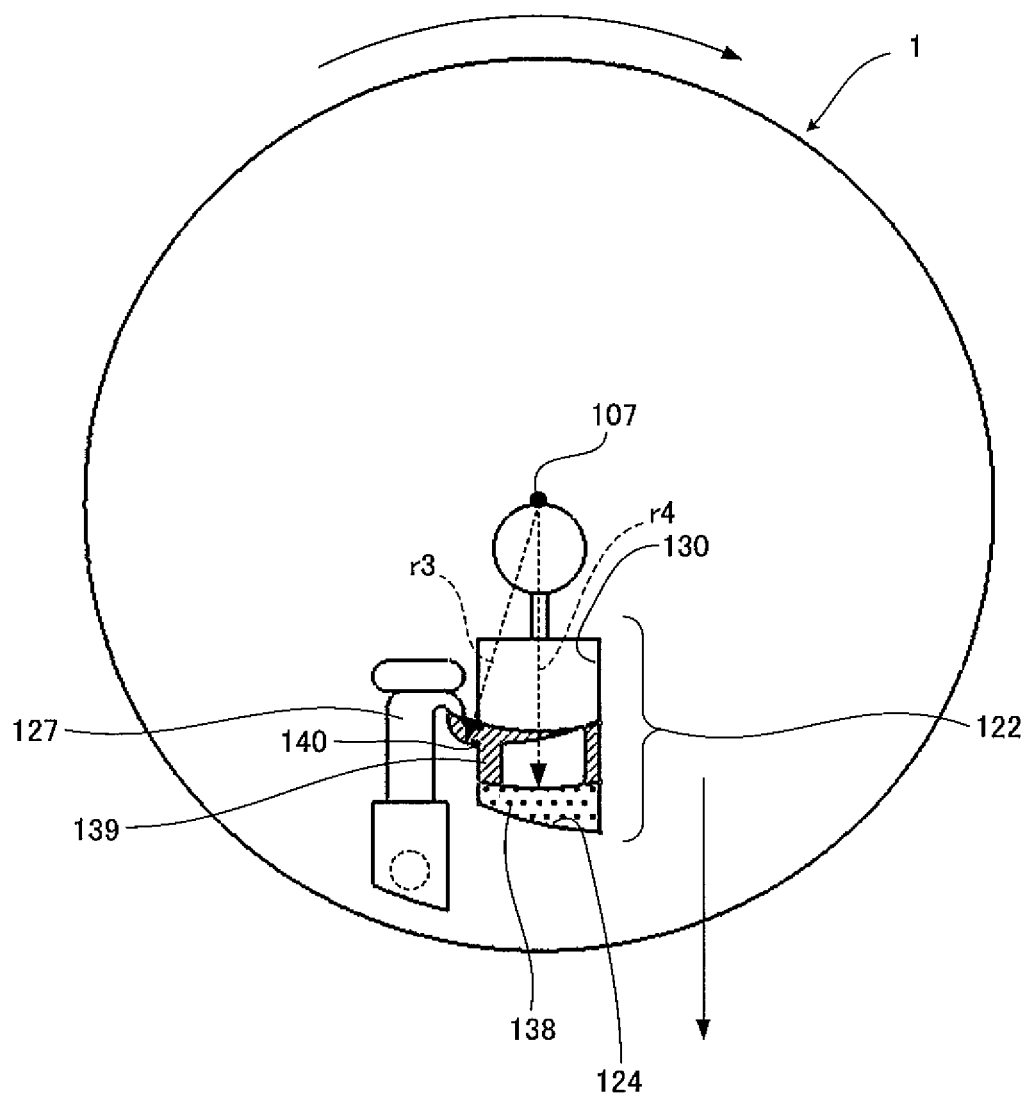
FIG. 24 is a second schematic diagram showing the centrifugal transfer process according to the embodiment.

Further, by keeping the first rotation speed, a blood cell component 138 in the blood 133 moves in a centrifugal direction as shown in FIG. 24, that is, to the outer periphery of the blood separating part 122 and the plasma component 139 is moved closer to the rotation axis 107. To be specific, the components of the blood 133 are mainly divided into the plasma component 139 that includes protein and cholesterol and the blood cell component 138 that includes a white blood cell, a red blood cell, and a platelet. The specific gravity of the blood cell component 138 is 1.2 to 1.3 times higher than that of the plasma component 139. Thus the blood cell component 138 having a higher specific gravity is moved to the outer periphery of the analyzing device 1 by a centrifugal force.

By further keeping the first rotation speed, as shown in FIG. 24, the plasma component 139 is separated to the plasma retaining part 130 and the blood cell component 138 is separated to the blood cell retaining part 124.

At this point, it is necessary to design the configuration such that the interface of the blood cell component 138 and the plasma component 139 does not enter the plasma measuring part 127 even at the maximum hematocrit (in this case, the maximum hematocrit of ordinary human blood is set at Hct=60%). This is because the blood cell component 138 entering the plasma measuring part 127 may increase in flowability at the joint of the plasma measuring part 127 and the blood separating part 122 during blood plasma measurement using a capillary force, and thus the blood cell component 138 may be mixed with the plasma component 139 to be measured.

Figure 25:
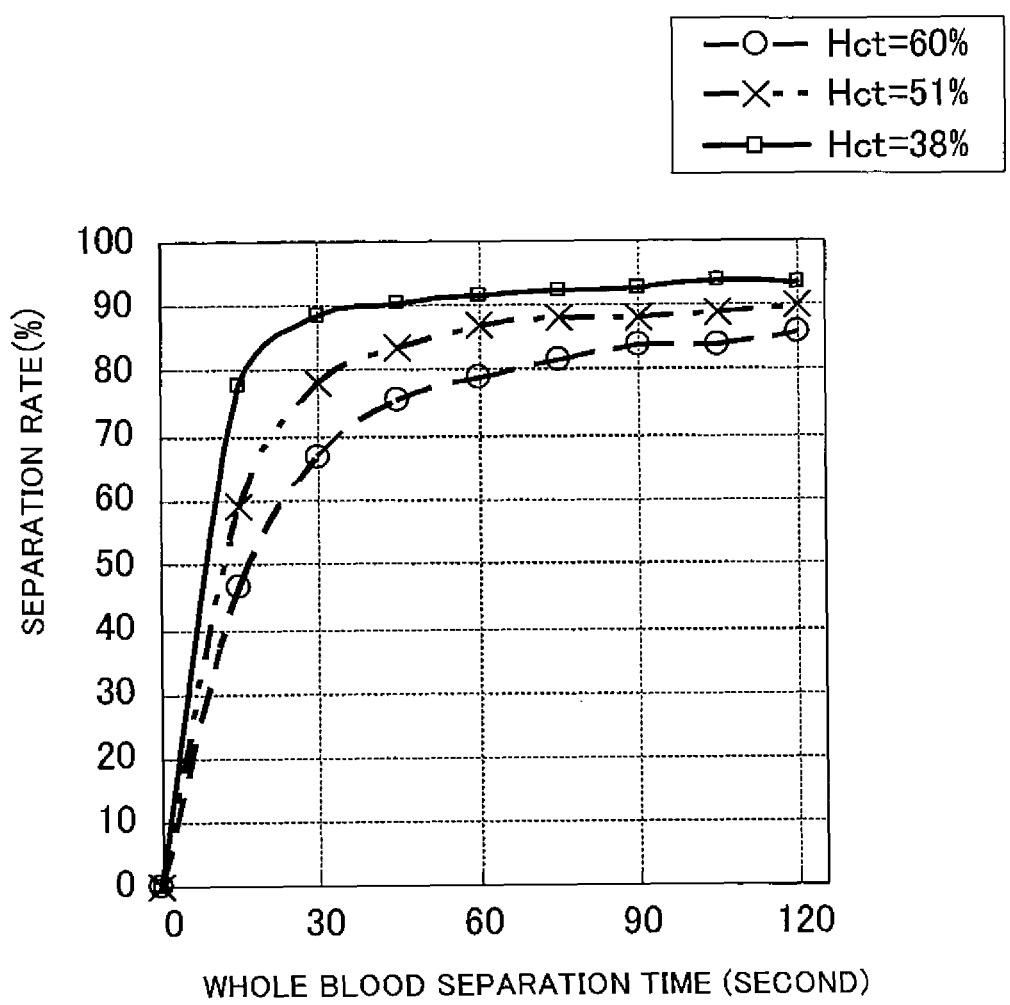
FIG. 25 is a diagram showing the relationship between a blood separation rate and a blood separation time according to the embodiment.

FIG. 25 shows the relationship between the separation rate and separation time of the plasma component 139 relative to blood varying in hematocrit (Hct=38%, 51%, 60%). The number of revolutions is set so as to apply a centrifugal force of 1500 G to the blood 133.

According to this result, the lower the hematocrit, the higher the separation rate of the plasma component 139. The result also proves that a separation rate of at least 80% with a high hematocrit requires a centrifugal separation time of at least 60 seconds. Assuming that the hematocrit of human blood is 30% to 60%, it is necessary to design a plasma collecting capillary 112 and the blood separating part 122 with a separation rate of 80% in a whole blood separation time of at least 60 seconds to centrifugally separate the whole blood with reliability.

In the present embodiment, the relationship of r3<r4 is established where r4 is a distance from the rotation axis 107 to the interface of the plasma component 139 and the blood cell component 138 when blood with a hematocrit of 60% is centrifugally separated, and r3 is a distance from the rotation axis 107 to a joint 140 of the siphon channel 127a communicating with the plasma measuring part 127 and the blood separating part 122.

The following will describe the measurement and collection of the plasma component 139.

Figure 26:
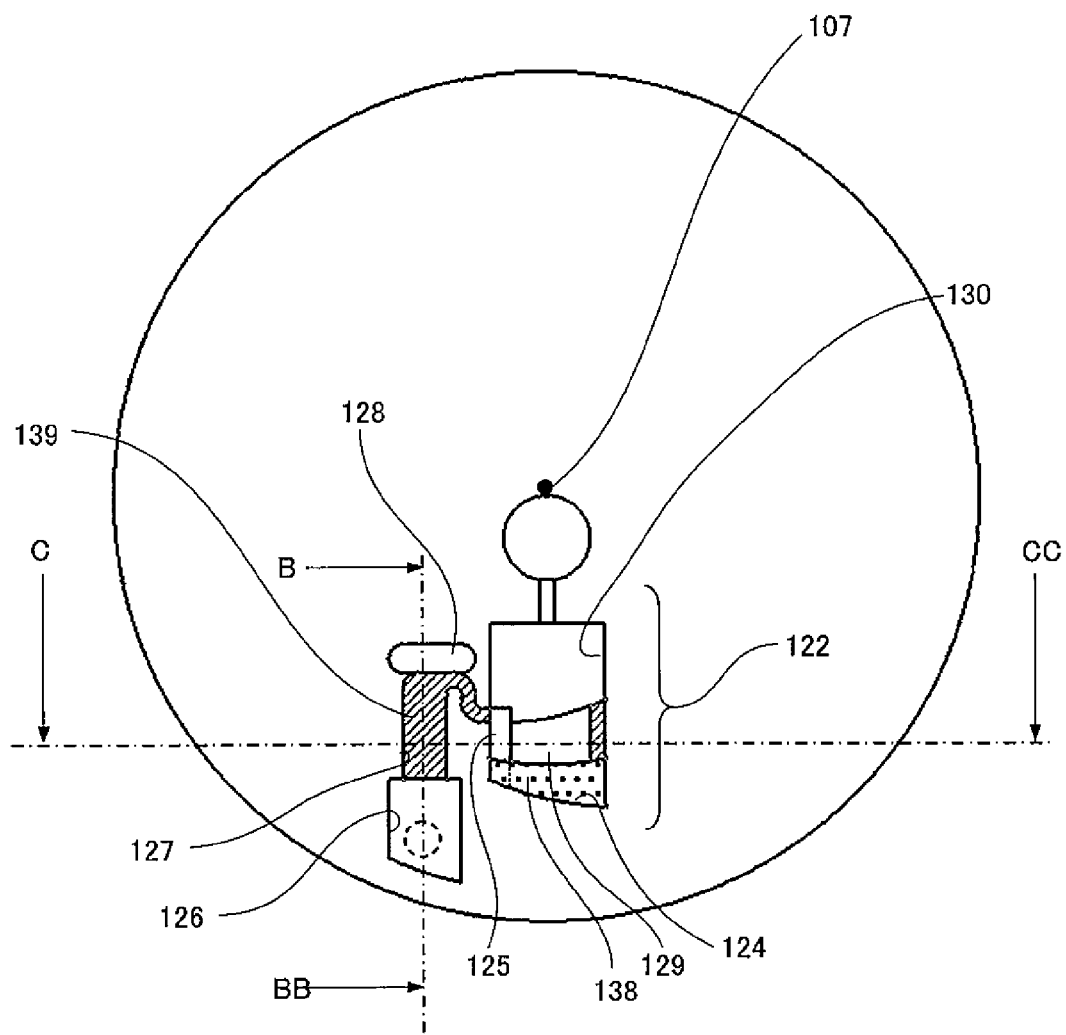
FIG. 26 is a schematic diagram showing a capillary transfer process according to the embodiment.
Figure 27A:
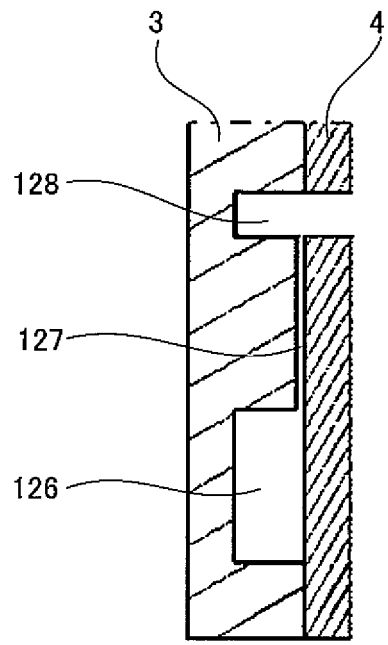
FIG. 27A is a B-BB sectional view of FIG. 26 according to the embodiment.
Figure 27B:
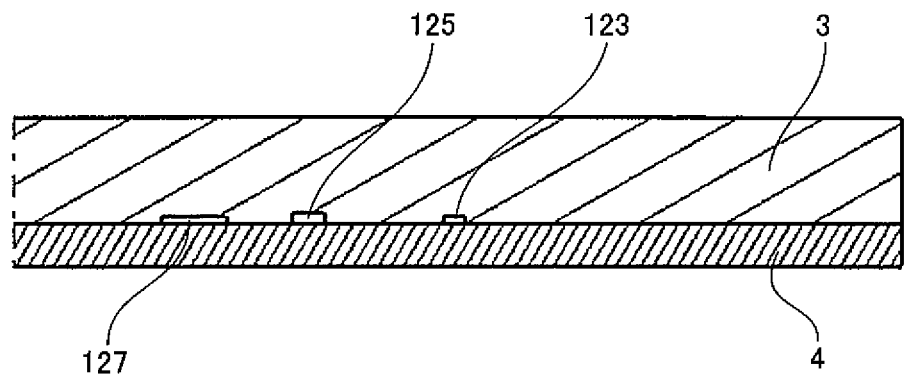
FIG. 27B is a C-CC sectional view of FIG. 26 according to the embodiment.

As shown in FIG. 26, the rotation speed is reduced to the second rotation speed or the rotation is stopped to reduce a centrifugal force or hinder the action of the centrifugal force, so that the capillary force having been suppressed by the centrifugal force in the plasma measuring part 127 is released so as to transfer, to the plasma measuring part 127, only the plasma component 139 separated by the centrifugal separation. This is because the plasma component 139 having higher flowability is more likely to enter the plasma measuring part 127, whereas the blood cell component 138 separated by the centrifugal separation increases in viscosity and extremely decreases in flowability owing to coagulation of blood cells. At this point, the second rotation speed is set such that the capillary force becomes dominant over a centrifugal force acting in the plasma collecting capillary 125. In the present embodiment, the second rotation speed is set at 600 rpm. FIGS. 27A and 27B are schematic drawings of section B-BB and section C-CC of FIG. 26. As shown in FIG. 27B, the plasma collecting capillary 125 is formed deeper than the plasma measuring part 127.

Further, the plasma retaining part 130 is formed deeper than the plasma collecting capillary 125.

Moreover, the plasma collecting capillary 125 and the plasma measuring part 127 are both formed with a depth of 2.5 mm or less to allow a capillary force to act in the plasma collecting capillary 125 and the plasma measuring part 127. By using a capillary force increasing with a reduction in depth, the plasma component 139 separated in the plasma retaining part 130 is first transferred to the plasma measuring part 127, and then the plasma component 139 in the plasma collecting capillary 125 is transferred to the plasma measuring part 127. Thus it is possible to prevent the blood cell component 138 from entering the plasma measuring part 127 and reduce a loss of the plasma component 139 remaining in the blood separating part 122.

The plasma component 139 collected by the plasma measuring part 127 is stopped and measured at the joint of the plasma measuring part 127 and the air hole 128 and the joint of the plasma measuring part 127 and the reagent reacting part 126. This is because as shown in FIG. 27A, the air hole 128 and the reagent reacting part 126 are formed deeper than the plasma measuring part 127 and thus a capillary force is eliminated at the joint of the air hole 128 and the joint of the reagent reacting part 126 so as to stop the measured plasma component 139 at the joints.

A reagent reaction will be described below.

Figure 28:
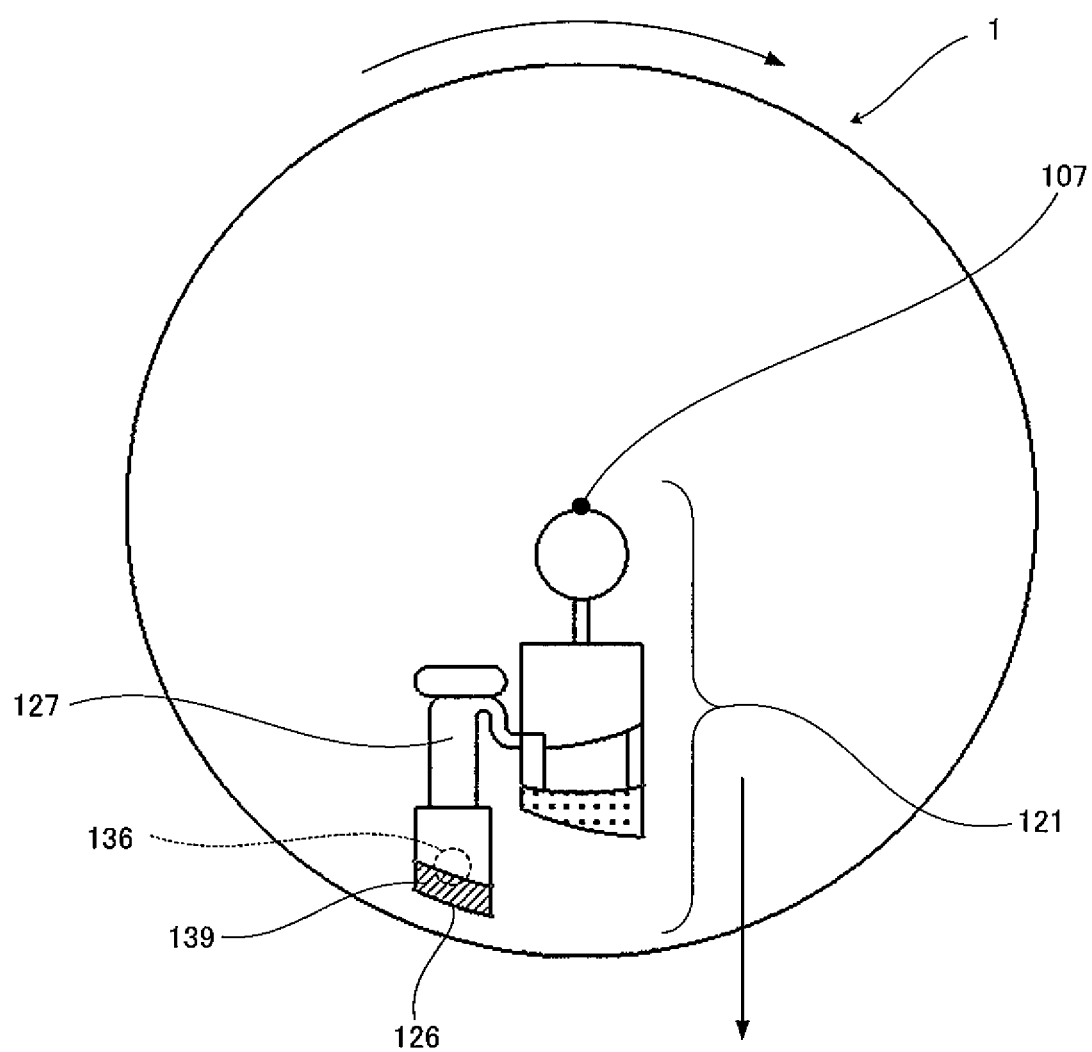
FIG. 28 is a first schematic diagram showing a reaction process according to the embodiment.
Figure 29:
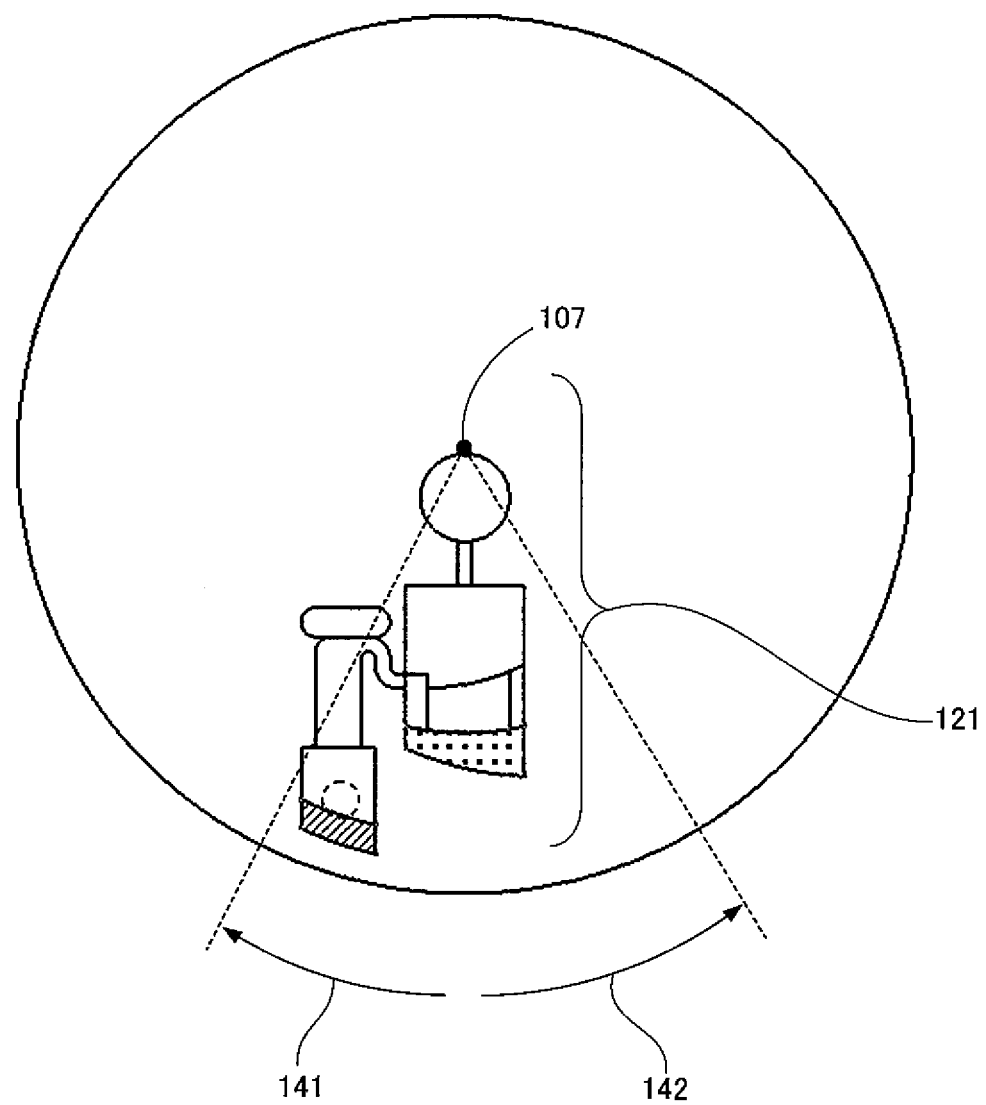
FIG. 29 is a second schematic diagram showing a reaction process according to the embodiment.

As shown in FIG. 28, the analyzing device 1 is rotated to generate a centrifugal force, so that the plasma component 139 measured in the plasma measuring part 127 is transferred to the reagent reacting part 126. At this point, a reagent 136 disposed in the reagent reacting part 126 and the plasma component 139 come into contact with each other, so that a reaction starts. When the reactivity of the reagent 136 and the plasma component 139 is low, the analyzing device 1 is swung as shown in FIG. 29 to accelerate the reactivity of the reagent 136. The analyzing device 1 is swung by repeatedly changing the rotation direction of the analyzing device 1. To be specific, as shown in FIG. 29, the analyzing device 1 is swung so as to alternately move in a clockwise direction 141 and a counterclockwise direction 142 by 20° with the microchannel 121 in 6 o'clock position. After that, a reaction liquid can be analyzed by an optical measurement method.

As previously mentioned, in the analyzing device 1 of the present embodiment, the microchannel 121 configured thus makes it possible to collect a required amount of the plasma component 139 from a small amount of blood without mixing blood cells. Further, an amount of blood as a specimen is 10 μl (equivalent to a grain of rice), thereby reducing a load of a patient to be inspected and the size of the analyzing device.

In the foregoing embodiment, the wall surface 129b of the blood separating wall 129 is in contact with the plasma retaining part 130 such that a distance from the rotation axis 107 to the wall surface 129b increases toward the plasma collecting capillary 125. The wall surface 129b may be a circular surface at a fixed distance from the rotation axis 107.

Fifth Embodiment

The first to fourth embodiments described examples in which a plasma component is measured from blood before dilution. As will be described in a fifth embodiment, the present invention can be similarly implemented also by diluting blood with a diluent and then measuring a plasma component sucked from the diluted blood.

In the first to fourth embodiments, a component is measured based on an amount of attenuation by optically accessing a measurement spot on the reactant of a reagent and a sample. A component may be measured by electrically accessing a measurement spot on the reactant of a reagent and a sample.

When a component is measured from an amount of attenuation by optically accessing a measurement spot, only a diluent is measured as will be described in the fifth embodiment, so that a correct analysis result can be expected without any errors of an optical path length.

FIGS. 30A and 30B to 48 show an analyzing device of the fifth embodiment.

Figure 30A:
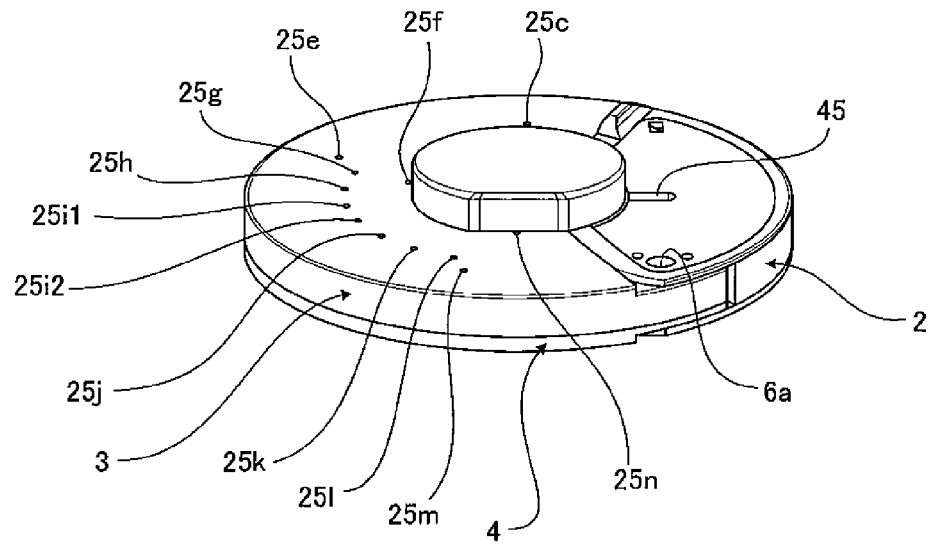
FIG. 30A is an external perspective view showing an analyzing device with a closed protective cap according to a fifth embodiment of the present invention.
Figure 30B:
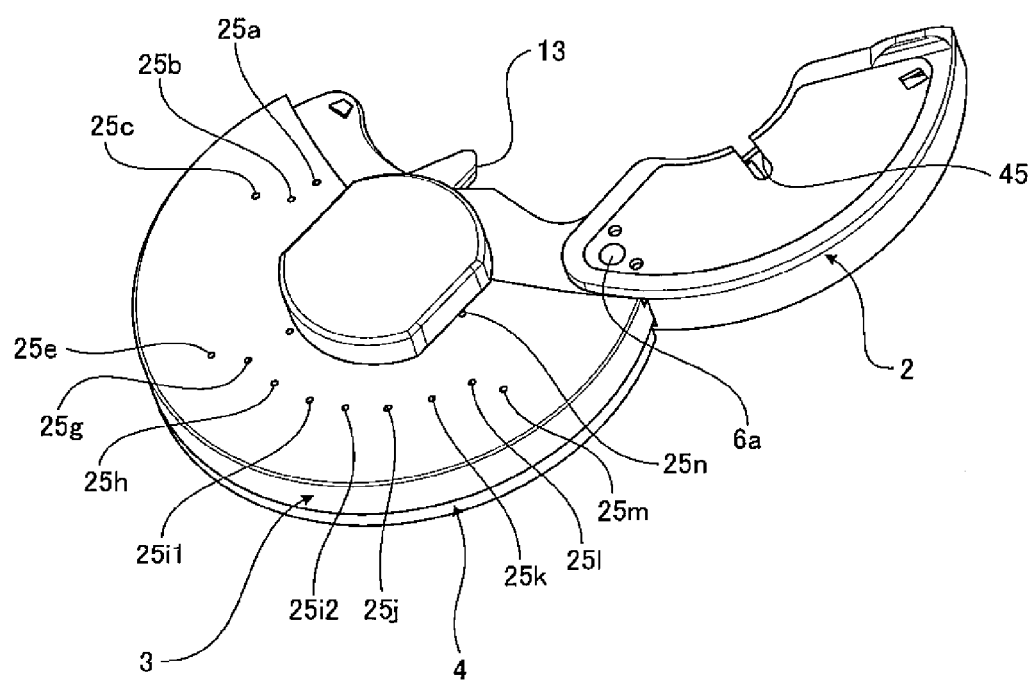
FIG. 30B is an external perspective view showing the analyzing device with the opened protective cap according to the embodiment of the present invention.
Figure 31:
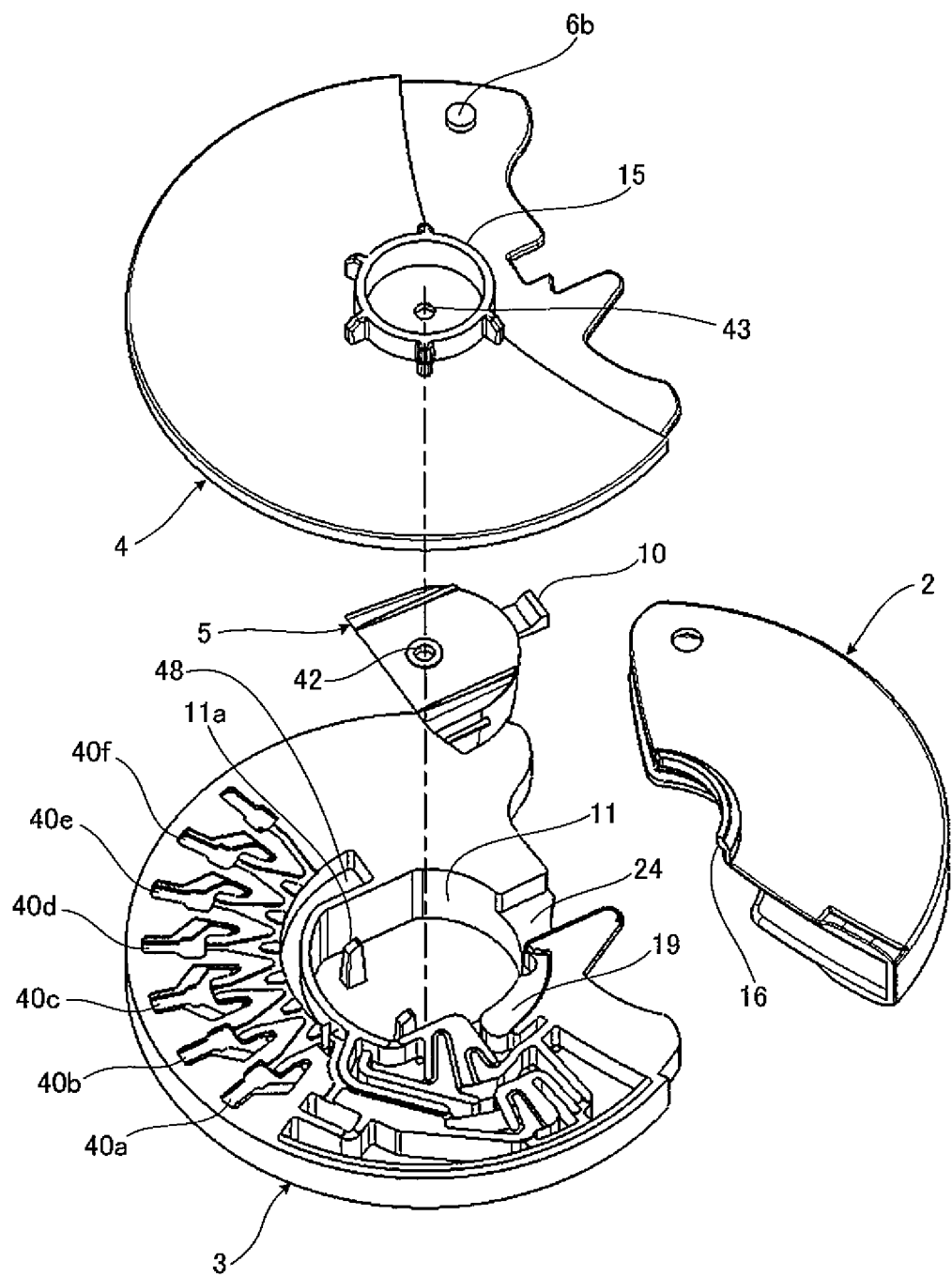
FIG. 31 is an exploded perspective view showing the analyzing device according to the embodiment.

FIGS. 30A and 30B show an analyzing device 1 with an opened/closed protective cap 2. FIG. 31 is an exploded view of the analyzing device 1 with the underside of FIG. 30A placed face up.

As shown in FIGS. 30A, 30B, and 31, the analyzing device 1 is made up of four components of a base substrate 3 having a microchannel structure formed on one surface, the microchannel structure having a minutely uneven surface, a cover substrate 4 for covering the surface of the base substrate 3, a diluent container 5 for containing a diluent, and the protective cap 2 for preventing splashes of a sample liquid.

The base substrate 3 and the cover substrate 4 are joined to each other with the diluent container 5 set in the base substrate 3 and the cover substrate 4, and the protective cap 2 is attached to the joined base substrate 3 and cover substrate 4.

The cover substrate 4 covers the openings of several recessed portions formed on the top surface of the base substrate 3, thereby forming a plurality of storage areas described later (the same as measurement chambers described later), the channels of the microchannel structure for connecting the storage areas, and so on. Necessary ones of the storage areas are filled beforehand with reagents necessary for various analyses. One side of the protective cap 2 is pivotally supported such that the protective cap 2 can be opened and closed in engagement with shafts 6a and 6b formed on the base substrate 3 and the cover substrate 4. When a sample liquid to be inspected is blood, the channels of the microchannel structure in which a capillary force is applied have clearances of 50 μm to 300 μm.

The outline of an analyzing process using the analyzing device 1 is that a sample liquid is dropped to the analyzing device 1 in which a diluent has been set, at least a part of the sample liquid is diluted with the diluent, and then a measurement is conducted.

The fifth embodiment is similar to the first embodiment in the shape of the diluent container 5 and in that the diluent container 5 is enclosed with an aluminum seal 9 after being filled with a diluent 8, a latch portion 10 is formed on the opposite side of the diluent container 5 from an opening 7, and the diluent container 5 is set in a diluent container storage part 11 formed between the base substrate 3 and the cover substrate 4 and is stored movably between a liquid retaining position and a liquid discharging position.

The fifth embodiment is also similar to the first embodiment in the shape of the protective cap 2 and in that a locking groove 12 is formed inside the protective cap 2 such that the latch portion 10 of the diluent container 5 can be engaged with the locking groove 12.

After the analyzing device 1 is set on a rotor 101, a door 103 of an analyzer is closed before a rotation of the rotor 101, so that the set analyzing device 1 is pressed to the side of the rotor 101 by a movable piece 104 provided on the side of the door 103, with the biasing force of a spring 105 at a position on the rotation axis of the rotor 101. Thus the analyzing device 1 rotates together with the rotor 101 rotationally driven by a rotational drive 106. Reference numeral 107 denotes the axis of rotation of the rotor 101. The protective cap 2 is attached to prevent the sample liquid deposited around an inlet 13 from being splashed to the outside by a centrifugal force during an analysis.

The components constituting the analyzing device 1 are desirably made of resin materials enabling low material cost with high mass productivity. The analyzer 100 analyzes the sample liquid according to an optical measurement method for measuring light passing through the analyzing device 1. Thus the base substrate 3 and the cover substrate 4 are desirably made of transparent synthetic resins including PC, PMMA, AS, and MS.

The diluent container 5 is desirably made of crystalline synthetic resins such as PP and PE that have low moisture permeability. This is because the diluent container 5 has to contain the diluent 8 for a long period. The protective cap 2 may be made of any materials as long as high moldability is obtained. Inexpensive resins such as PP and PE are desirable.

The base substrate 3 and the cover substrate 4 are desirably joined to each other according to a method hardly affecting the reaction activity of a reagent retained in the storage area. Thus ultrasonic welding, laser welding, and so on are desirable because reactive gas and solvent are hardly generated during joining.

On a portion where a solution is transferred by a capillary force in a small clearance between the base substrate 3 and the cover substrate 4 that are joined to each other, hydrophilic treatment is performed to increase the capillary force. To be specific, hydrophilic treatment is performed using a hydrophilic polymer, a surface-active agent, and so on. In this case, hydrophilicity means a contact angle of less than 90° relative to water. More preferably, the contact angle is less than 40°.

Figure 32:
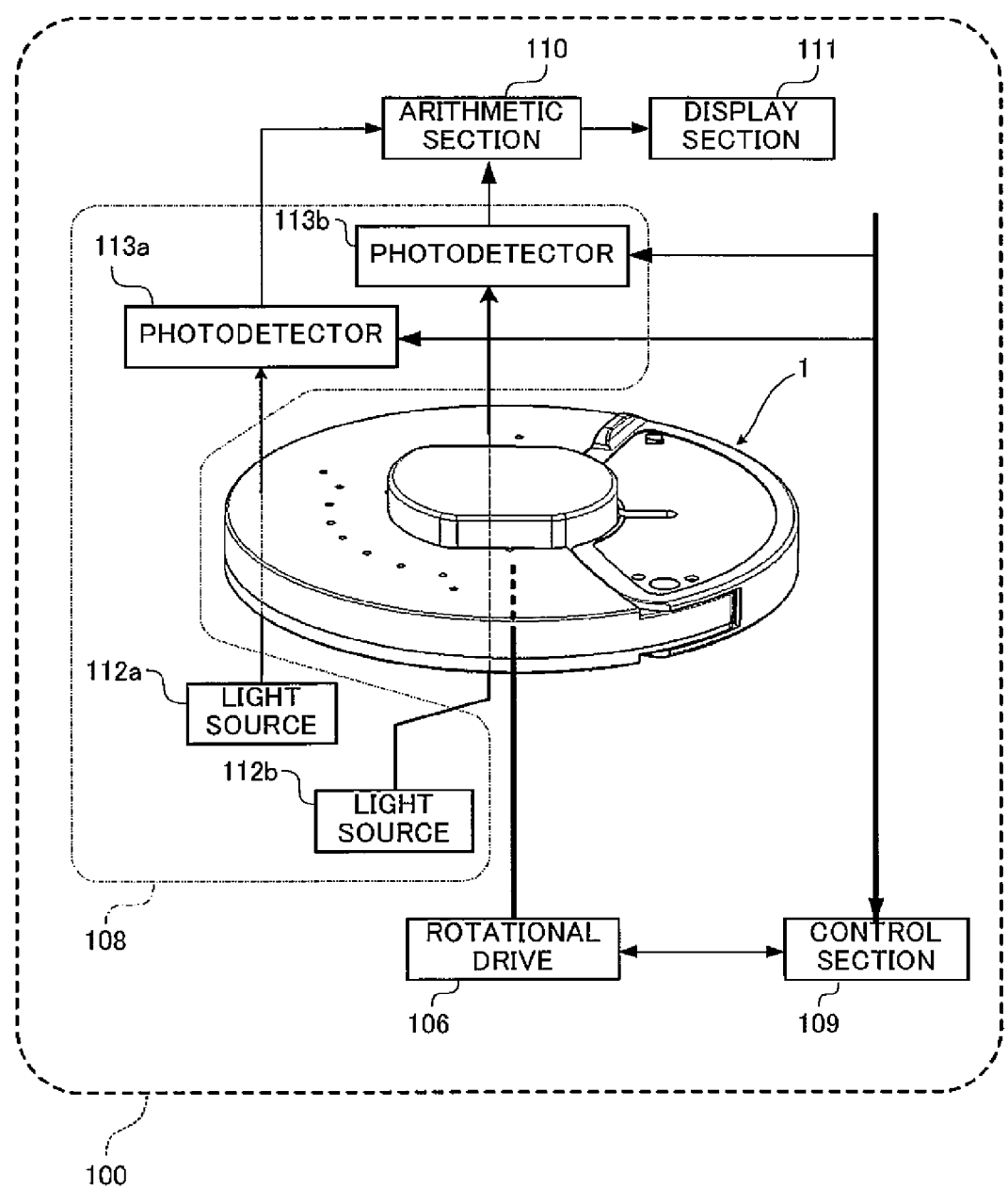
FIG. 32 is a structural diagram showing an analyzer according to the embodiment.

FIG. 32 shows the configuration of the analyzer 100.

The analyzer 100 is made up of the rotational drive 106 for rotating the rotor 101, an optical measurement section 108 acting as an analyzer that accesses and analyzes a reactant in the analyzing device 1, a control section 109 for controlling the rotation speed and direction of the rotor 101, the measurement timing of the optical measurement section 108, and so on, an arithmetic section 110 for calculating a measurement result by processing a signal obtained by the optical measurement section 108, and a display section 111 for displaying the result obtained by the arithmetic section 110.

The rotational drive 106 can rotate the analyzing device 1 about the rotation axis 107 in any direction at a predetermined rotation speed through the rotor 101 and can further vibrate the analyzing device 1 so as to laterally reciprocate the analyzing device 1 at a predetermined stop position with respect to the rotation axis 107 with a predetermined amplitude range and a predetermined period.

The optical measurement section 108 includes a light source 112a for emitting light to the measuring chamber of the analyzing device 1, a photodetector 113a for detecting an amount of light having passed through the analyzing device 1 out of the light emitted from the light source 112a, a light source 112b for emitting laser light to a measuring section provided in addition to the measuring chamber of the analyzing device 1, and a photodetector 113b for detecting an amount of light having passed through the analyzing device 1 out of the light emitted from the light source 112b.

The analyzing device 1 is rotationally driven by the rotor 101, and the sample liquid drawn into the analyzing device 1 from the inlet 13 is transferred in the analyzing device 1 by using a centrifugal force generated by rotating the analyzing device 1 about the rotation axis 107 located inside the inlet 13 and a capillary force of a capillary channel provided in the analyzing device 1. The microchannel structure of the analyzing device 1 will be specifically described below along with the analyzing process.

The configurations of the inlet 13 of the analyzing device 1 and a portion around the inlet 13 and configurations such as a guide portion 17, a capillary cavity 19, a recessed portion 21, a bending portion 22, a separating cavity 23, and a cavity 24 are similar to those of the first embodiment.

Figure 33:
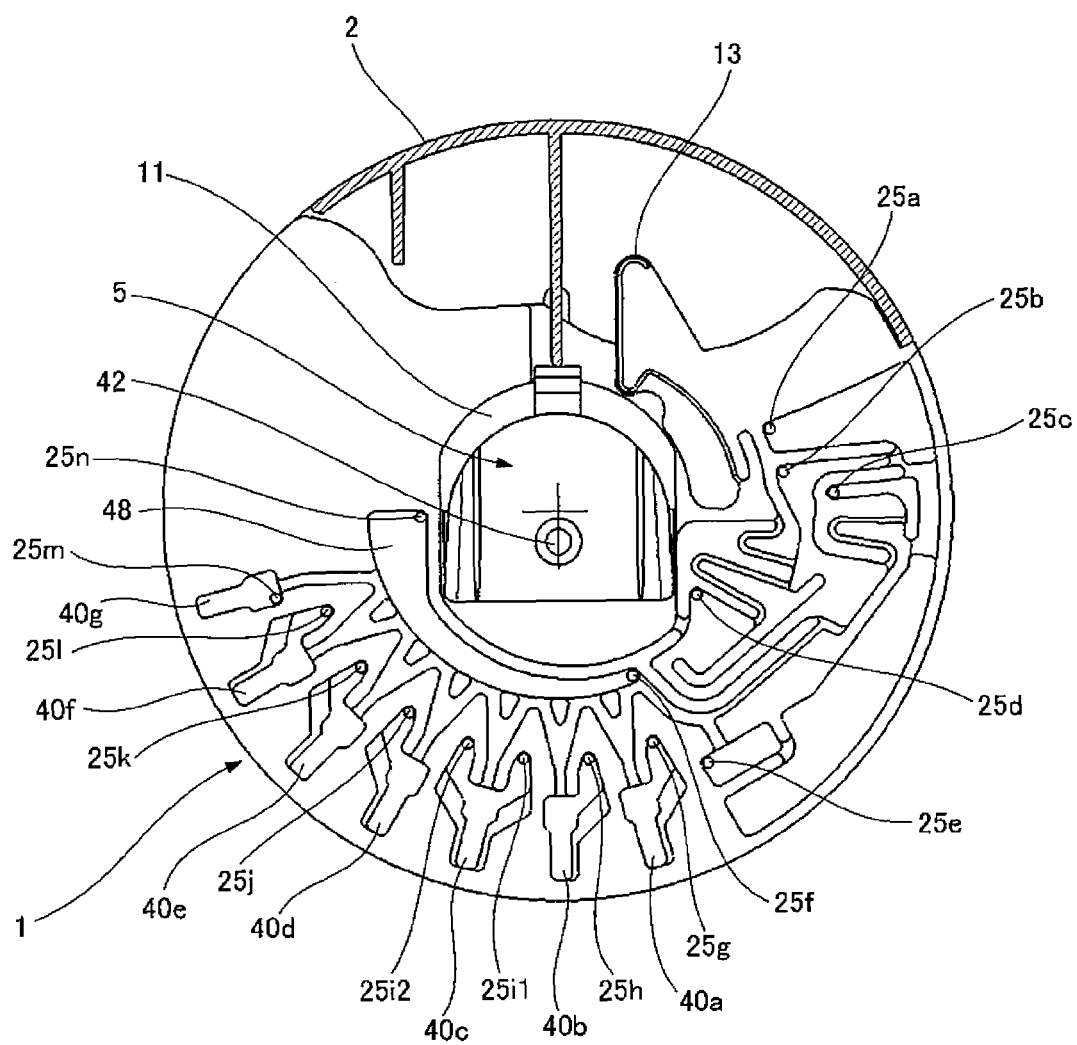
FIG. 33 is a sectional view showing a state before the analyzing device is set on the analyzer and is rotated.

With this configuration, blood dropped as a sample liquid 18 to the inlet 13 is drawn to the capillary cavity 19 through the guide portion 17. FIG. 33 shows a state before the analyzing device 1 containing the dropped sample liquid 18 is set on the rotor 101 and is rotated thereon. At this point, the aluminum seal 9 of the diluent container 5 has been collided with and broken by an opening rib 11a. Reference characters 25a to 25g, 25h, 25i1, 25i2, and 25j to 25n denote air holes formed on the base substrate 3.

Figure 34:
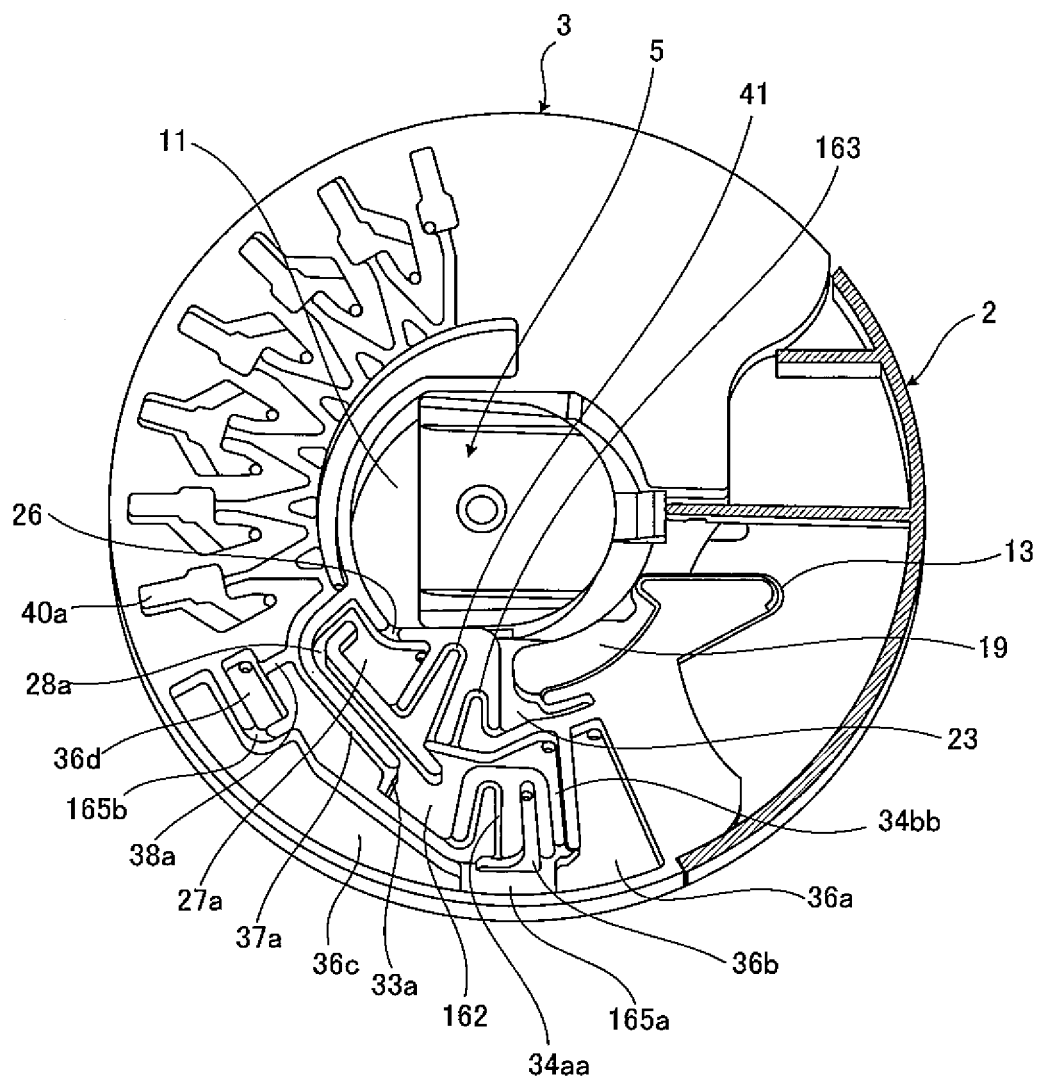
FIG. 34 is a perspective view showing a base substrate of the analyzing device.
Figure 35:
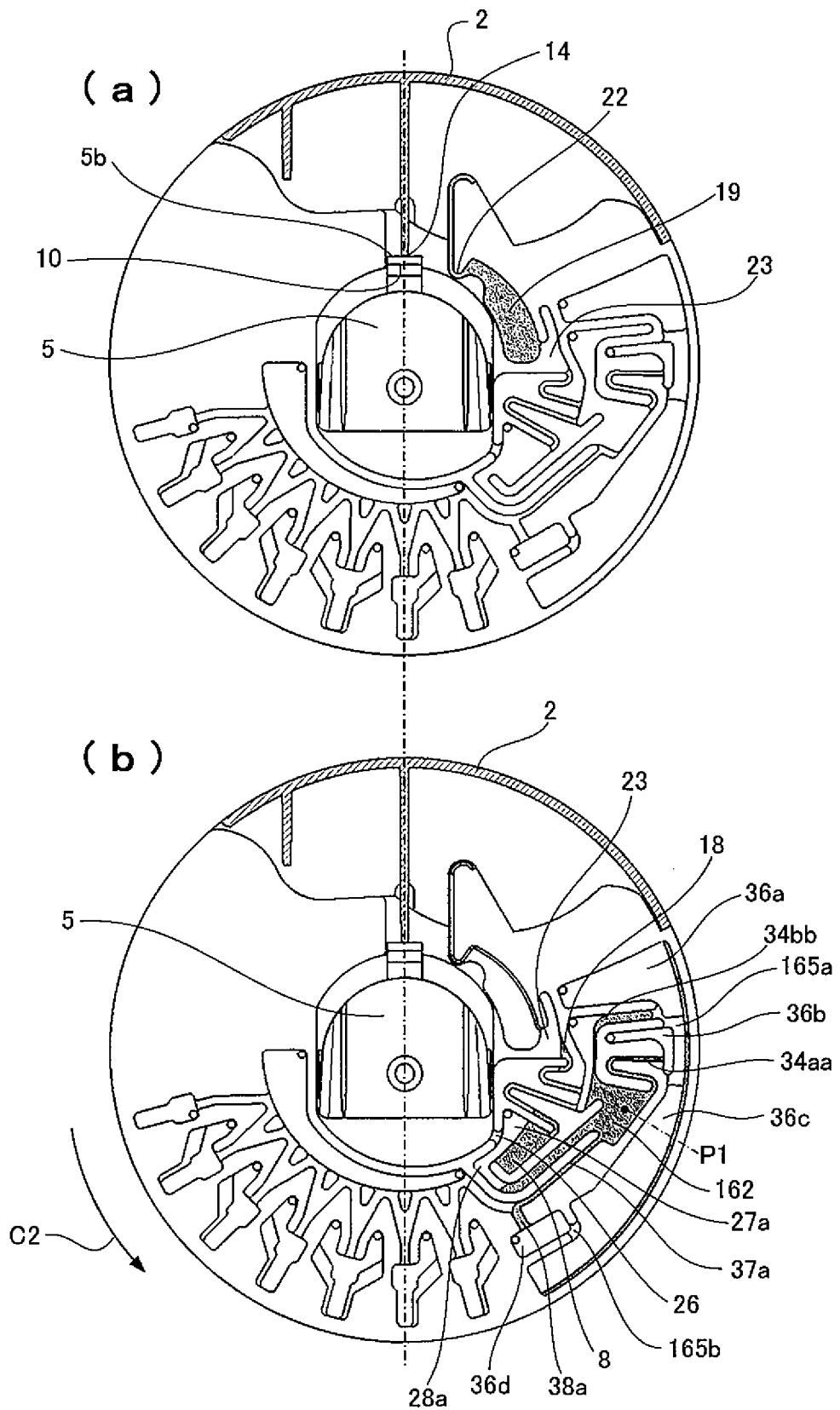
FIG. 35 is a sectional view showing a state after the analyzing device is set on the analyzer and is rotated and a state after centrifugal separation.
Figure 36:
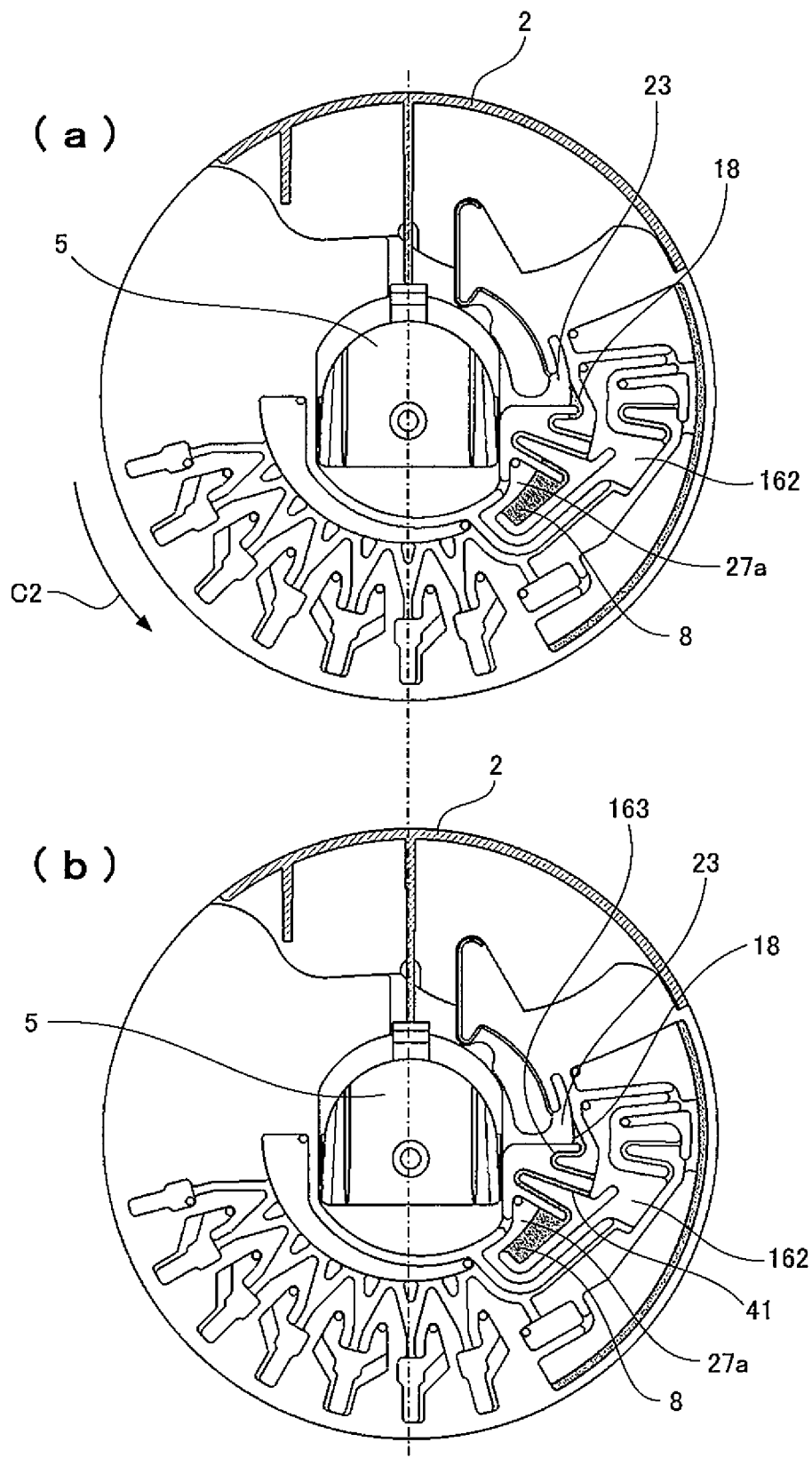
FIG. 36 is a sectional view showing a state when a solid component of a sample liquid is quantitatively collected and diluted after centrifugal separation.
Figure 37:
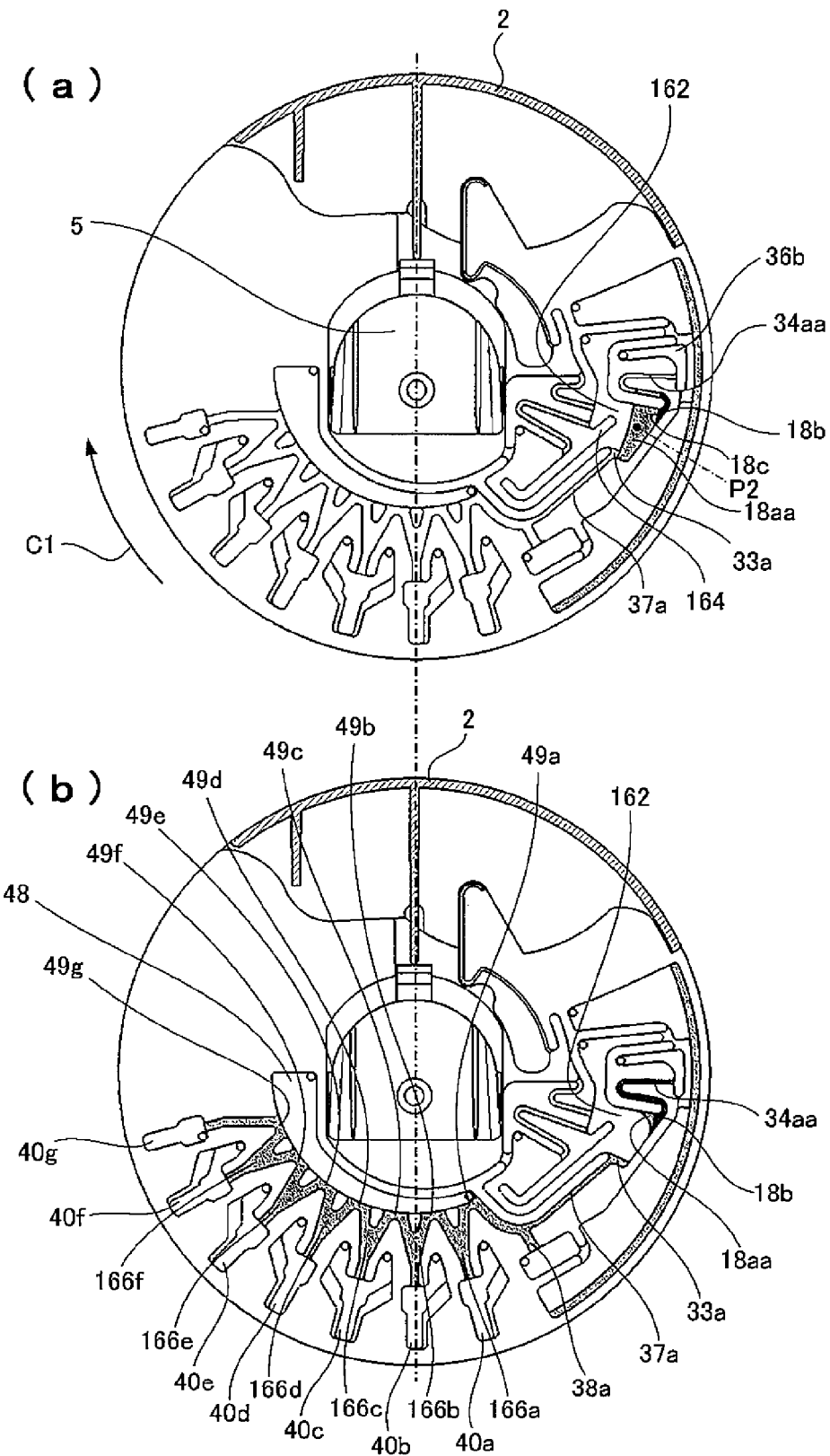
FIG. 37 is a sectional view of Step 4 and Step 5.

FIG. 34 shows the channels of the diluent from the diluent container 5 and a part around a mixing chamber 162 for stirring and mixing the diluent or the received diluent and the liquid sample.

In order to distribute the diluent from the diluent container storage part 11 to a diluent quantifying chamber 27a and the mixing chamber 162, a distributing channel is configured as follows:

The diluent quantifying chamber 27a disposed inside the mixing chamber 162 is connected to the diluent container storage part 11 via a discharge channel 26 to quantify a required amount of the received diluent and cause an excessive amount of the diluent to overflow. The excessive amount of the diluent from the diluent quantifying chamber 27a is distributed to the mixing chamber 162 through an overflow channel 28a. The outer periphery of the diluent quantifying chamber 27a is connected to the mixing chamber 162 via a connecting channel 41 having a siphon structure. The bottom of the outer periphery of the mixing chamber 162 communicates with an overflow cavity 36b, which has an inlet on the outer periphery of the mixing chamber 162, via a connecting channel 34aa having a siphon structure. The overflow cavity 36b is connected to overflow cavities 36a and 36c via a backflow preventing channel 165a formed in a clearance to which a capillary force is applied. Further, inside the innermost position of the siphon of the connecting channel 34aa, a connecting channel 34bb is provided to cause an excessive amount of the diluent in the mixing chamber 162 to overflow to the overflow cavity 36a.

The following will describe the analyzing process along with the configuration of the control section 109 for controlling the operation of the rotational drive 106.

Step 1

As shown in FIG. 35(a), the analyzing device 1 in which a sample liquid to be inspected is dropped to the inlet 13 is set on the rotor 101 in a state in which the sample liquid is retained in the capillary cavity 19 and the aluminum seal 9 of the diluent container 5 has been broken.

Step 2

The door 103 is closed and then the rotor 101 is rotationally driven in a clockwise direction (direction C2), so that the retained sample liquid overflows at the position of the bending portion 22. The sample liquid in the guide portion 17 is discharged into the protective cap 2, the sample liquid 18 in the capillary cavity 19 flows into the separating cavity 23 as shown in FIG. 35(b), and a fixed amount of the sample liquid is temporarily retained therein.

The diluent 8 from the diluent container 5 flows into the diluent quantifying chamber 27a through the discharge channel 26.

When the diluent 8 having flowed into the diluent quantifying chamber 27a exceeds a predetermined amount, the excessive diluent 8 flows into the mixing chamber 162 through the overflow channel 28a as shown in FIG. 35(b). Further, when the diluent 8 having flowed into the mixing chamber 162 exceeds a predetermined amount, the excessive diluent 8 flows into the overflow cavities 36a, 36b, and 36c, and an overflow cavity 36d through the connecting channels 34aa and 34bb and an overflow channel 38a. The diluent 8 having flowed into the overflow cavities 36a, 36b, and 36c is retained in the overflow cavities 36a, 36b, and 36c by the capillary forces of the backflow preventing channel 165a and a backflow preventing channel 165b.

In the fifth embodiment, a fixed amount of the sample liquid is retained in the separating cavity 23. An overflow channel (not shown) may be provided to measure an overflow of the sample liquid, which exceeds a predetermined amount, from the separating cavity when the unmeasured sample liquid is supplied into the capillary cavity 19 and then is transferred into the separating cavity 23.

In this configuration, the diluent 8 is a solution having a specified absorbance in a specific wave range. The absorbance of the diluent 8 is measured (primary photometry)

while the diluent 8 having flowed into the mixing chamber 162 is retained in the mixing chamber 162. To be specific, when the analyzing device 1 is rotationally driven in the clockwise direction (direction C2) and the mixing chamber 162 containing only the diluent 8 passes between the light source 112b and the photodetector 113b, the arithmetic section 110 reads a detected value of the photodetector 113b. P1 in FIG. 35(b) indicates the light transmission position of the primary photometry.

The connecting channel 34aa has a siphon structure including a bending portion formed from the outermost part to the inner periphery of the mixing chamber 162. When the diluent 8 exceeds the bending portion of the connecting channel 34aa, the diluent 8 in the mixing chamber 162 is discharged into the overflow cavities 36a, 36b, and 36c by a siphon effect. Further, by providing the connecting channel 34bb inside the connecting channel 34aa to discharge the diluent exceeding a predetermined amount, it is possible to prevent the excessive diluent from flowing into the separating cavity 23 from the mixing chamber 162.

The diluent 8 retained in the mixing chamber 162 is completely discharged to the overflow cavities 36a, 36b, and 36c with the passage of time. As shown in FIG. 36(a), a predetermined amount of the sample liquid 18 and a predetermined amount of the diluent 8 are retained in the separating cavity 23 and the diluent quantifying chamber 27a, respectively.

Step 3

Next, when the rotation of the rotor 101 is stopped, as shown in FIG. 36(b), a first connecting channel 163 having a siphon shape connecting the separating cavity 23 and the mixing chamber 162 is primed with the sample liquid 18. Similarly, the connecting channel 41 having a siphon shape connecting the diluent quantifying chamber 27a and the mixing chamber 162 is primed with the diluent 8.

Step 4

When the rotor 101 is rotationally driven in a counterclockwise direction (direction C1), as shown in FIG. 37(a), the sample liquid 18 of the separating cavity 23 and the diluent 8 of the diluent quantifying chamber 27a flow into the mixing chamber 162 and are centrifugally separated into a diluted plasma component 18aa and a blood cell component 18b in the mixing chamber 162. Reference character 18c denotes the separation interface of the diluted plasma component 18aa and the blood cell component 18b. The sample liquid 18 and the diluent 8 collide with a rib 164 once and then flow into the mixing chamber 162, so that the plasma component in the sample liquid 18 and the diluent 8 can be uniformly stirred.

Next, the absorbance of the diluted plasma component 18aa centrifugally separated in the mixing chamber 162 is measured (secondary photometry). To be specific, the analyzing device 1 is rotationally driven in the counterclockwise direction (direction C1) and the arithmetic section 110 reads a detected value of the photodetector 113b when the mixing chamber 162 containing the diluted plasma component 18aa passes between the light source 112b and the photodetector 113b. P2 in FIG. 37(a) indicates the light transmission position of the secondary photometry. The secondary photometry position P2 in the mixing chamber 162 is located at the same position as the primary photometry position P1 of FIG. 35(b).

Even when the primary photometry position P1 and the secondary photometry position P2 are not aligned with each other, higher measurement accuracy can be expected than in the prior art because the single mixing chamber 162 is measured in both of the measurements. However, measurements at the same position are more desirable.

In the fifth embodiment, blood serving as the sample liquid 18 and the diluent 8 are directly mixed and then the diluted plasma component 18aa is extracted. Further, the diluted plasma component 18aa is reacted with a reagent to analyze a specific component in the plasma component. The ratio of a plasma component in blood varies among individuals and thus the dilution factor of the plasma component greatly varies during direct mixing. Hence, in a reaction of the diluted plasma component 18aa and the reagent, a reaction concentration varies and affects the measurement accuracy. In order to correct the variations in dilution factor at the mixing of the sample liquid 18 and the diluent 8, a diluent having a specified absorbance in a specific wave range is used and an absorbance is measured at the same point of the mixing chamber 162 before and after the mixing with the sample liquid to calculate a dilution factor. Thus it is possible to eliminate variations in the optical path length of the measuring section and eliminate fluctuations in the amount of received light, the fluctuations being caused by the uneven surface (waviness, surface roughness) of the measuring section. Consequently, it is possible to achieve measurement with an accurate dilution factor and correct variations in dilution factor for measurement results in the measuring chamber, thereby remarkably improving the measurement accuracy. This correction method is also useful for correcting variations in diluent factor when the variations are caused by varying amounts of the sample liquid 18 and the diluent 8.

Step 5

Next, when the rotation of the rotor 101 is stopped, the diluted plasma component 18aa is sucked by a capillary cavity 33a formed on the wall surface of the mixing chamber 162 and flows into, as shown in FIG. 37(b), the overflow channel 38a and measurement channels 166a, 166b, 166c, 166d, 166e, and 166f through a capillary channel 37a communicating with the capillary cavity 33a, and fixed amounts of the diluted plasma component 18aa are retained in the measurement channels 166a to 166f.

Figure 38A:
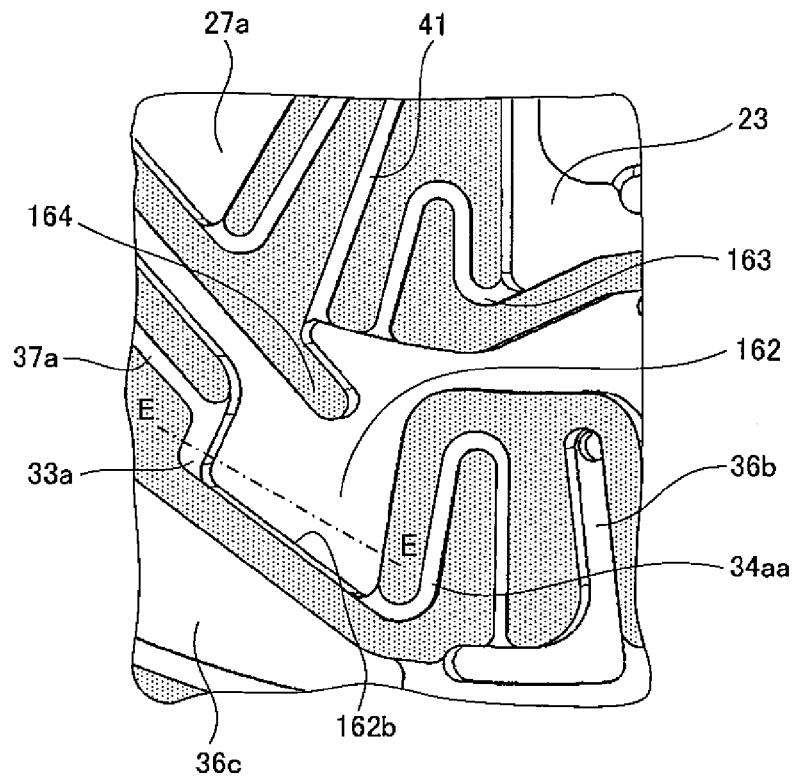
Figure 38B:
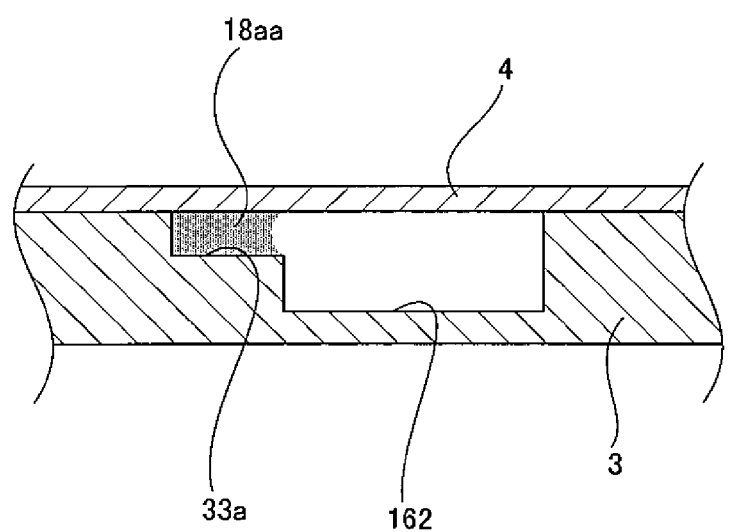
FIG. 38B is an E-E sectional view of FIG. 38A.
Figure 39:
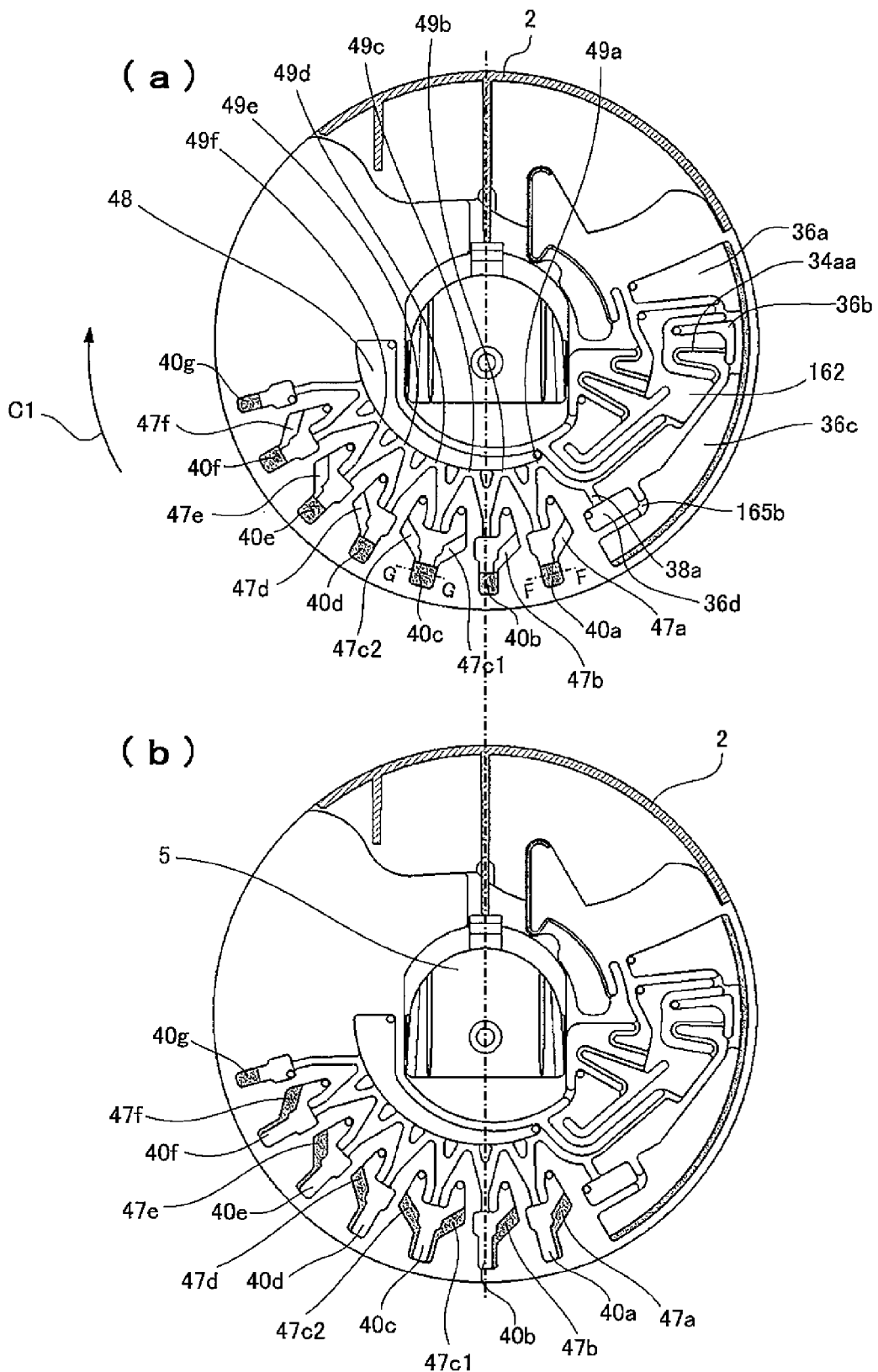
FIG. 39 is a sectional view of Step 6 and Step 7.

FIG. 38A is a perspective view showing the capillary cavity 33a and a portion around the capillary cavity 33a. FIG. 38B is an E-E sectional view of FIG. 38A. The following will specifically describe the capillary cavity 33a and the portion around the capillary cavity 33a.

The capillary cavity 33a is formed from a bottom 162b of the mixing chamber 162 to the inner periphery. In other words, the outermost position of the capillary cavity 33a is formed to the outside of the separation interface 18c of the diluted plasma component 18aa and the blood cell component 18b of FIG. 37(a). By setting the position of the outer periphery of the capillary cavity 33a thus, the outer end of the capillary cavity 33a is immersed in the diluted plasma component 18aa and the blood cell component 18b that have been separated in the mixing chamber 162. Since the diluted plasma component 18aa has a lower viscosity than the blood cell component 18b, the diluted plasma component 18aa is first sucked by the capillary cavity 33a. The diluted plasma component 18aa can be transferred to measuring chambers 40a to 40f, and 40g through the capillary channel 37a, the overflow channel 38a, and the measurement channels 166a, 166b, 166c, 166d, 166e, and 166f.

After the diluted plasma component 18aa is sucked, the blood cell component 18b is also sucked following the diluted plasma component 18aa. Thus the diluted plasma component 18aa can be replaced with the blood cell component 18b in the capillary cavity 33a and a path halfway to the capillary channel 37a. When the overflow channel 38a and the measurement channels 166a to 166f are filled with the diluted plasma component 18aa, the transfer of the liquid is stopped also in the capillary channel 37a and the capillary cavity 33a, so that the blood cell component 18b does not enter the overflow channel 38a and the measurement channels 166a to 166f.

Hence, it is possible to minimize a loss of the transferred liquid as compared with the configuration of the prior art, thereby reducing an amount of the sample liquid required for measurement.

Step 6

Further, when the rotor 101 is rotationally driven in the counterclockwise direction (direction C1), as shown in FIG. 39(a), the diluted plasma component 18aa retained in the measurement channels 166a to 166f overflows at the positions of bending portions 49a, 49b, 49c, 49d, 49e, 49f, and 49g that are connected to an atmosphere open cavity 48 communicating with the atmosphere, and then the diluted plasma component 18aa flows into the measuring chambers 40a to 40f, and 40g. At this point, equal amounts of the diluted plasma component 18aa flow into the respective measuring chambers 40a to 40f.

Moreover, the diluted plasma component 18aa of the overflow channel 38a at this point flows into the overflow cavities 36c and 36a through the overflow cavity 36d and the backflow preventing channel 165b. Further, the sample liquid in the mixing chamber 162 at this point flows into the overflow cavities 36a and 36c through the siphon-shaped connecting channel 34aa and the overflow cavity 36b.

The measuring chambers 40a to 40f and 40g are formed to extend in a direction along which a centrifugal force is applied. To be specific, the measuring chambers are extended from the rotation center of the analyzing device 1 to the outermost periphery and have small widths in the circumferential direction of the analyzing device 1. The bottoms of the outer sides of the multiple measuring chambers 40a to 40f and 40g are arranged at the same radius of the analyzing device 1. Thus the measurements of the multiple measuring chambers 40a to 40f and 40g do not require the multiple light sources 112a of the same wavelength at different radius distances and the photodetectors 113a corresponding to the light sources 112a, thereby reducing the cost of the device. Since measurements can be conducted using different wavelengths in the same measuring chamber, the sensitivity of measurement can be improved by selecting the optimum wavelength according to the concentration of a mixed solution.

Figure 41:
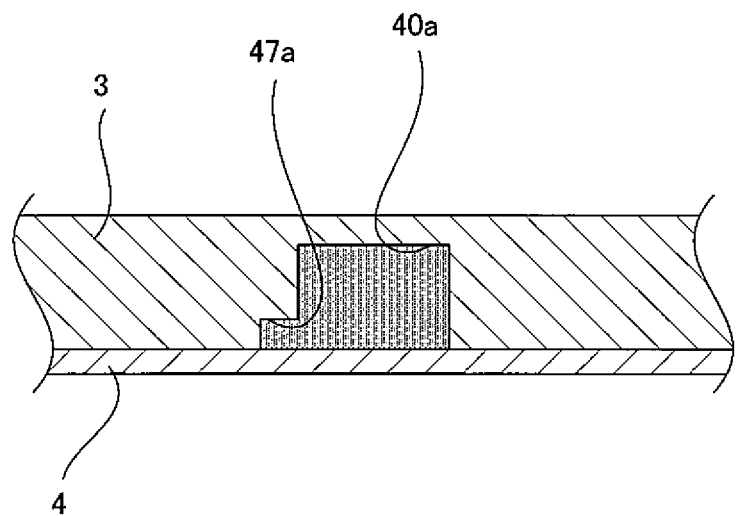
FIG. 41 is an F-F sectional view of FIG. 39.

On one side walls of the measuring chambers 40a, 40b, and 40d to 40f in the circumferential direction, capillary areas 47a, 47b, 47d, 47e, and 47f are formed so as to extend from the outer periphery positions of the measuring chambers to the inner periphery. FIG. 41 is an F-F sectional view of FIG. 39(a).

Figure 42:
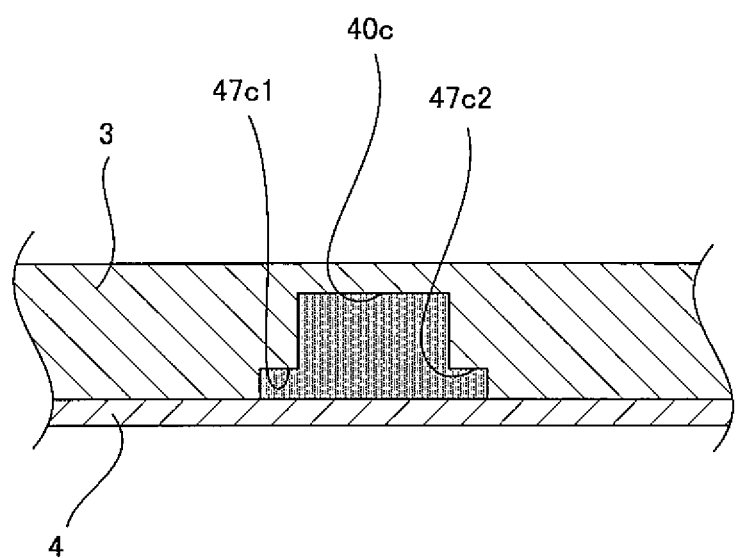
FIG. 42 is a G-G sectional view of FIG. 39.

On both side walls of the measuring chamber 40c in the circumferential direction, capillary areas 47c1 and 47c2 are formed so as to extend from the outer periphery position of the measuring chamber to the inner periphery. FIG. 42 is a G-G sectional view of FIG. 39(a).

Unlike in the measuring chambers 40a to 40f, a capillary area is not formed in the measuring chamber 40g.

The suction capacity of the capillary area 47a is not so large as to completely store the sample liquid retained in the measuring chamber 40a. Similarly, the capacities of the capillary areas 47b and 47d to 47f are not so large as to completely store the sample liquid retained in the measuring chambers 40b and 40d to 40f. As to the capillary areas 47c1 and 47c2 of the measuring chamber 40c, the sum of the suction capacities of the capillary area 47c1 and the capillary area 47c2 is large enough to completely store the sample liquid retained in the measuring chamber 40c. The measuring chambers 40b to 40f and 40g have equal optical path lengths.

Figure 40:
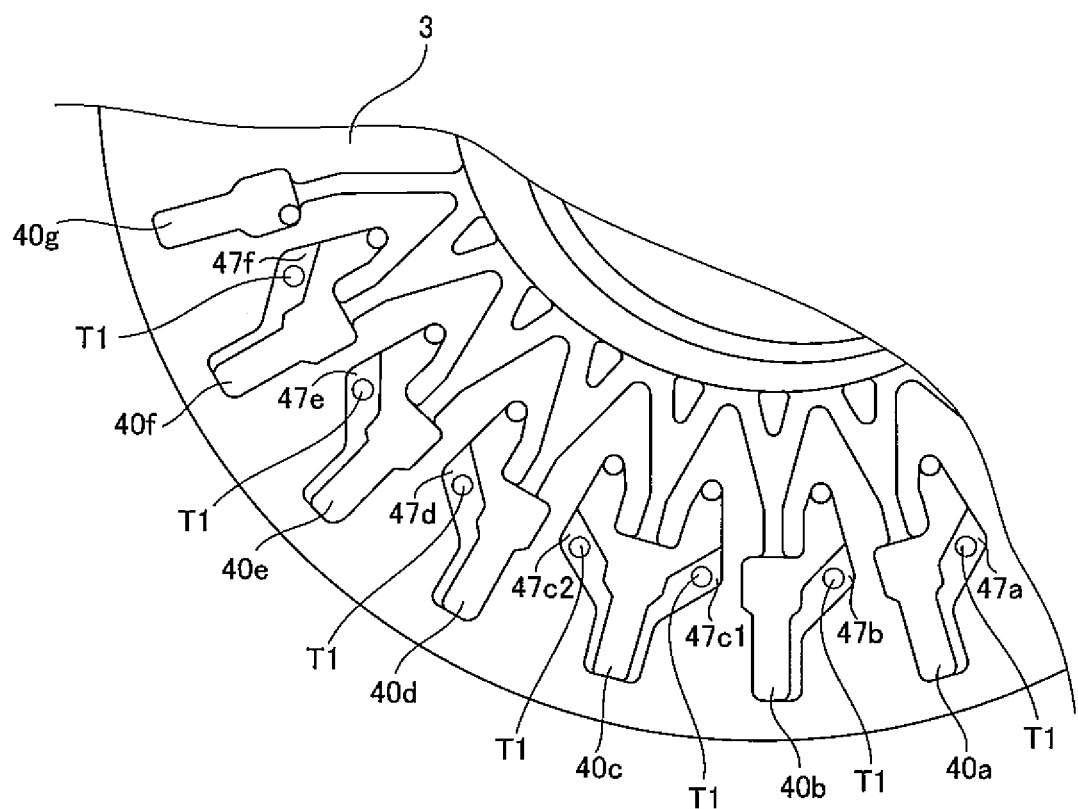
FIG. 40 is an enlarged plan view showing measuring chambers 40a to 40f of FIG. 33.

As shown in FIG. 40, the capillary areas 47a, 47b, 47c1, 47c2, 47d, 47e, and 47f each contain a reagent T1 to be reacted with the sample liquid. The measuring chamber 40g does not contain any reagents.

In the fifth embodiment, the reagent T1 contained in the capillary areas 47a, 47b, 47c1, 47c2, and 47d to 47f varies according to specific components to be analyzed. Soluble reagents are contained in the capillary areas 47a, 47b, and 47d to 47f and a less soluble reagent is contained in the capillary area 47c.

Step 7

Next, the rotation of the analyzing device 1 is slowed or stopped or the analyzing device 1 is vibrated so as to laterally reciprocate at a predetermined stop position with respect to the rotation axis 107 with a predetermined amplitude range and a predetermined period, so that the sample liquid transferred to the measuring chambers 40a to 40f or a mixed solution of the reagent and the sample liquid is sucked by the capillary areas 47a to 47f by a capillary force as shown in FIG. 39(b). At this point, the reagent T1 starts melting and a reaction of the specific component contained in the diluted plasma component 18aa and the reagent is started.

Step 8

As shown in FIG. 39(b), from a state in which the sample liquid or the mixed solution of the reagent and the sample liquid is sucked to the capillary areas 47a to 47f, the rotation of the analyzing device 1 is accelerated to be rotationally driven in the counterclockwise direction (direction C1) or the clockwise direction (direction C2). Thus as shown in FIG. 39(a), the liquid retained in the capillary areas 47a to 47f is transferred to the outer peripheries of the measuring chambers 40a to 40f by a centrifugal force, so that the reagent T1 and the diluted plasma component 18aa are stirred.

In this case, the repeated operations of step 7 and step 8 accelerate stirring of the reagent and the diluted plasma component 18aa. Thus it is possible to reliably stir the reagent and the diluted plasma component 18aa in a short time as compared with stirring only by diffusion.

Step 9

When the analyzing device 1 is rotationally driven in the counterclockwise direction (direction C1) or the clockwise direction (direction C2) and the measuring chambers 40a to 40f and 40g pass between the light source 112a and the photodetector 113a, the arithmetic section 110 reads a detected value of the photodetector 113a and corrects the detected value according to the results of the primary photometry and the secondary photometry to calculate the concentration of a specific component.

The measurement result of the measuring chamber 40g is used as the reference data of the measuring chambers 40a to 40f during computations in the arithmetic section 110.

Figure 45:
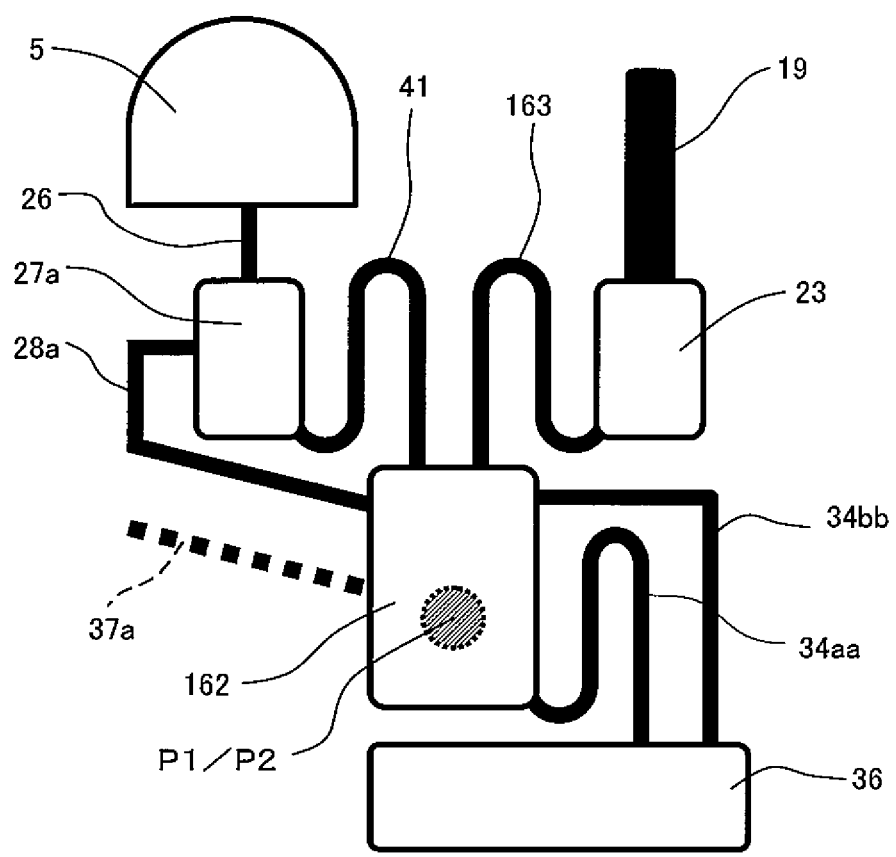
FIG. 45 is a schematic diagram showing a part around a mixing chamber 162 of FIG. 34.
Figure 46:
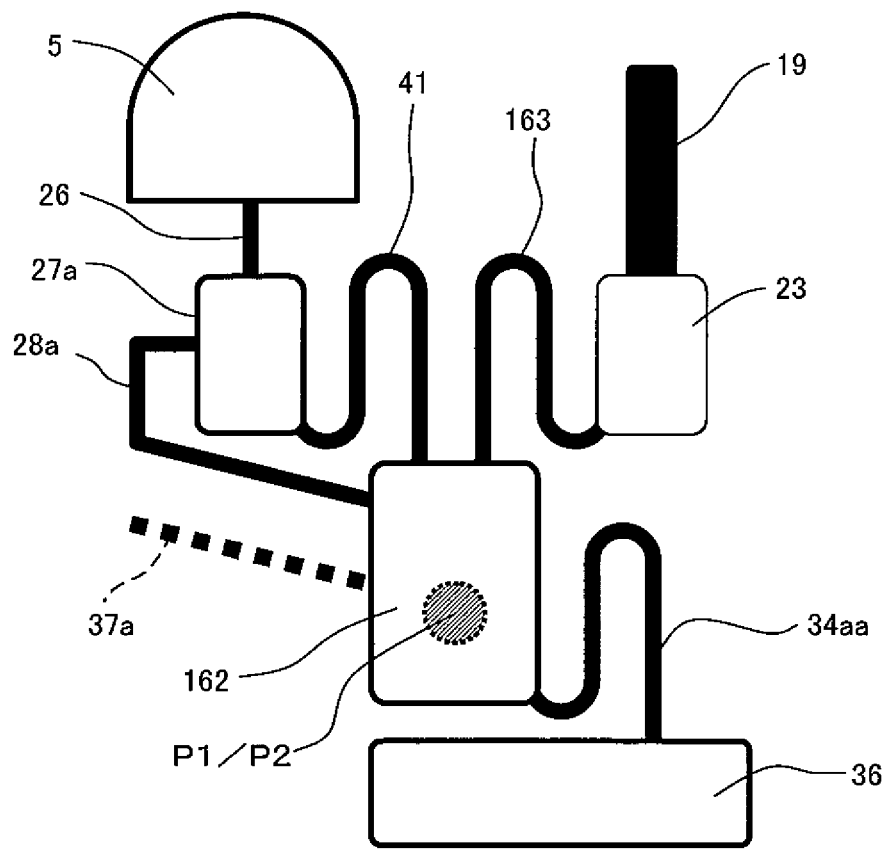
FIG. 46 is a schematic diagram showing another embodiment of the part around the mixing chamber 162.

In the fifth embodiment, as shown in FIG. 45, the diluent overflowing from the diluent quantifying chamber 27a is transferred to the mixing chamber 162 through the overflow channel 28a, and the absorbance of the diluent is measured while the transferred diluent is discharged from the mixing chamber 162 to an overflow cavity 36 (the overflow cavities 36a, 36b, 36c, and 36d and the backflow preventing channels 165a and 165b) through the connecting channels 34aa and 34bb. The same effect can be obtained even when the connecting channel 34bb of FIG. 45 is omitted as shown in FIG. 46.

Figure 47:
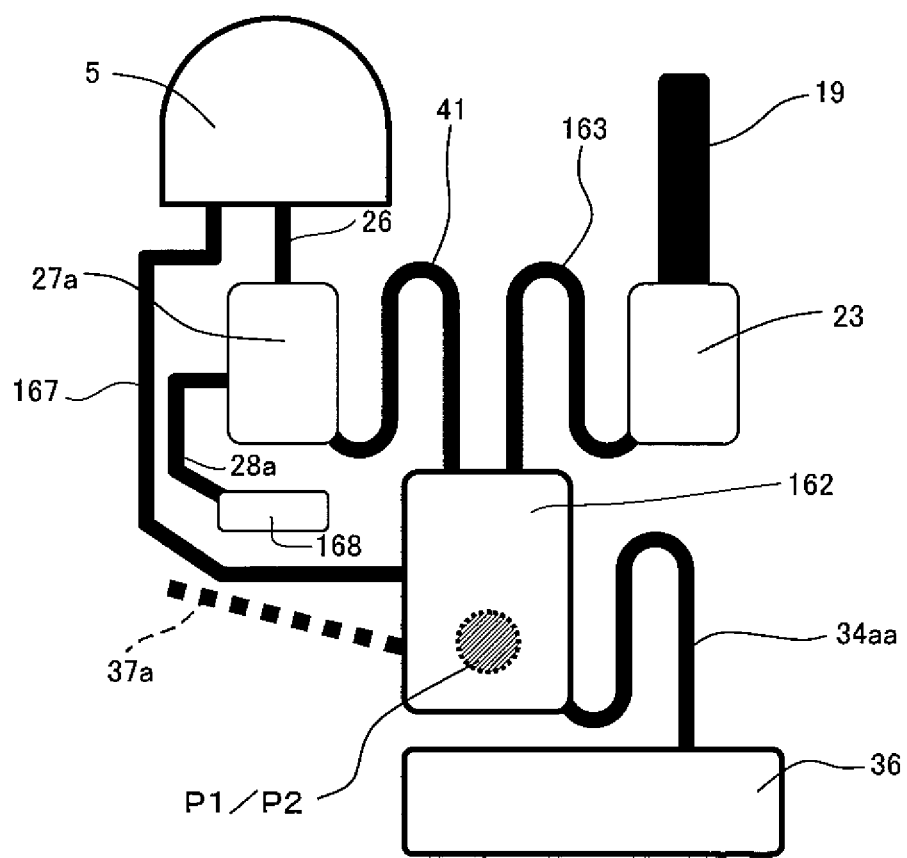
FIG. 47 is a schematic diagram showing still another embodiment of the part around the mixing chamber 162.

As shown in FIG. 47, the diluent container storage part 11 and the mixing chamber 162 may be connected via a connecting channel 167 instead of the diluent quantifying chamber 27a, and the diluent transferred from the diluent container 5 may be distributed to the diluent quantifying chamber 27a and the mixing chamber 162. Reference numeral 168 denotes an overflow chamber for storing the diluent passing through the overflow channel 28a.

Figure 48:
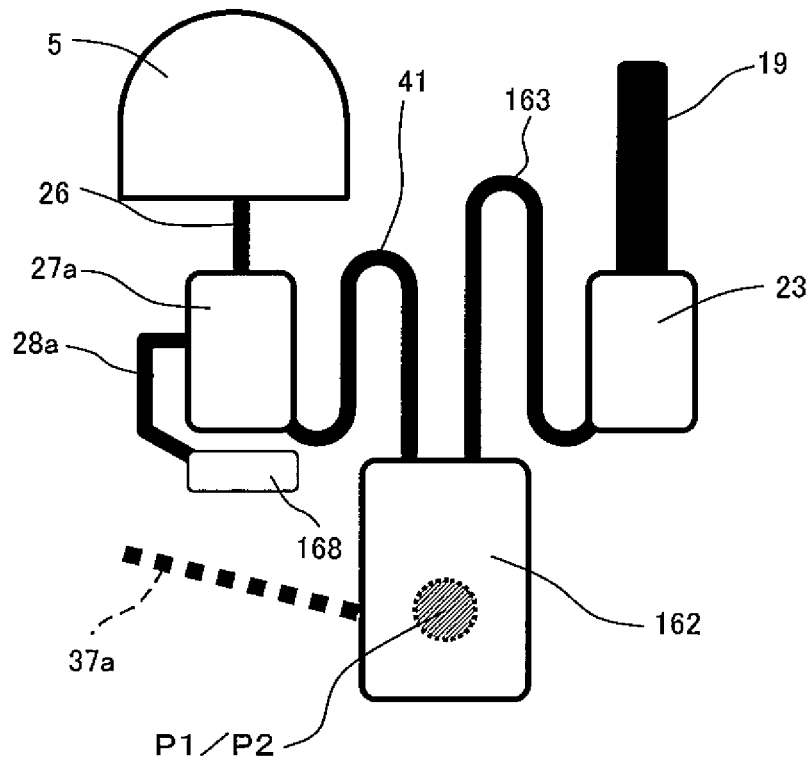
FIG. 48 is a schematic diagram showing still another embodiment of the part around the mixing chamber 162.

Further, as shown in FIG. 48, the siphon bending portion of the first connecting channel 163 is located inside the siphon bending portion of the connecting channel 41. After the quantification of the diluent, the rotation of the analyzing device 1 is slowed and the number of revolutions is controlled so as to transfer only the diluent over the bending portion of the siphon to the mixing chamber 162, so that only the diluent can be first retained and measured in the mixing chamber 162. In FIG. 48, the siphon bending portion of the first connecting channel 163 is located inside the siphon bending portion of the connecting channel 41. By optionally setting the relationship between a capillary force and a centrifugal force that are applied to each liquid retained in the first connecting channel 163 and the connecting channel 41, the liquid in the connecting channel 41 first passes through the siphon bending portion. Thus the positional relationship between the siphon bending portions of the first connecting channel 163 and the connecting channel 41 is not always limited. Parameters for setting the relationship between a capillary force and a centrifugal force include a channel width, a channel depth, a liquid density, the levels of liquids retained in the separating cavity 23 and the diluent quantifying chamber 27a (a fluid volume and the width and depth of each chamber), the radial position of the liquid level, and the number of revolutions.

As previously mentioned, a user can open the diluent container 5 by opening/closing the protective cap 2 at the collection of a sample liquid, and transfer the diluent into the analyzing device 1. Thus it is possible to simplify the analyzer, reduce the cost, and improve operability for the user.

Further, the diluent container 5 sealed with the aluminum seal 9 serving as a sealing member is used and the diluent container 5 is opened by breaking the aluminum seal 9 with the opening rib 11a serving as a protruding portion. Thus the diluent does not evaporate or decrease in amount during long-term storage, thereby improving the accuracy of analysis.

The widths of the measuring chambers 40a to 40f and 40g (dimensions in the circumferential direction) formed to extend in the centrifugal direction (radial direction) of the analyzing device 1 are regulated to the minimum dimensions detectable by the optical measurement section 108, and the levels of liquids retained in the measuring chambers 40a to 40f and 40g during rotation are regulated to radial positions detectable by the optical measurement section 108, that is, liquid levels filling a laser radiation area, so that a measurement can be conducted with the minimum fluid volume.

As previously mentioned, steps 7 to 9 are performed in a state in which the measuring chambers 40a to 40f are formed to extend in a direction along which a centrifugal force is applied and the capillary areas 47a to 47f are formed on at least one side walls arranged in a rotation direction and extend from the outer periphery positions to the inner peripheries of the measuring chambers 40a to 40f. Thus it is possible to obtain a sufficient stirring effect and reduce the size of the analyzing device without providing a U-shaped stirring mechanism of Patent Document 1 in which an inlet passage 114, a measurement cell 115, and a channel 117 are provided for stirring a sample liquid and a reagent.

The measuring chambers 40a to 40f and 40g are formed to extend in a direction along which a centrifugal force is applied. Thus the amount of the sample liquid filling the measuring chambers is smaller than that of Patent Document 1 and a measurement can be conducted with a small amount of the sample liquid.

Figure 43:
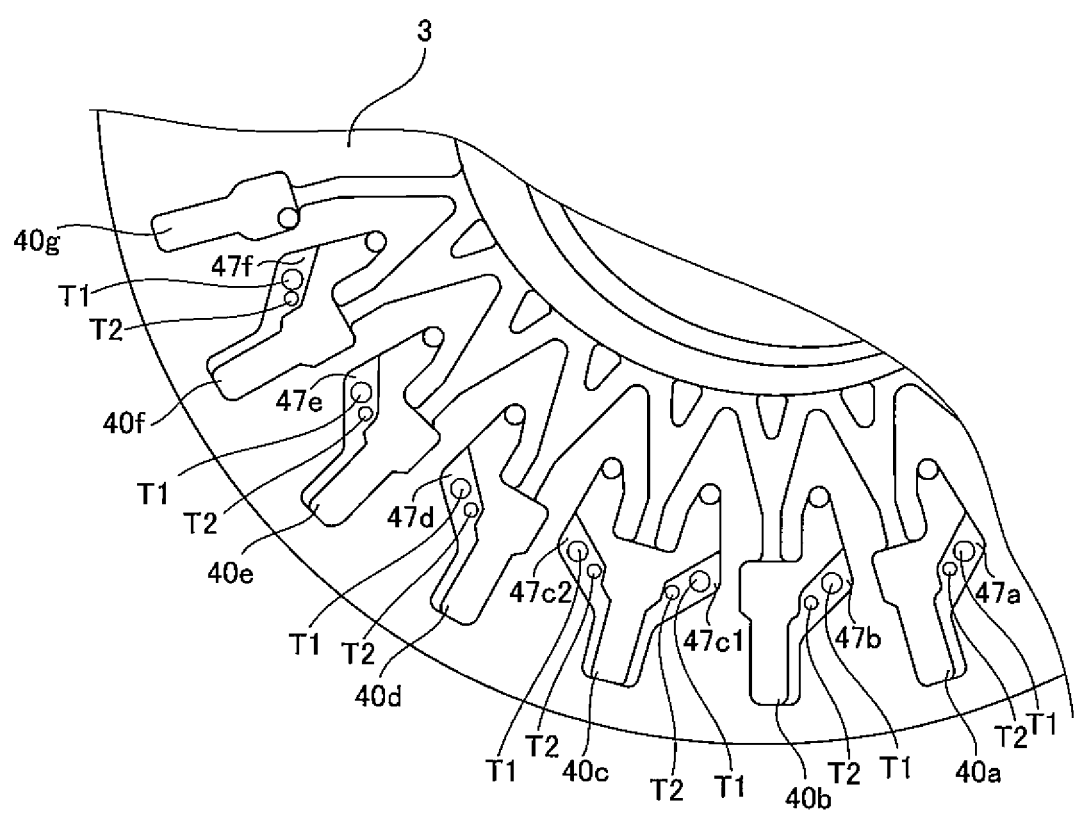
FIG. 43 is an enlarged plan view showing another example of the measuring chambers 40a to 40f.
Figure 44:
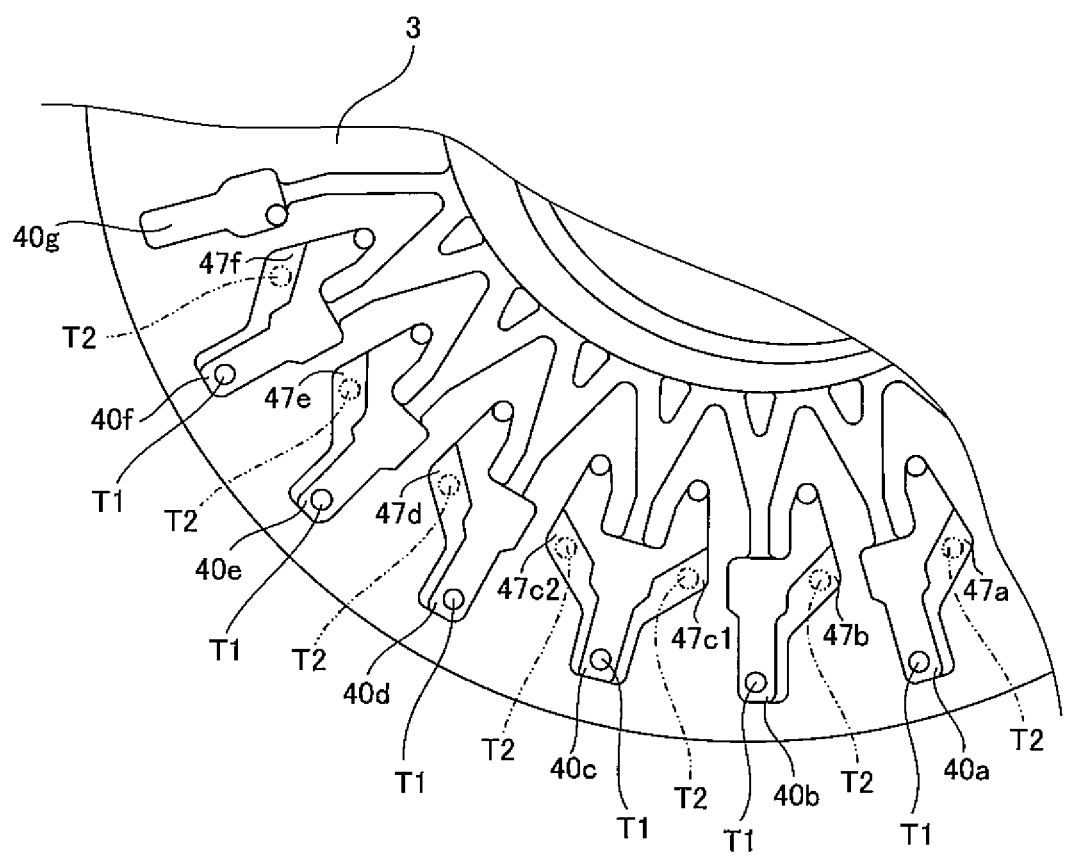
FIG. 44 is an enlarged plan view showing still another example of the measuring chambers 40a to 40f.

In the fifth embodiment, the reagent T1 is retained in the capillary areas 47a to 47f. As shown in FIG. 43, the capillary areas 47a to 47f may contain the reagent T1 and a reagent T2 that is different from the reagent T1. Further, as shown in FIG. 44, the reagent T1 may be provided around the bottoms of the outer peripheries of the measuring chambers 40a to 40f and the reagent T2 may be contained in the capillary areas 47a, 47b, 47c1, 47c2, and 47d to 47f when necessary as indicated by virtual lines. When the reagent T1 is provided on the bottom of one of the measuring chambers and the reagent T2 is provided in the capillary area, the reagent T1 and the reagent T2 may contain the same component or different components. The reagent T2 provided in the capillary areas may be multiple reagents containing different components.

Sixth Embodiment

In the fifth embodiment, the branch points are provided on the same circumference, whereas in a sixth embodiment, variations in liquid volume can be eliminated without providing branch points on the same circumference.

Referring to FIGS. 49 to 58, the sixth embodiment of the present invention will be described below.

Figure 57:
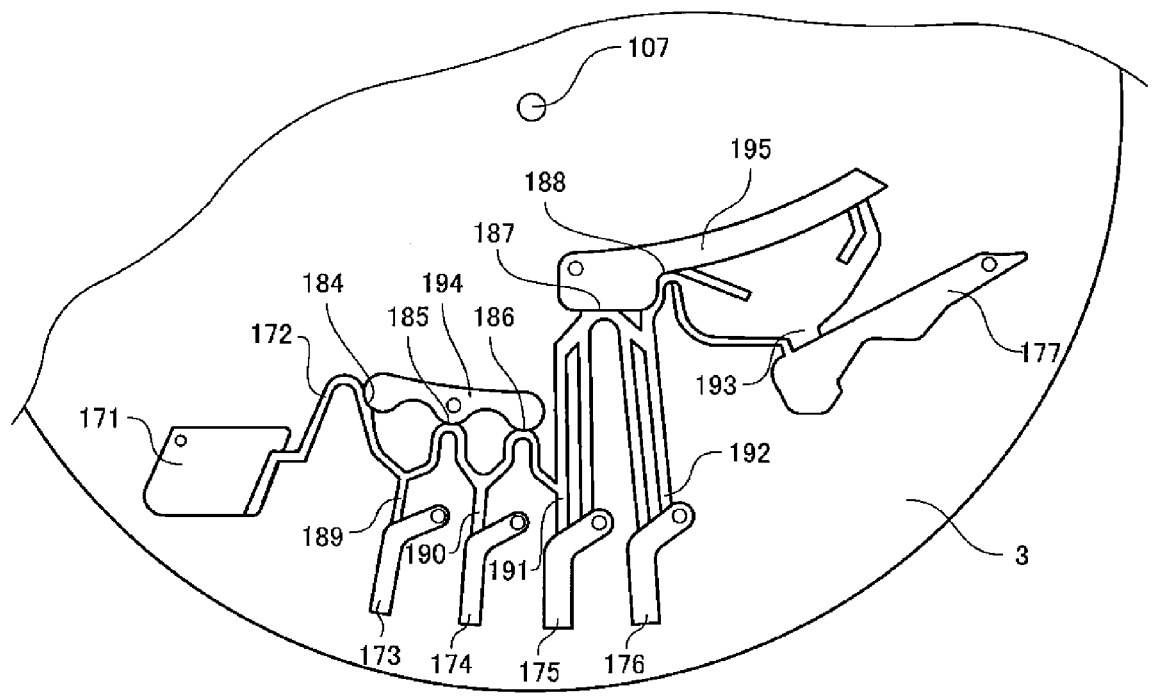
FIG. 57 is a top view showing a base substrate of an analyzing device according to a comparative example.
Figure 58:
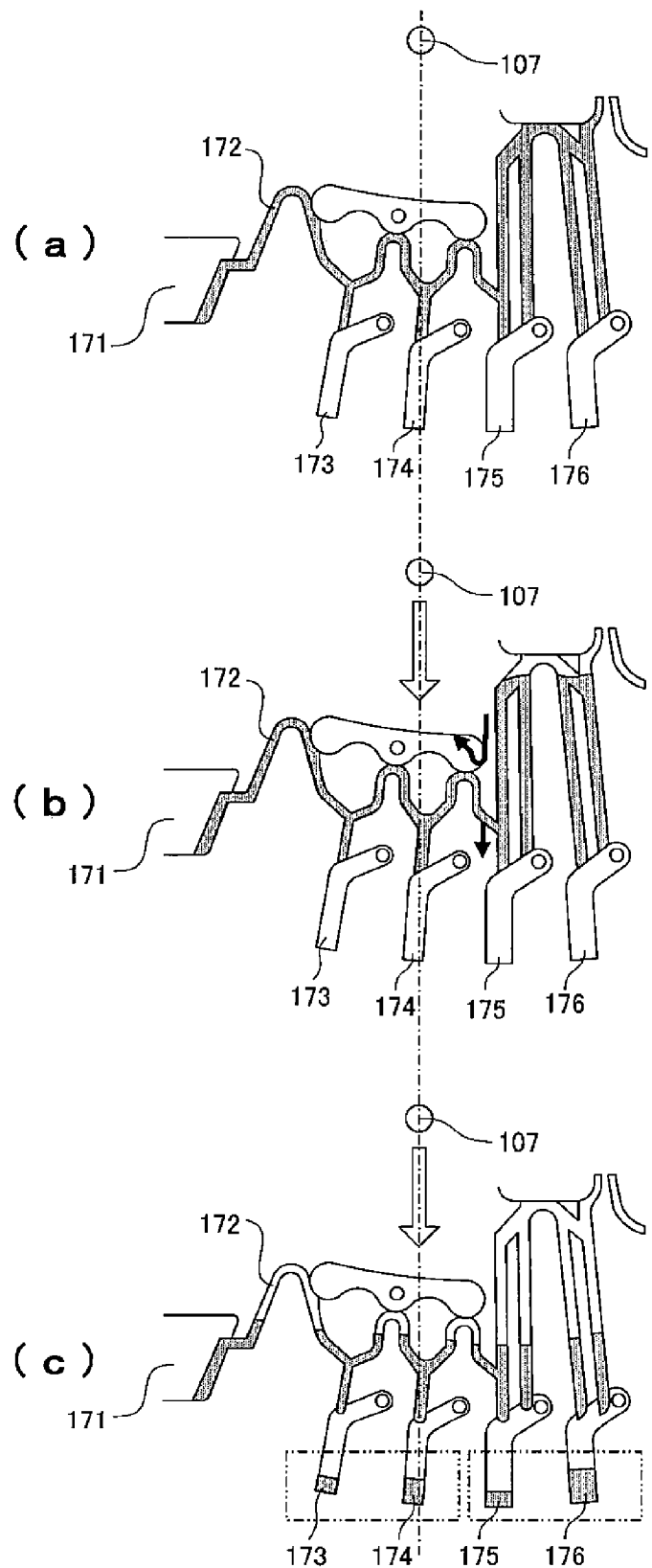
FIG. 58 is a flow pattern diagram of the comparative example.
Figure 59A:
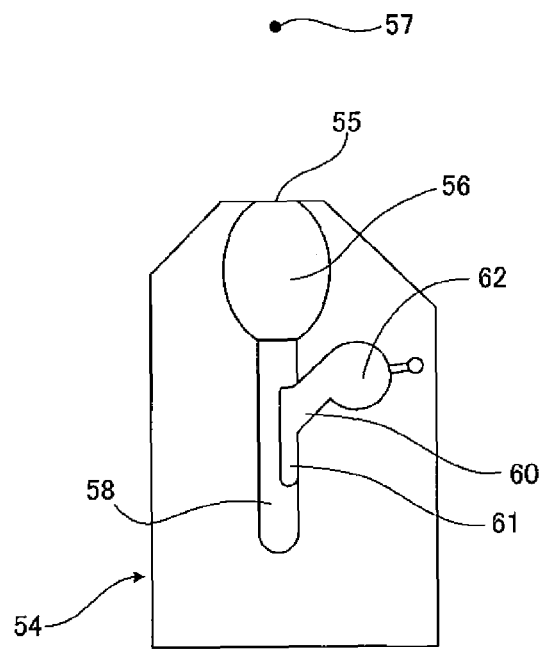
FIG. 59A is a plan view showing an analyzing device of Patent Document 1.
Figure 59B:
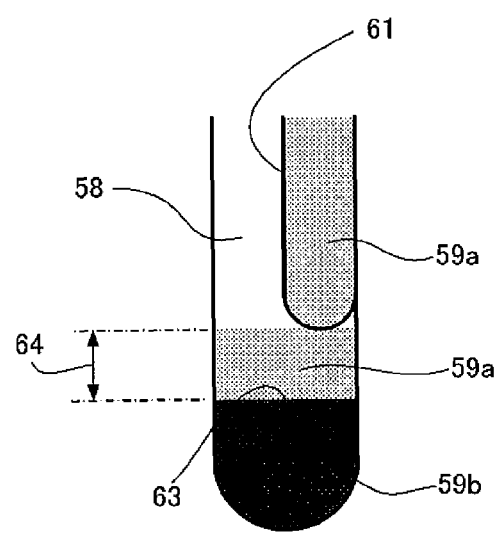
FIG. 59B is an enlarged view showing a part around the separation interface of the analyzing device according to Patent Document 1.
Figure 60:
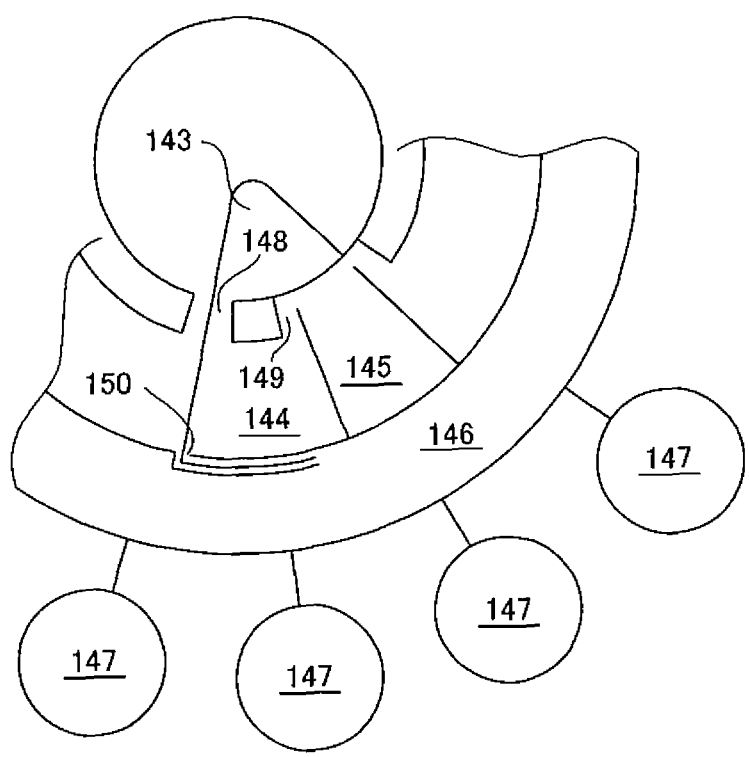
FIG. 60 is a plan view showing an analyzing device of Patent Document 2.
Figure 61:
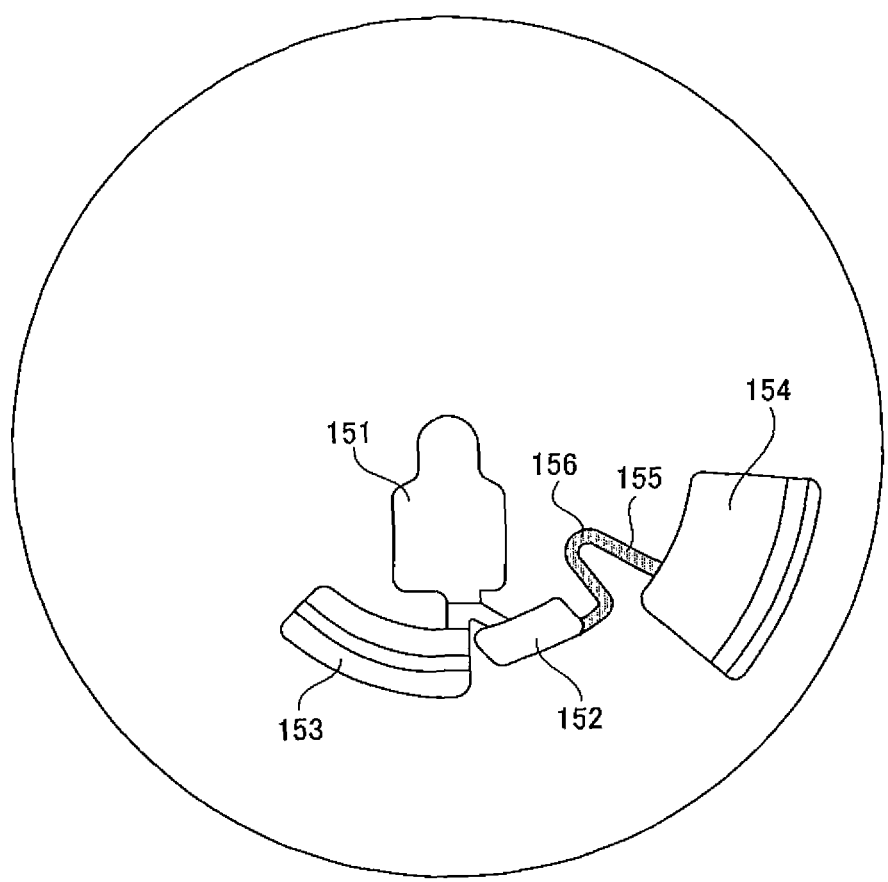
FIG. 61 is a plan view showing an analyzing device of Patent Document 3.
Figure 62:
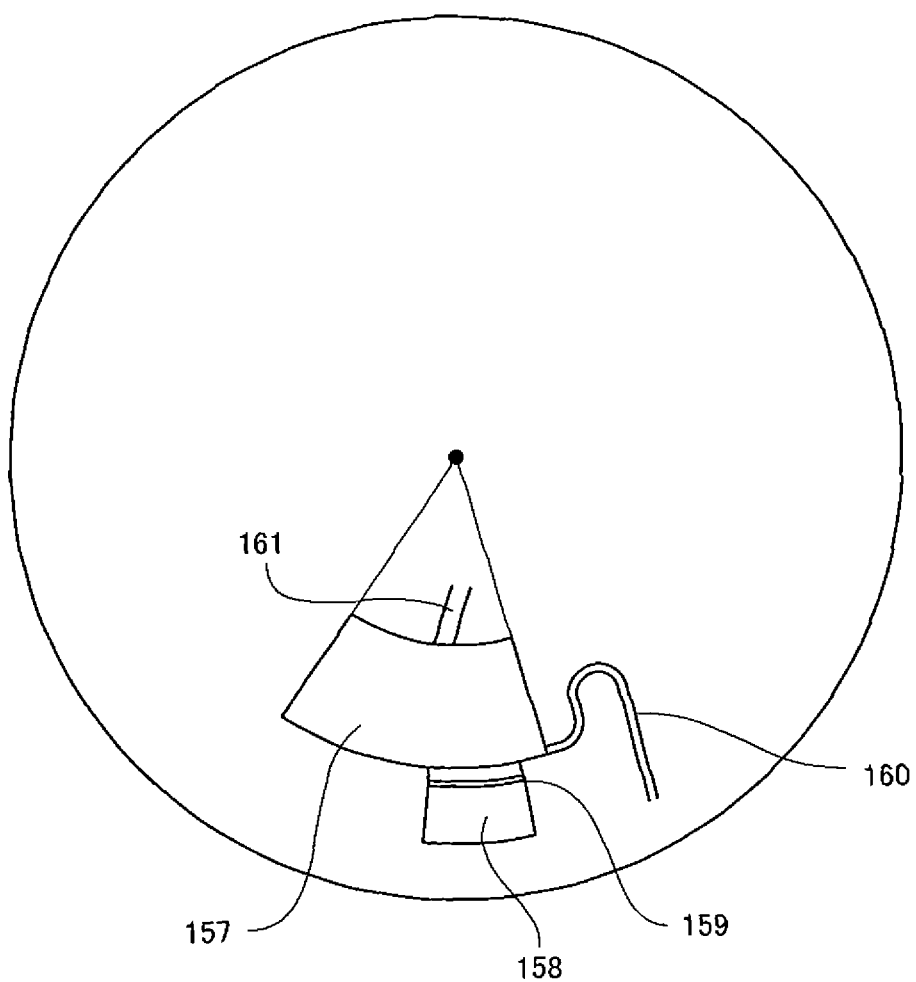
FIG. 62 is a plan view showing an analyzing device of Patent Document 4.
Figure 63:
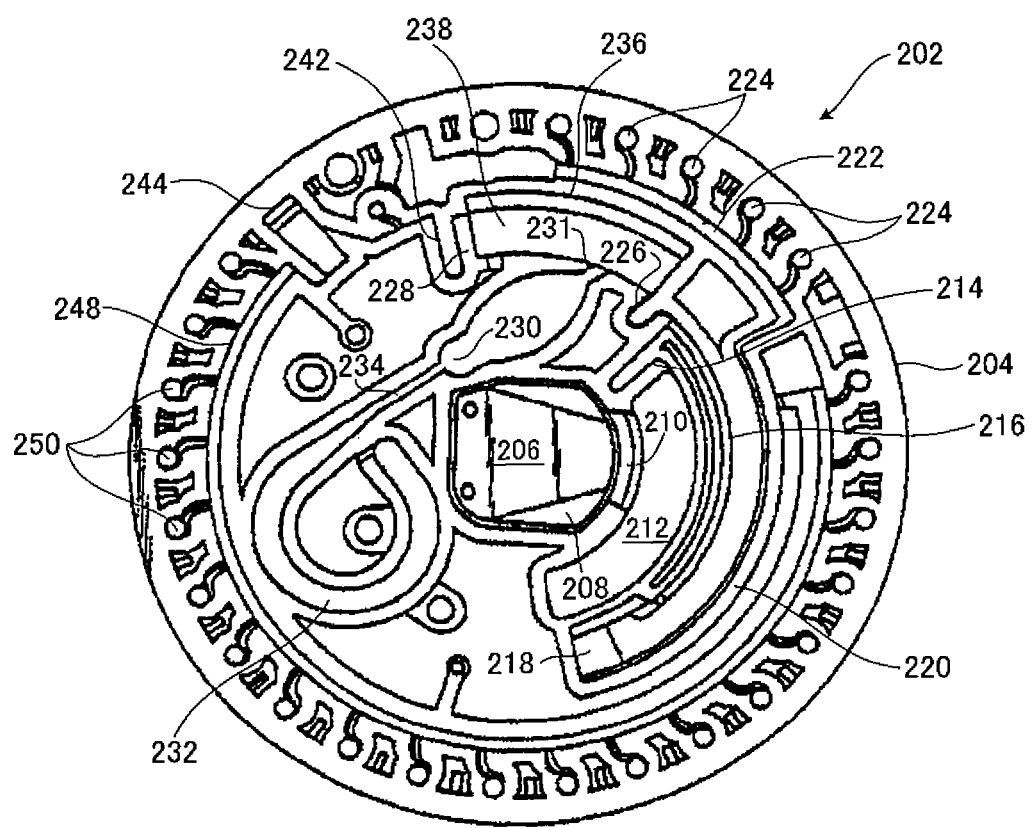
FIG. 63 is a plan view showing the main part of an analyzing device according to Patent Document 5.
Figure 64:
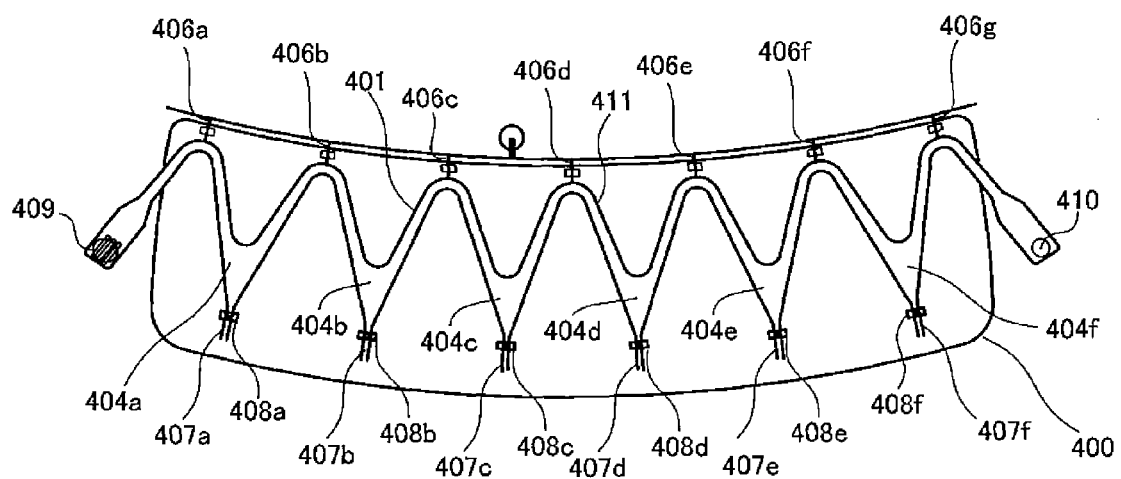
FIG. 64 is an explanatory drawing showing the distribution of a sample liquid in a centrifugal transfer biosensor of Patent Document 5.

FIGS. 49 to 56 show the embodiment of the present invention. FIGS. 57 and 58 show a comparative example.

Figure 49:
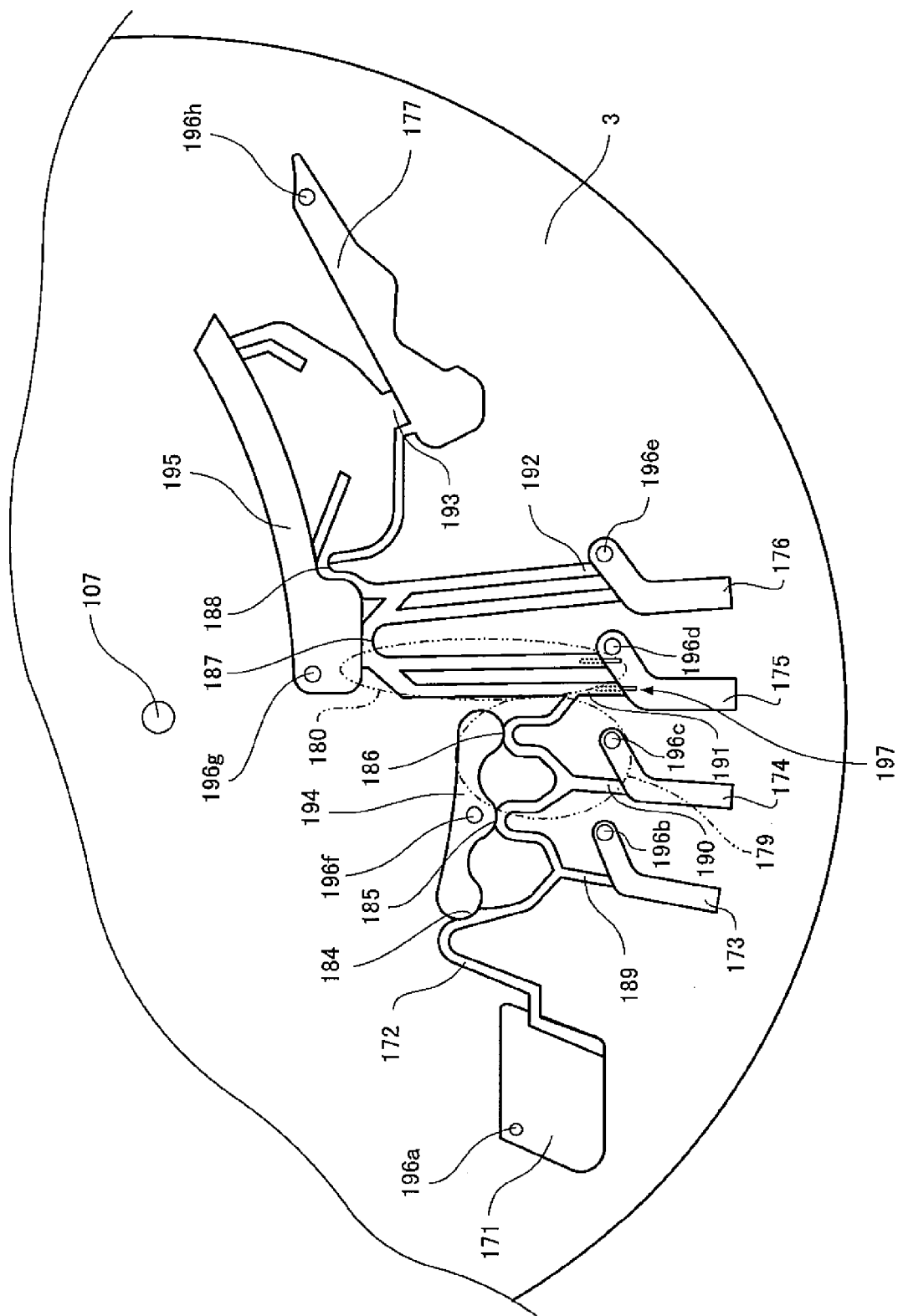
FIG. 49 is a top view showing a base substrate of the analyzing device according to the embodiment of the present invention.
Figure 50:
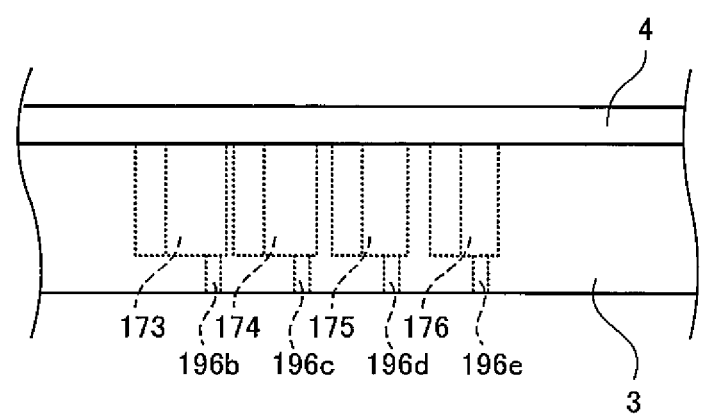
FIG. 50 is a side view showing the analyzing device of the embodiment.

As shown in FIGS. 49 and 50, an analyzing device according to the embodiment of the present invention is configured by bonding a base substrate 3 having a microchannel structure formed thereon, the microchannel structure having a minutely uneven surface, and a cover substrate 4 for covering the top surface of the base substrate 3. For convenience of explanation, the cover substrate 4 is omitted in FIG. 49.

Formed on the base substrate 3 are a filling chamber 171, measuring chambers 173, 174, 175, and 176, a discarding chamber 177, air hole chambers 194 and 195, and a quantifying capillary channel 172. Holes 196a, 196b, 196c, 196d, 196e, 196f, 196g, and 196h located at recessed portions in FIG. 49 are formed on the base substrate 3 and communicate with the atmosphere as shown in FIG. 50.

The measuring chambers 173 to 176 are arranged along the outer periphery relative to a rotation axis 107. The quantifying capillary channel 172 has its proximal end connected to the filling chamber 171 and is extended in a meandering manner between the rotation axis 107 and the measuring chambers 173 to 176 in the circumferential direction. The quantifying capillary channel 172 has liquid branch points 184, 185, 186, 187, and 188 at inflection points on the inner periphery side and has joints 189, 190, 191, and 192 for distributing a sample liquid, which has been branched at the liquid branch points, to the measuring chambers 173 to 176. Further, the quantifying capillary channel 172 distributes an excessive sample liquid to the discarding chamber 177 from a joint 193.

When the sample liquid is supplied into the filling chamber 171, the sample liquid fills the quantifying capillary channel 172 by a capillary force. In this configuration, the air hole chambers 194 and 195 are provided as air holes. The quantifying capillary channel 172 has a plurality of connected channels of a similar shape. In this configuration, alternately arranged are the liquid branch points on the side of the rotation axis 107 and the joints 189 to 193 provided on the outer periphery to introduce the sample liquid to the measuring chambers 173, 174, 175, and 176.

A centrifugal force is applied by rotating the analyzing device about the rotation axis 107 with the quantifying capillary channel 172 filled with the sample liquid, so that the sample liquid in the quantifying capillary channel 172 is divided to left and right at the liquid branch points of the quantifying capillary channel 172 and is transferred into the measuring chambers 173, 174, 175, and 176, the filling chamber 171, and the discarding chamber 177.

Figure 51:
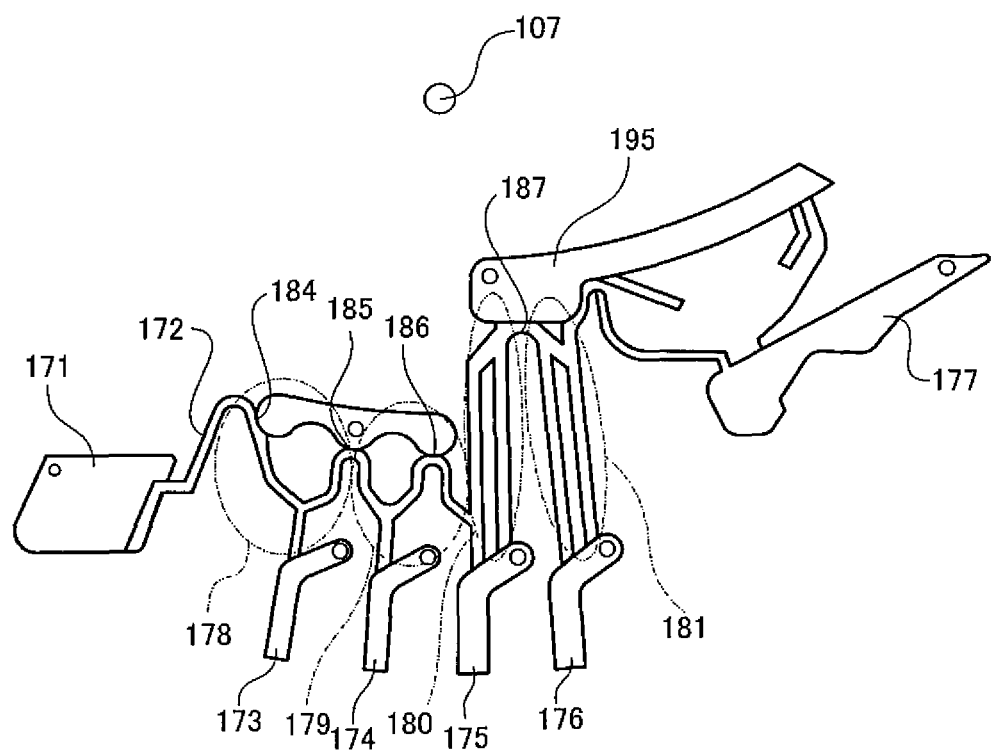
FIG. 51 is an explanatory drawing showing quantifying parts on a quantifying capillary channel according to the embodiment.

As indicated by virtual lines in FIG. 51, quantifying parts 178, 179, 180, and 181 are formed on the quantifying capillary channel 172. The measuring chambers 173, 174, 175, and 176 are disposed on the outside of the quantifying parts 178, 179, 180, and 181, respectively. The required amounts of the sample liquid in the measuring chambers 173, 174, 175, and 176 are equivalent to the capacities of the divided quantifying parts 178, 179, 180, and 181 that range from the liquid branch point 184 to the liquid branch point 188 in the quantifying capillary channel 172. The quantifying parts 178 and 179 are designed with a capacity of 3 µl and the quantifying parts 180 and 181 are designed with a capacity of 7 µl.

In the present embodiment, as shown in FIGS. 52 to 55, characteristic members 197 are provided at the joints 191 of the quantifying part 180 and the measuring chamber 175.

Prior to the explanation of the characteristic members 197, a comparative example will be described below.

The comparative example of FIG. 57 is identical in configuration to FIGS. 49 to 51 except for the characteristic members 197 provided at the joints 191.

As shown in FIG. 58(a), the sample liquid supplied into the filling chamber 171 fills the quantifying capillary channel 172 by a capillary force. In this state, a centrifugal force is applied by rotating the analyzing device about the rotation axis 107 at, for example, 4000 rpm. Thus the sample liquid retained in the quantifying capillary channel 172 as shown in FIG. 58(b) is divided at the liquid branch points and is transferred to the measuring chambers 173, 174, 175, and 176 as shown in FIG. 58(c). When the amount of the sample liquid increases in the quantifying capillary channel 172, it is necessary to change the width and length of the capillary channel. When the length of the quantifying capillary channel 172 is changed to keep a constant capillary force, distances from the rotation axis 107 to the liquid branch points 187 and 188 are shorter than distances from the rotation axis 107 to the liquid branch points 184, 185, and 186. The liquid is transferred from the rotation axis 107 to the outer periphery by a centrifugal force, so that the sample liquid is first transferred to the liquid branch points 187 and 188 located at shorter distances from the rotation axis 107. Hence, the transfer of the sample liquid to the liquid branch points 184, 185, and 186 located at longer distances from the rotation axis 107 is delayed from channels at the liquid branch points 187 and 188 located at shorter distances from the rotation axis 107. In this case, in a portion where the quantifying part 179 and the quantifying part 180 are adjacent to each other, the sample liquid firstly transferred to the liquid branch point 187 is not introduced to the measuring chamber 175 but flows into the quantifying part 179.

In a state in which the sample liquid of the quantifying capillary channel 172 has been transferred as shown in FIG. 58(c), the amount of the sample liquid varies among the measuring chambers 173, 174, 175, and 176. This is because a centrifugal force is small owing to a low rpm immediately after the start of rotation. Further, since the quantifying capillary channel 172 is filled with the sample liquid, surface tensions applied to the joints of the quantifying parts are smaller than surface tensions applied to the joints of the quantifying parts 178, 179, 180, and 181 and the measuring chambers 173, 174, 175, and 176. Thus a centrifugal force at a low rpm cannot introduce the sample liquid into the measuring chambers and the sample liquid flows into an adjacent channel having been already filled with the sample liquid. Consequently, regarding the measuring chambers 173 and 174 that receive the sample liquid from locations having the liquid branch points at equal distances from the rotation axis 107, the sample liquid to be supplied to the measuring chamber 175 partially flows into the measuring chamber 174 as indicated by an arrow in FIG. 58(b). Thus the amount of the sample liquid in the measuring chamber 174 is larger than the amount of the sample liquid in the measuring chamber 173, resulting in variations in the amount of the sample liquid between the measuring chamber 173 and the measuring chamber 174. Further, regarding the measuring chambers 175 and 176 that receive the sample liquid from locations having the liquid branch points at equal distances from the rotation axis 107, the sample liquid to be supplied to the measuring chamber 175 partially flows into the measuring chamber 176 in vain as indicated by an arrow in FIG. 58(b). Thus the amount of the sample liquid in the measuring chamber 175 is smaller than the amount of the sample liquid in the measuring chamber 176, resulting in variations in the amount of the sample liquid between the measuring chamber 175 and the measuring chamber 176.

In the present embodiment, the characteristic members 197 of FIGS. 52 to 55 are provided to reduce variations in the amount of the sample liquid between the measuring chamber 173 and the measuring chamber 174 and variations in the amount of the sample liquid between the measuring chamber 175 and the measuring chamber 176. In portions having the liquid branch points located at different distances from the rotation axis, the characteristic members 197 enable a larger sectional area on the channel of the joint with the measuring chamber for receiving the sample liquid from the liquid branch point at a shorter distance from the rotation axis, as compared with the joint of the channel connected to the liquid branch point at a longer distance from the rotation axis and the channel connected to the liquid branch point at a shorter distance from the rotation axis, so that the sample liquid easily flows into the measuring chamber 175. Thus when the liquid is transferred by a centrifugal force, the sample liquid easily flows into the measuring chamber 175 and the sample liquid is introduced into the measuring chamber 175 before entering the adjacent quantifying part 179, thereby quantifying the amounts of the sample liquid introduced into the measuring chambers.

To be specific, as shown in FIGS. 52 to 55, guide capillary channels 182a and 182b are formed as the characteristic members 197 on the cover substrate 4. The guide capillary channels 182a and 182b are shaped like grooves communicating with the joints 191 formed on the base substrate 3. In the comparative example, the guide capillary channels 182a and 182b and the like are not provided and thus the opening of the joint 191 in the measuring chamber 175 has the same sectional area as the opening of a connected point E between the quantifying part 179 and the quantifying part 180.

Figure 52:
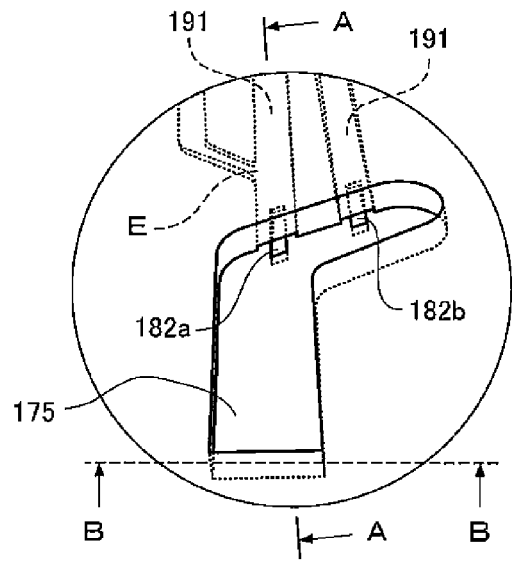
FIG. 52 is an enlarged perspective view showing the cross section of the joint of a quantifying part 180 and a measuring chamber 175.
Figure 53:
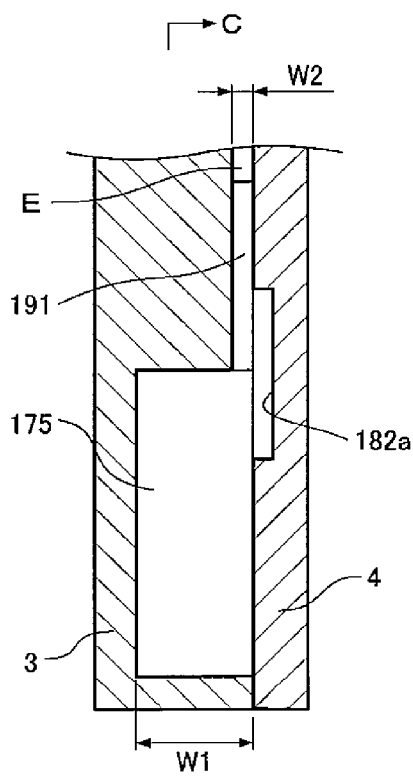
FIG. 53 is an A-A sectional view showing the quantifying part 180 and the measuring chamber 175.
Figure 54:
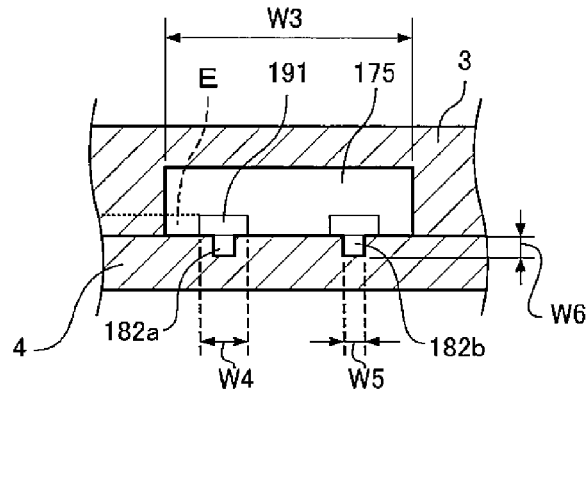
FIG. 54 is a sectional view showing a B-B joint of the quantifying part 180 and the measuring chamber 175.
Figure 55:
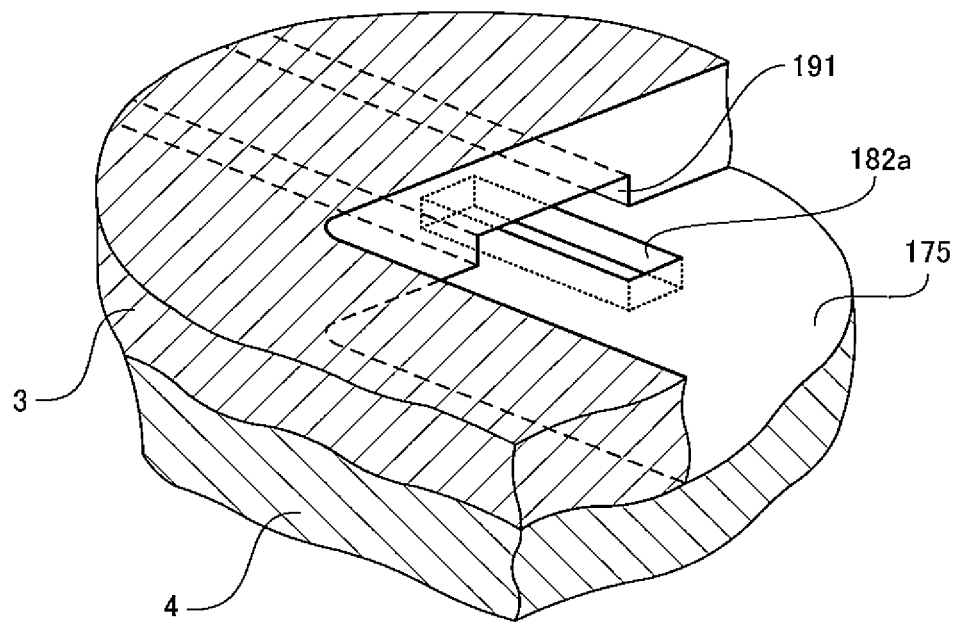
FIG. 55 is an enlarged perspective view showing a guide capillary channel of the embodiment.

FIG. 52 is an enlarged perspective view showing the joint of the quantifying part 180 and the measuring chamber 175 having a large sectional area. FIGS. 53 and 54 are A-A and B-B sectional views showing the joint of the quantifying part 180 and the measuring chamber 175. The measuring chamber 175 has a thickness W1 of 3 mm, the quantifying capillary channel 172 has a thickness W2 of 0.3 mm, the measuring chamber 175 has a width W3 of 5 mm, and the quantifying capillary channel 172 has a width W4 of 2 mm. The guide capillary channels 182a and 182b for increasing the sectional area of the joint of the quantifying part 180 and the measuring chamber 175 each have a width W5 of 1 mm and a thickness W6 of 0.5 mm. FIG. 52 is a C-C sectional view of FIG. 53.

Moreover, hydrophilic treatment is performed on a surface where the width of the quantifying capillary channel 172 is set, so that the sample liquid flows on the surface by a capillary force. The surfaces of the guide capillary channels 182a and 182b are all subjected to hydrophilic treatment. When the guide capillary channels 182a and 182b are not provided, the joints of the quantifying parts have the same sectional area as the joints of the quantifying capillary channel 172 and the measuring chambers. When the guide capillary channels 182a and 182b are provided, portions having the guide capillary channels 182a and 182b are larger in sectional area. Thus the surface tension of the sample liquid decreases and the liquid can be easily discharged. In this case, regarding the sectional area for introducing the sample liquid from the quantifying part into the measuring chamber 175 without introducing the sample liquid into the other channels, the sectional area may be optionally set as long as a pressure applied to the joint of the quantifying part 180 and the measuring chamber 175 can be lower than pressures applied to the other joints. The following will calculate the minimum channel width and thickness for reducing a pressure applied to the cross sections of the quantifying part 180 and the measuring chamber 175. A length X for expansion is calculated as follows:

$$X = \gamma/(m \cdot r \cdot \omega^2/S)$$

where X is the length for expansion, m is a molecular mass, r is a radius of gyration, $\omega$ is the number of revolutions, S is a sectional area, and $\gamma$ is a surface tension.

A pressure applied to each joint can be determined by $(m \cdot r \cdot \omega^2/S)$. In the present embodiment, the surface tension was 0.07 N/m, the radius of gyration r was 15 mm, the number of revolutions $\omega$ was 4000 rpm, a channel width w was 2 mm, and a channel thickness t was 0.3 mm. When the guide capillary channels 182a and 182b are not provided, pressures at the joints of the quantifying parts and the measuring chambers are about 4383 N/m². Thus when a pressure applied to the joint of the quantifying part 180 and the measuring chamber 175 can be lower than these pressures, the sample liquid can be introduced into the measuring chamber 175. The minimum channel width and thickness of the guide capillary channels 182a and 182b are obtained by adding, to the channel width and thickness, at least 0.017 mm that is a length for discharging the liquid at a pressure applied during rotation by a centrifugal force. In other words, the channel width is set at 2.017 mm and the thickness is set at 0.317 mm. Further, the maximum channel width is set at 2 mm for the quantifying capillary channel 172. The following will describe the effect of these shapes.

Figure 56:
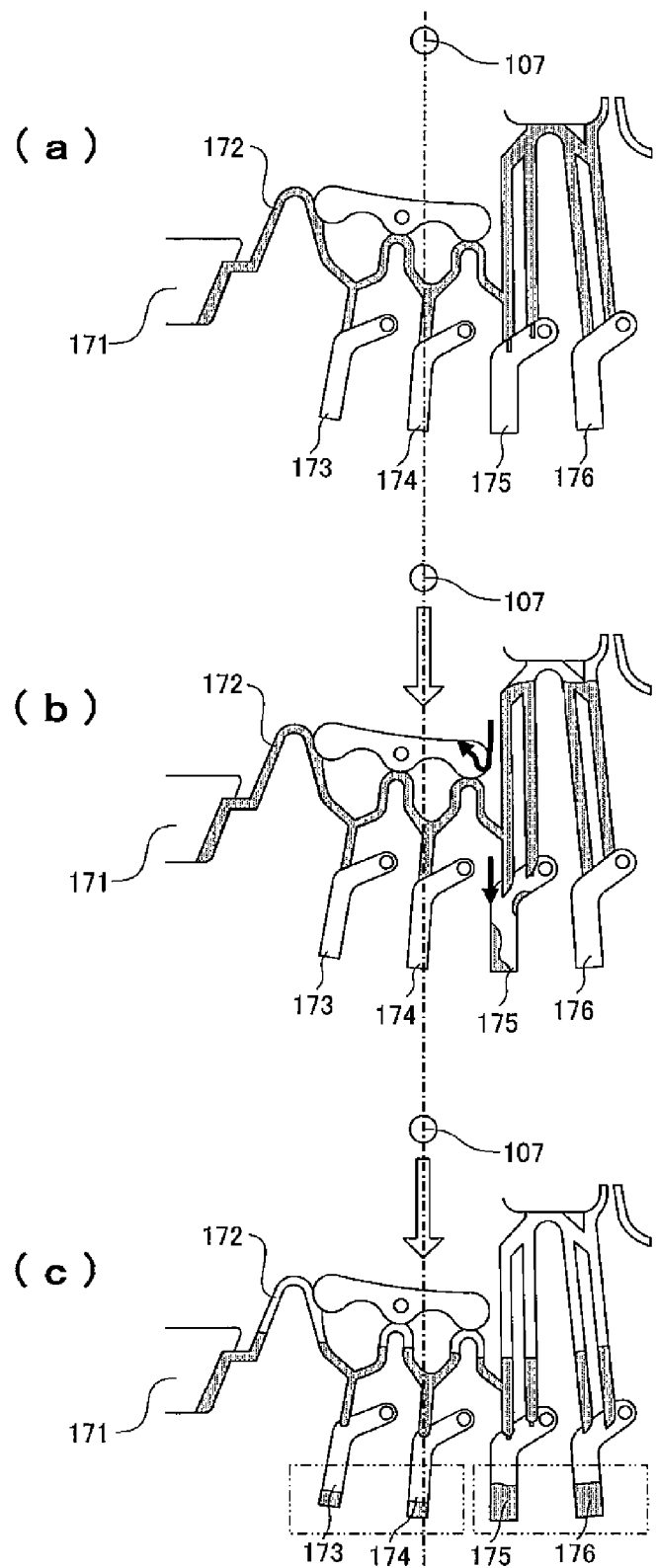
FIG. 56 is a flow pattern diagram of the embodiment.

FIG. 56 shows a flow pattern when the guide capillary channels 182a and 182b are provided.

FIG. 56(a) shows a state in which the sample liquid in the quantifying capillary channel is transferred by a centrifugal force. In FIG. 56(b), the application of a centrifugal force transfers the sample liquid of the quantifying parts 180 and 181 to the outer periphery. However, the guide capillary channels 182a and 182b reduce a surface tension applied to the joint of the quantifying part 180 and the measuring chamber 175 and thus the sample liquid can be introduced into the measuring chamber 175 even at a low rpm. FIG. 56(c) shows that the amount of the sample liquid transferred into the measuring chamber 175 is equal to the amount of the sample liquid in the measuring chamber 176. Hence, it was confirmed that a sectional area increased by the guide capillary channels 182a and 182b provided at the joint of the measuring chamber 175 and the quantifying capillary channel 172 makes it possible to easily introduce the sample liquid into the measuring chamber when a centrifugal force is larger than a surface tension, thereby reducing variations in the amount of the sample liquid between the measuring chamber 173 and the measuring chamber 174 and variations in the amount of the sample liquid between the measuring chamber 175 and the measuring chamber 176.

As previously mentioned, the joint of the quantifying part 180 and the measuring chamber 175 has a larger sectional area than the joint of the quantifying parts. Thus when a pressure is reduced to easily transfer the sample liquid into the measuring chamber 175, the sample liquid quantified in the quantifying parts can be transferred to the measuring chamber.

In the foregoing embodiment, the length X for expansion is added to the channel thickness of the joint of the quantifying parts. The length X for expansion may be added to the channel width of the joint of the quantifying parts.

INDUSTRIAL APPLICABILITY

The present invention is useful as a transfer control unit of an analyzing device that is used for analyzing the component of a liquid collected from an organism and the like.

The invention claimed is:

1. An analyzing device having a microchannel structure comprising:
a rotation axis;
a separating cavity having first, second and third sidewalls, the first and third sidewalls being each formed in a generally straight line shape, the second sidewall being formed along an outermost periphery of the separating cavity and connecting the first and third sidewalls, and configured to separate a sample liquid into a solution component and a solid component by using a centrifugal force;
a measurement channel configured to receive and retain the solution component;
a first connecting channel provided between the measurement channel and the separating cavity to transfer the solution component from the separating cavity, the first sidewall of the separating cavity being located closer to the first connecting channel than the third sidewall of the separating cavity; and
a first capillary cavity defined within the separating cavity and connected to the first and second sidewalls of the separating cavity and not the third sidewall of the separating cavity, the capillary cavity extending along the first sidewall of the separating cavity, the first capillary cavity having a first end communicating with the first connecting channel and a second end directly connected to the second sidewall of the separating cavity, the first end of the first capillary cavity being located closer to the rotation axis than the second end of the first capillary cavity, a clearance of the first capillary cavity being smaller than a depth of the separating cavity.

2. The analyzing device according to claim 1, further comprising:
   an overflow cavity located farther away from the rotation axis than the separating cavity; and
   a second connecting channel having a first end communicating with the overflow cavity, a second end communicating with the second sidewall of the separating cavity, and a siphon structure located closer to the rotation axis than the first and second ends of the second connecting channel.

3. The analyzing device according to claim 1, further comprising:
   an overflow cavity located farther away from the rotation axis than the separating cavity;
   a second capillary cavity located farther away from the rotation axis than the separating cavity and closer to the rotation axis than the overflow cavity, the second capillary cavity communicating with the second sidewall of the separating cavity and a clearance of the second capillary cavity being smaller than the depth of the separating cavity; and
   a second connecting channel having a first end, a second end and a siphon structure, the first end communicating with the overflow cavity, the second end communicating with the second capillary cavity, the siphon structure being located closer to the rotation axis than the first and second ends of the second connecting channel.

4. The analyzing device according to claim 3, wherein the second capillary cavity communicates with the first capillary cavity.

5. The analyzing device according to claim 1, wherein the separating cavity is interiorly divided into a plasma retaining part and a blood cell retaining part by a blood separating wall, the plasma retaining part is located closer to the rotation axis than the blood cell retaining part, the first capillary cavity and an air channel are formed on the blood separating wall, the plasma retaining part and the blood cell retaining part are communicated with each other by the first capillary cavity and by the air channel,
   wherein when the analyzing device is being rotated, the solution component moves toward the plasma retaining part, and the solid component moves toward the blood cell retaining part, and the capillary cavity is configured to transfer a solution component remaining in the blood cell retaining part to the measurement channel through the first connecting channel by a capillary force.

6. The analyzing device according to claim 5, wherein the blood separating wall has a wall surface in contact with the blood cell retaining part, the wall surface being formed of a circular surface at a constant distance from a rotation center.

7. An analyzing method, comprising:
   rotating an analyzing device to transfer a sample liquid to a separating cavity and centrifugally separate the sample liquid to form a solution component and a solid component by rotating the analyzing device around a rotation axis, the separating cavity having first, second and third sidewalls, the first and third sidewalls being each formed in a generally straight line shape, the second sidewall formed along an outermost periphery of the separating cavity and connecting the first and third sidewalls;
   stopping the rotation to draw the solution component firstly through a first capillary cavity located within the separating cavity, the first capillary cavity being connected only to the first and second sidewalls of the separating cavity and not to the third sidewall of the separating cavity, the first capillary cavity extending along the first sidewall of the separating cavity, the first capillary cavity having a first end and a second end, the first end of the first capillary cavity being located closer to the rotation axis than the second end of the first capillary cavity, the second end of the first capillary cavity being directly connected to the second sidewall of the separating cavity, a clearance of the first capillary cavity being smaller than a depth of the separating cavity, a second end of the first capillary cavity located farther away from the rotation axis;
   transferring the solution component to a measurement channel through a first connecting channel which communicates with the first end of the first capillary cavity, the first sidewall of the separating cavity being located closer to the first connecting channel than the third sidewall of the separating cavity;
   rotating the analyzing device to transfer the solution component in from the measurement channel to a measuring chamber and mix the solution component with a reagent to make an analysis sample; and
   accessing the analysis sample at a measurement spot when the measuring chamber is located at a reading position.

* * * * *